(12) United States Patent
Klose et al.

(10) Patent No.: US 10,575,934 B2
(45) Date of Patent: Mar. 3, 2020

(54) SYSTEMS AND METHODS FOR IMAGING OF AN ANATOMICAL STRUCTURE

(71) Applicant: In Vivo Analytics, Inc., New York, NY (US)

(72) Inventors: Alexander Klose, New York, NY (US); Neal Paragas, Seattle, WA (US)

(73) Assignee: In Vivo Analytics, Inc., New York, NY (US)

(*) Notice: Subject to any disclaimer, the term of this patent is extended or adjusted under 35 U.S.C. 154(b) by 0 days.

(21) Appl. No.: 15/621,983

(22) Filed: Jun. 13, 2017

(65) Prior Publication Data
US 2017/0354487 A1  Dec. 14, 2017

Related U.S. Application Data

(60) Provisional application No. 62/350,129, filed on Jun. 14, 2016, provisional application No. 62/350,128, (Continued)

(51) Int. Cl.
*A01K 1/03*  (2006.01)
*A01K 1/035*  (2006.01)
(Continued)

(52) U.S. Cl.
CPC ............... *A61D 3/00* (2013.01); *A01K 1/03* (2013.01); *A01K 1/035* (2013.01); *A01K 15/04* (2013.01);
(Continued)

(58) Field of Classification Search
CPC ...... A01K 1/0613; A01K 1/035; A01K 15/04; A01K 1/03; A61D 3/00; A61D 7/04; A61B 5/0059; A61B 2503/40
See application file for complete search history.

(56) References Cited

U.S. PATENT DOCUMENTS 4,204,738 A * 5/1980 Tillotson ............ H01R 13/6392
                                                          439/369
D297,322 S * 8/1988 Johnson ....................... D13/134
(Continued)

FOREIGN PATENT DOCUMENTS

WO   WO 2007/089641 A2   8/2007
WO   WO 2009/120758 A1   10/2009
(Continued)

OTHER PUBLICATIONS

Jax Corp. 2015 Body weight info for C57BL/6J Internet address: https://www.jax.org/jax-mice-and-services/strain-data-sheet-pages/body-weight-chart-000664 , 1 page.*
(Continued)

*Primary Examiner* — Baisakhi Roy
*Assistant Examiner* — Patrick M Mehl
(74) *Attorney, Agent, or Firm* — Knobbe Martens Olson & Bear, LLP

(57) ABSTRACT

Systems and method for optical imaging of an animal include a body conforming animal mold, which is shaped and sized to hold an animal in an immobilized and geometrically defined position and a gantry, which can include multiple optical mirrors to provide for simultaneous imaging of multiple different views of an animal within a body conforming animal mold.

18 Claims, 55 Drawing Sheets

Related U.S. Application Data filed on Jun. 14, 2016, provisional application No. 62/382,654, filed on Sep. 1, 2016, provisional application No. 62/382,679, filed on Sep. 1, 2016.

(51) Int. Cl.
| | |
|---|---|
| *A61B 5/00* | (2006.01) |
| *A61D 3/00* | (2006.01) |
| *A61D 7/04* | (2006.01) |
| *A01K 15/04* | (2006.01) |

(52) U.S. Cl.
CPC .............. *A61B 5/0059* (2013.01); *A61D 7/04* (2013.01); *A61B 2503/40* (2013.01)

(56) References Cited

U.S. PATENT DOCUMENTS

| | | | | |
|---|---|---|---|---|
| 7,681,527 | B2* | 3/2010 | Pratt | A01K 29/00 |
| | | | | 119/174 |
| 7,784,429 | B2* | 8/2010 | Chiodo | A01K 1/0613 |
| | | | | 119/417 |
| 8,317,098 | B2* | 11/2012 | Roth | G06Q 30/018 |
| | | | | 235/385 |
| 8,918,163 | B2* | 12/2014 | Yared | A61B 6/0421 |
| | | | | 119/417 |
| 2003/0085908 | A1* | 5/2003 | Luby | G06T 7/70 |
| | | | | 345/619 |
| 2008/0072836 | A1* | 3/2008 | Chiodo | A61D 3/00 |
| | | | | 119/417 |
| 2008/0319310 | A1* | 12/2008 | Mukherjee | A61B 6/037 |
| | | | | 600/420 |
| 2009/0080600 | A1* | 3/2009 | Keller | G01N 1/30 |
| | | | | 378/18 |
| 2012/0017842 | A1* | 1/2012 | Yamada | G01N 21/01 |
| | | | | 119/421 |
| 2012/0259230 | A1* | 10/2012 | Riley | A61B 5/1072 |
| | | | | 600/477 |
| 2015/0012224 | A1 | 1/2015 | Klose et al. | |

FOREIGN PATENT DOCUMENTS

| | | | |
|---|---|---|---|
| WO | WO 2012/135601 | A2 | 10/2012 |
| WO | WO-2012135601 | A2 * | 10/2012 ........... A61B 51/055 |

OTHER PUBLICATIONS

Klose et al. 2018 Nature Communications 9:4262 12pages (Year: 2018).*

Hillman et al. 2007 Nat. Photonics 1:526-530 (Year: 2007).*

Allard, Mathieu, et al. "Combined magnetic resonance and bioluminescence imaging of live mice." *Journal of biomedical optics* 12.3 (2007): 034018.

Badr, Christian E., and Bakhos A. Tannous. "Bioluminescence imaging: progress and applications." *Trends in biotechnology* 29.12 (2011): 624-633.

Baiker, Martin, et al. "Atlas-based whole-body segmentation of mice from low-contrast Micro-CT data." *Medical image analysis* 14.6 (2010): 723-737.

Baiker, Martin, et al. "Atlas-driven scan planning for high-resolution micro-SPECT data acquisition based on multi-view photographs: a pilot study." *Proceedings of SPIE*, 2009, vol. 72611L (2009).

Begley, C. Glenn, and Lee M. Ellis. "Drug development: Raise standards for preclinical cancer research." *Nature* 483.7391 (2012): 531-533.

Bonetto, Paola, Jinyi Qi, and Richard M. Leahy. "Covariance approximation for fast and accurate computation of channelized Hotelling observer statistics." *IEEE Transactions on Nuclear Science* 47.4 (2000): 1567-1572.

Buchholz U, Bernard H, Werber D, Bohmer MM, Remschmidt C, Wilking H, et al., "German Outbreak of *Escherichia coli* O104:H4 Associated with Sprouts," *The New England Journal of Medicine*. 2011;365(19):1763-70.

Chaudhari, Abhijit J., et al. "A method for atlas-based volumetric registration with surface constraints for optical bioluminescence tomography in small animal imaging." *Proc. SPIE*. vol. 6510. No. 651024. 2007.

Chaudhari, Abhijit J., et al. "Hyperspectral and multispectral bioluminescence optical tomography for small animal imaging." *Physics in medicine and biology* 50.23 (2005): 5421-5441.

De Almeida, Patricia E., Juliaan RM van Rappard, and Joseph C. Wu. "In vivo bioluminescence for tracking cell fate and function." *American Journal of Physiology-Heart and Circulatory Physiology* 301.3 (2011): H663-H671.

Dutta, Joyita, Sangtae Ahn, and Quanzheng Li. "Quantitative statistical methods for image quality assessment." *Theranostics* 3.10 (2013): 741.

Fessler, Jeffrey A. "Mean and variance of implicitly defined biased estimators (such as penalized maximum likelihood): Applications to tomography." *IEEE Transactions on Image Processing* 5.3 (1996): 493-506.

Fessler, Jeffrey A., and Anastasia Yendiki. "Channelized Hotelling observer performance for penalized-likelihood image reconstruction." *Nuclear Science Symposium Conference Record, 2002 IEEE*. vol. 2. IEEE, 2002.

Foucault, M-L., et al. "In vivo bioluminescence imaging for the study of intestinal colonization by *Escherichia coli* in mice." *Applied and environmental microbiology* 76.1 (2010): 264-274.

Foxman, Betsy. "Epidemiology of urinary tract infections: incidence, morbidity, and economic costs." *Disease-a-month* 49.2 (2003): 53-70.

Fu, Lin, et al. "Quantitative accuracy of penalized-likelihood reconstruction for ROI activity estimation." *IEEE transactions on nuclear science* 56.1 (2009): 167-172.

Hidron, Alicia I., et al. "Antimicrobial-resistant pathogens associated with healthcare-associated infections: annual summary of data reported to the National Healthcare Safety Network at the Centers for Disease Control and Prevention, 2006-2007." *Infection Control & Hospital Epidemiology* 29.11 (2008): 996-1011.

Hooton, Thomas M. "The current management strategies for community-acquired urinary tract infection." *Infectious disease clinics of North America* 17.2 (2003): 303-332.

Hopkins, Walter J., et al. "Time course and host responses to *Escherichia coli* urinary tract infection in genetically distinct mouse strains." *Infection and immunity* 66.6 (1998): 2798-2802.

Hughes, James M. "Preserving the lifesaving power of antimicrobial agents." *Jama* 305.10 (2011): 1027-1028.

Hutchens, Martha, and Gary D. Luker. "Applications of bioluminescence imaging to the study of infectious diseases." *Cellular microbiology* 9.10 (2007): 2315-2322.

Jacques, Steven L. "Optical properties of biological tissues: a review." *Physics in medicine and biology* 58.11 (2013): R37.

Joshi, Anand A., et al. "DigiWarp: a method for deformable mouse atlas warping to surface topographic data." *Physics in medicine and biology* 55.20 (2010): 6197-6214.

Joshi, Anand A., et al. "Posture matching and elastic registration of a mouse atlas to surface topography range data." *Biomedical Imaging: From Nano to Macro, 2009. ISBI'09. IEEE International Symposium on*. IEEE, 2009:366-9.

Keyaerts, Marleen, Vicky Caveliers, and Tony Lahoutte. "Bioluminescence imaging: looking beyond the light." *Trends in molecular medicine* 18.3 (2012): 164-172.

Klose, Alexander D. "Multi-spectral luminescence tomography with the simplified spherical harmonics equations." *Light Scattering Reviews* 7. Springer Berlin Heidelberg, 2013. 37-67.

Klose, Alexander D. "Radiative transfer of luminescence light in biological tissue." *Light Scattering Reviews* 4. Springer Berlin Heidelberg, 2009. 293-345.

Klose, Alexander D., and Edward W. Larsen. "Light transport in biological tissue based on the simplified spherical harmonics equations." *Journal of Computational Physics* 220.1 (2006): 441-470.

(56) References Cited

OTHER PUBLICATIONS

Klose, Alexander D., and Thomas Pöschinger. "Excitation-resolved fluorescence tomography with simplified spherical harmonics equations." *Physics in medicine and biology* 56.5 (2011): 1443-1469.

Klose, Alexander D., et al. "In vivo bioluminescence tomography with a blocking-off finite-difference SP₃ method and MRI/CT coregistration." *Medical physics* 37.1 (2010): 329-338.

Kuo, Chaincy, and Barbara Romanowicz. "On the resolution of density anomalies in the Earth's mantle using spectral fitting of normal-mode data." *Geophysical Journal International* 150.1 (2002): 162-179.

Kurvet, Imbi, et al. "LuxCDABE—Transformed constitutively bioluminescent *Escherichia coli* for toxicity screening: Comparison with naturally luminous Vibrio fischeri." *Sensors* 11.8 (2011): 7865-7878.

Menke, William. *Geophysical data analysis: discrete inverse theory: MATLAB edition*. vol. 45. Academic press, 2012.

Pharmaceutical Research and Manufacturers of America, Medicines in Development: Infectious Diseases (2007).

Platiša, Ljiljana, et al. "Channelized Hotelling observers for the assessment of volumetric imaging data sets." *JOSA A* 28.6 (2011): 1145-1163.

Prahl, Scott "Optical Absorption of Hemoglobin" http://omlc.ogi.edu/spectra/hemoglobin/ (1999).

Ronald, A. R., et al. "Urinary tract infection in adults: research priorities and strategies." *International journal of antimicrobial agents* 17.4 (2001): 343-348.

Saint, Sanjay. "Clinical and economic consequences of nosocomial catheter-related bacteriuria." *American journal of infection control* 28.1 (2000): 68-75.

Schilling, Joel D., et al. "Bacterial invasion augments epithelial cytokine responses to *Escherichia coli* through a lipopolysaccharide-dependent mechanism." *The Journal of Immunology* 166.2 (2001): 1148-1155.

Sjollema, Jelmer, et al. "The potential for bio-optical imaging of biomaterial-associated infection in vivo." *Biomaterials* 31.8 (2010): 1984-1995.

Virostko, John, Alvin C. Powers, and E. Duco Jansen. "Validation of luminescent source reconstruction using single-view spectrally resolved bioluminescence images." *Applied optics* 46.13 (2007): 2540-2547.

Wang, Ge, Yi Li, and Ming Jiang. "Uniqueness theorems in bioluminescence tomography." *Medical physics* 31.8 (2004): 2289-2299.

Wang, Hongkai, David B. Stout, and Anion F. Chatziioannou. "Estimation of mouse organ locations through registration of a statistical mouse atlas with micro-CT images." *IEEE transactions on medical imaging* 31.1 (2012): 88-102.

Wang, Hongkai, David B. Stout, and Anion F. Chatziioannou. "Mouse atlas registration with non-tomographic imaging modalities—a pilot study based on simulation." *Molecular Imaging and Biology* 14.4 (2012): 408-419.

Wang, Hongkai, et al. "MARS: a mouse atlas registration system based on a planar x-ray projector and an optical camera." *Physics in Medicine and Biology* 57.19 (2012): 6063-6077.

Welsh, David K., and Steve A. Kay. "Bioluminescence imaging in living organisms." *Current opinion in biotechnology* 16.1 (2005): 73-78.

Wildeman, M. H., et al. "2D/3D registration of micro-CT data to multi-view photographs based on a 3D distance map." *Biomedical Imaging: From Nano to Macro, 2009. ISBI'09. IEEE International Symposium on. IEEE*, 2009, 987-90.

Wiles, Siouxsie, et al. "Bioluminescent monitoring of in vivo colonization and clearance dynamics by light-emitting bacteria." *Bioluminescence: Methods and Protocols* (2009): 137-153.

Invitation to Pay Additional Fees: Annex to Form PCT/ISA/206, Communication Relating to the Results of the Partial International Search dated Sep. 1, 2017 in PCT/US2017/037185 filed Jun. 13, 2017.

International Search Report and Written Opinion dated Oct. 23, 2017, received in PCT/US2017/037185 filed Jun. 13, 2017.

\* cited by examiner

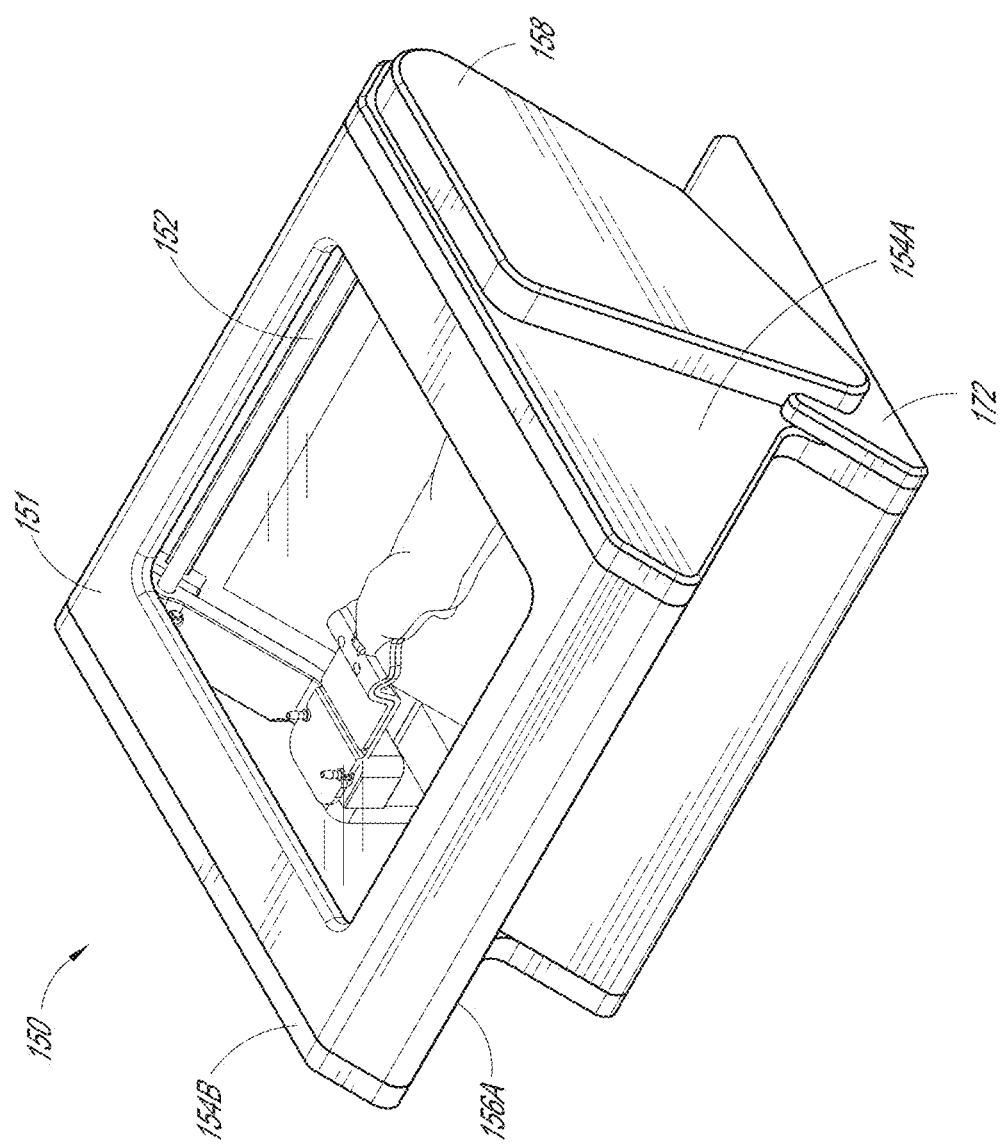

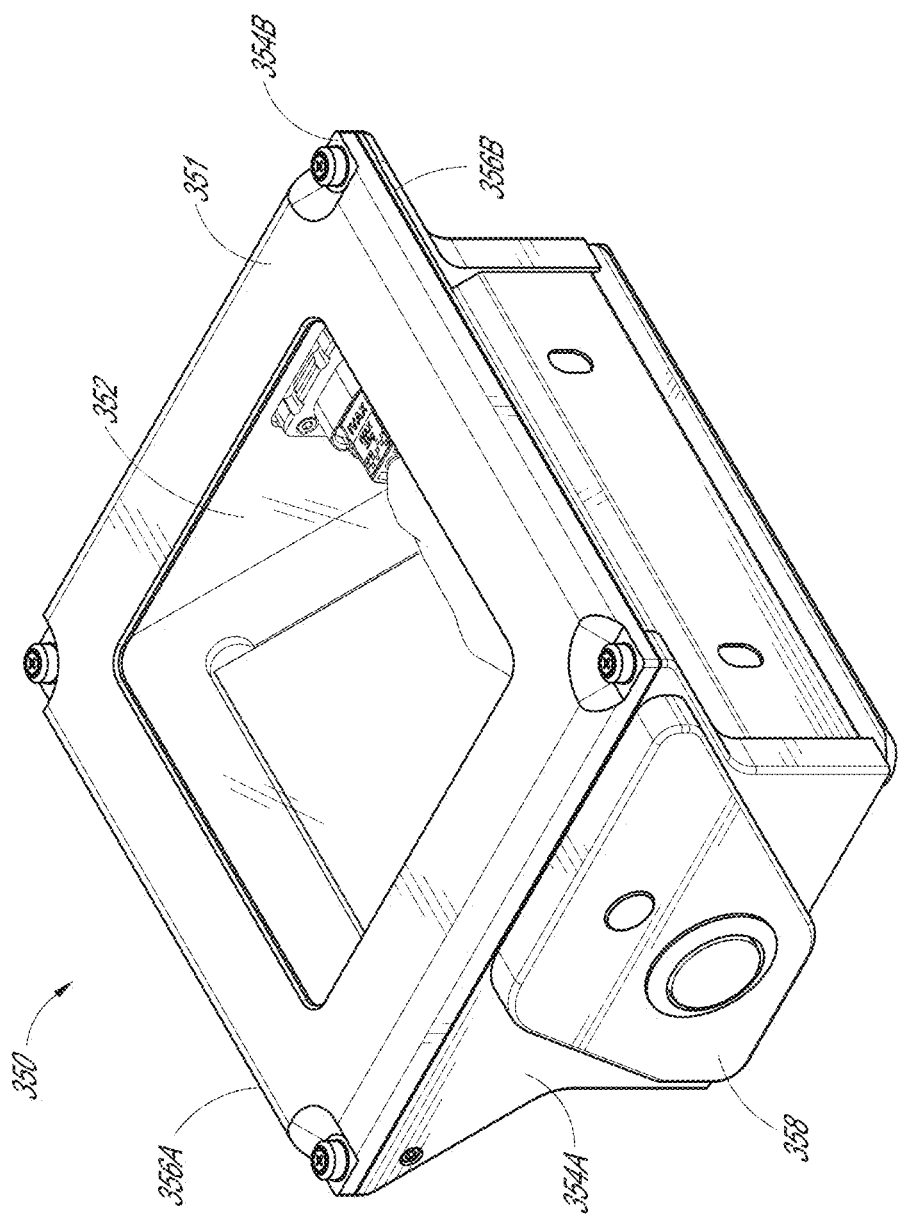

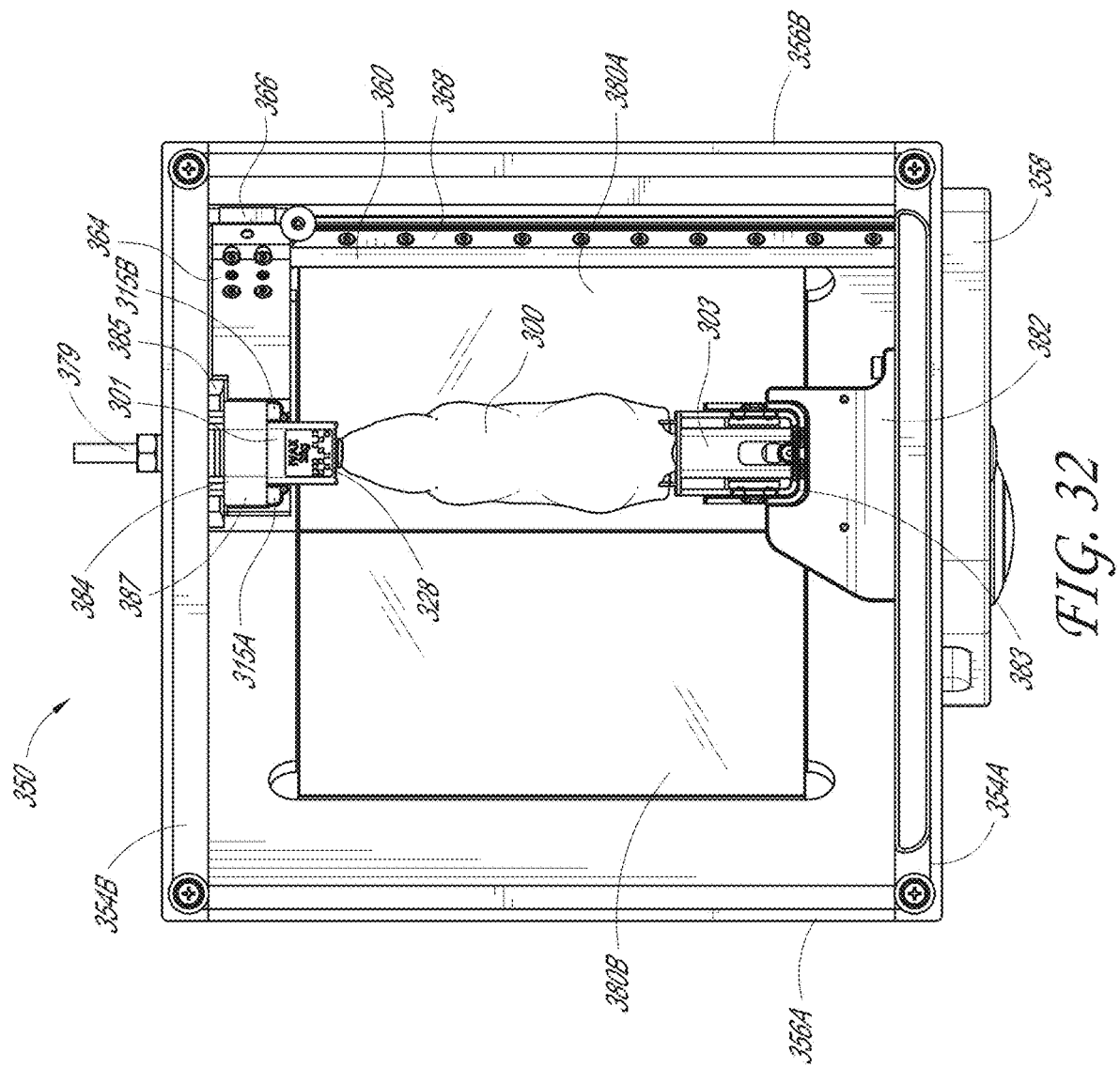

SYSTEMS AND METHODS FOR IMAGING OF AN ANATOMICAL STRUCTURE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority to U.S. Provisional Application No. 62/350,129 filed on Jun. 14, 2016, U.S. Provisional Application No. 62/350,128 filed on Jun. 14, 2016, U.S. Provisional Application No. 62/382,654 filed on Sep. 1, 2016, and U.S. Provisional Application No. 62/382,679 filed on Sep. 1, 2016, each of which is hereby incorporated by reference in its entirety.

BACKGROUND

The present disclosure relates to imaging methods and apparatuses, and more particularly, in some arrangements, relates to methods and apparatus for imaging of an anatomical structure.

DESCRIPTION OF THE RELATED ART

Preclinical imaging is a modality for studying diseases and pathological dysfunction in small animal models. Preclinical imaging can allow for research into human diseases using animal models, such as rodents, and can further be used to develop new therapeutics. Traditional preclinical imaging data, such as that produced by two dimensional ("2D") bioluminescence imaging ("BLI") or three dimensional ("3D") bioluminescence tomography ("BLT"), is prone to large variability in interpretation due to user-subjectivity in image data processing, e.g., manual selection of regions-of-interest, variability in animal pose and surface rendering, ad-hoc tomographic reconstruction parameters or unknown image noise.

There is a need to address reproducibility in preclinical studies for translational research given increasing drug development costs and high clinical failure rates. BLI is, however, mostly limited to planar imaging of light intensities at the surface of the animal, where light intensity emitted from within has been attenuated by the thickness of tissue it traversed. Due to depth-dependence of surficial light intensity, BLI cannot provide any quantitative information originating from a deep-seated target inside a mouse model such as the actual amount of luminescent bacteria, tumor cells, or stem cells growing or migrating inside the animal.

Region- or volume-of-interest analysis can be used for quantifying bacterial burden, proliferation, and therapeutic efficacy. However, BLI reliance on the operator-dependent visual inspection of a region-of-interest (ROI) for drawing conclusions about study outcome can be difficult to reproduce by an independent external review. Image analysis of large-scale data sets and cross-examination between images of different animals and time points using different mathematical tools can also be prohibited due to a number of procedural and computational constraints such as the planar surface images without depth information; differences in individual animal pose, animal size, and camera view; and the limited local computational resources. Furthermore, the automatic co-registration of optical images to an accurate anatomical map is completely missing without the use of an additional imaging modality like CT or MRI with some elaborate and/or resource intensive co-registration.

Bacterial infections are an exemplary case for demonstrating limitations of BLI in preclinical research and drug development. Bacterial infections impose a costly health burden worldwide which is compounded by the alarming increase of multi-drug resistant (MDR) Gram-negative bacteria, and many of these infections are in the urogenital tract. Urogenital tract infections (UTI) are typically caused by a Gram-negative *E. coli* (75-90%) that afflicts more than 250 million adults and children worldwide each year. According to the CDC, 75% of hospital acquired UTIs were associated with the placement of a urinary catheter where 15-25% of all hospitalized patients receive a urinary catheter. However, pharmaceutical companies tasked with developing the next class of antibiotics and new antimicrobial catheters do not have the tools to monitor bacterial infections quantitatively in real-time in animal models of infection. Thus many novel antibiotics are stalled at the preclinical stage. Compounding this public health problem is that the number of novel antibiotics has been on the decline over the past decade. An essential step in the development of novel antibiotics to combat urinary MDR *E. coli* is done in small animal models with bioluminescent bacteria.

However, the state of the art optical imaging systems can only output qualitative data with limited data points and, thus, cannot assess the efficacy in vivo with quantitative information. Therefore, there is an urgent unmet need for in vivo monitoring of the spatial and temporal dynamics of bacterial organ burden in response to therapeutic intervention.

Current BLI methods are based on the assumption that the measured light intensity at the tissue surface (photons s-1 cm-2) directly correlates to the colony forming units (CFU) of bacteria inside an organ. However, light is strongly attenuated by tissue and the measured signal may be dependent on: (i) the unknown spatial location of bacteria; (ii) the heterogeneous optical tissue properties; and (iii) the animal's size, pose, and shape. Bioluminescence tomography uses models of light attenuation in tissue from bioluminescent source to the animal surface to correct for this decrease in brightness, which can be orders of magnitude. Commercially available bioluminescence tomography software assumes homogeneous tissue properties and a diffusion model of photon propagation. The commercial software analysis requires tedious, subjective user-input for multiple steps of the tomographic process that give rise to inconsistent reconstructions with the same mouse image data set. Commercial 3D bioluminescence reconstructions may therefore be prone to variability in reconstruction intensity and reconstruction distribution width, due to user-subjectivity in image data processing. Furthermore, after optical images have been acquired, the investigator visually inspects the optical image of each individual animal and manually selects a regions-of-interest (ROI) and determines some measure of the photon count within the ROI. This process is not only subject to interpretation of results depending on the investigator's visual observation but also on the animal's pose and size. Additionally, image and reconstruction noise properties are not established in bioluminescence tomography, rendering regions-/volumes-of-interest analysis prone to bias and error. Longitudinal study evaluation with error-prone reconstructions further reduces the study robustness and reliability. Moreover, an anatomical reference that determines the actual site of infection inside the animal is completely missing.

Considering the current limitations of BLI for spatiotemporal imaging, automated and quantitative analysis of imaging results across different animals and study points has not been feasible yet.

Furthermore, cross-comparison of 2D and 3D image data for different study time points or between different animals can be cumbersome based on variability in the sizes and poses of animals and because image pixels may not be consistently co-aligned with an animal's tissue surface.

U.S. Patent Publication No. 2015/0012224, which is hereby incorporated by reference herein in its entirety, discloses an optically transparent body-shape-conforming animal mold, which can constrain an animal model to a defined spatial position while the animal model is imaged. As described in U.S. Patent Publication No. 2015/0012224, when used with mice, a digital mouse atlas can provide an anatomical reference to the imaged animal and the animal mold can facilitate spatially aligning the imaged animal and the mouse atlas. The information from the imaged animal and the mouse atlas can then be used to provide quantitative information regarding the imaged mouse. While the methods and systems of U.S. Patent Publication No. 2015/0012224 are useful for BLI and/or BLT, there is a general desire to improve the accuracy and ease of use of the methods and systems described therein.

SUMMARY

The systems, methods, and devices of the disclosure each have several innovative aspects, no single one of which is solely responsible for the desirable attributes disclosed herein.

In one innovative aspect, an apparatus for housing an animal for optical imaging is provided. The apparatus can include a top section configured to encapsulate at least part of an animal, the mold piece including one or more hinge connections; and a bottom section configured to encapsulate at least part of an animal, the bottom section including one or more hinge connections configured to engage the one or more hinge connections of the top section, wherein when the one or more hinge connections of the top section connect with the one or more hinge connections of the bottom section, the top section and bottom section define an inner cavity configured to encapsulate the animal, and one or more openings configured to receive a gas from a gas supply, the one or more openings being positioned so that gas from the gas supply can permeate the inner cavity.

In another innovative aspect, an apparatus for housing an animal for optical imaging is provided. The apparatus can include a top section configured to encapsulate at least part of an animal, the top section including a first end and a second end and a bottom section configured to encapsulate at least part of an animal, the bottom section including a first end and a second end, wherein the first end of the top section is movably secured to the first end of the bottom section, such that the top section and bottom section are movable between an open position and a closed position, and wherein the second end of the top section and the second end of the bottom section are configured to detachably engage one another, wherein when the second end of the first mold piece and the second end of the bottom section are detachably engaged, the top section and bottom section define an inner cavity configured to encapsulate the animal.

In a further innovative aspect, an assembly for optical imaging of a plurality of animals is provided. The assembly can include a holder configured to secure a plurality of molds, each mold configured to encapsulate an animal and a docking interface configured to engage the holder, wherein the docking interface is further configured to allow for 180° rotation.

In a further innovative aspect, a method for collecting optical imaging data for an animal is provided. The method can include placing an animal into an interior chamber of a body conforming animal mold, supplying an anesthetic from a gas supply to the interior chamber, and performing optical imaging of the animal in the mold.

In a further innovative aspect, an assembly for optical imaging of an animal is provided. The assembly can include a plurality of optical mirrors and a channel configured to receive an animal mold configured to encapsulate an animal. The animal mold can include a top section, a bottom section, and a hinge including a pivot axis, wherein the top section and the bottom section are configured to rotate about the pivot axis between a closed position and an open position.

In a further innovative aspect, an assembly for optical imaging of a plurality of animals is provided. The assembly can include a plurality of molds, each mold configured to encapsulate an animal, a holder configured to secure the plurality of molds; and a gas supply in communication with the plurality of molds, wherein the gas supply is configured to direct gas to the plurality of molds.

In a further innovative aspect, a method for collecting optical imaging data for an animal is provided. The method can include placing an animal into an optical imaging assembly, performing optical imaging of the animal, detecting a computer readable label in an optical image captured by the optical imaging assembly, and extracting data from the computer readable label.

In a further innovative aspect, a system for providing reproducible imaging results indicative of an in vivo experimental result is provided, the imaging results provided for presentation via a display unit. The system includes an image receiver configured to receive first image data and second image data. The system includes a data store including position definitions, wherein a first position definition identifies, for an animal subject imaged at a first time while in a first position, a first location for an anatomical feature at the first time. A second position definition identifies, for an animal subject imaged at a second time while in a second position, a second location for the anatomical feature at the second time. The system also includes a position detector configured to identify the first position definition for processing the first image data based on the first image data, and to identify second position definition for processing the second image data, based on the second image data. The system also includes an image processor. The image processor is configured to receive a processing protocol identifying a comparison for image data and an associated result based thereon. The comparison indicates one or more locations of input image data to compare and how to compare the indicated input image data. The associated result indicates an output imaging result to provide for a comparison result. The image processor is also configured to extract a portion of the first image data from the first location of the first image data and to extract a portion of the second image data from the second location of the second image data. The image processor is further configured to generate comparison data according to the comparison identified in the processing protocol using image data at the one or more locations identified by the comparison from the first portion of the first image data and the second portion of the second image data. The image processor is also configured to generate an imaging result according to the processing protocol using the comparison data and cause presentation of the imaging result via the display unit.

In some implementations of the system, the image receiver may be configured to receive the first image data from a first sensing device. In some implementations of the system, the image receiver may be configured to receive the second image data from a second sensing device.

The animal subject imaged by the system at the first time may an animal test subject, and the animal subject imaged at the second time is the animal test subject. That is, the system may image same animal subject at the first and second time. In some implementations, the system may image different animal subjects at the first time and the second time.

In some implementations of the system the first location may identify one or more pixel locations for the anatomical feature shown in the first image data. In such implementations, the second location may identify one or more pixel locations for the anatomical feature shown in the second image data. The one or more locations of input image data indicated by the comparison may include one or more pixel locations. In implementations where the location data identifies pixels, the image processor may be configured to generate the imaging result by comparing, using the processing protocol, first pixel values at the one or more pixel locations of the anatomical feature shown in the first image data with second pixel values at the one or more pixel locations of the anatomical feature shown in the second image data.

In some implementations, the first location may identify one or more voxel locations for the anatomical feature shown in the first image data and the second location may identify one or more voxel locations for the anatomical feature shown in the second image data. In such implementations, the one or more locations of input image data indicated by the comparison includes one or more voxel locations. In implementations where the location data identifies voxels, the image processor may be configured to generate the imaging result by comparing, using the processing protocol, first voxel values at the one or more voxel locations of the anatomical feature shown in the first image data with second voxel values at the one or more voxel locations of the anatomical feature shown in the second image data.

In some implementations, the position detector may be configured to identify the first position by detecting, within the first image data, an identifiable mark associated with the first position. The identifiable mark may be identified on a mold in which the animal subject was placed to capture the first image data. In such implementations, at least a portion of the mold is shown in the first image data.

An imaging controller may be included in some implementations of the system. The imaging controller may be configured to receive, from an imaging device, information at a third time identifying the animal subject to be imaged. The imaging controller may be further configured to identify a third position definition for the animal subject, the third position definition identifying, for the animal subject imaged while in a third position, a third location for the anatomical feature. The imaging controller may further generate a configuration command indicating sensor parameters for imaging the animal subject using the third position definition and the processing protocol and, in some implementations, transmit the configuration command to the imaging device. The imaging controller may be further configured to generate the configuration command using imaging results for the animal subject stored before the third time.

In a further innovative aspect, an image processing system is provided. The image processing system includes an image receiver configured to receive image data from an imaging device. The image processing system includes a data store including a plurality of position definitions. A position definition identifies, for a given subject imaged while in a position, a location for an anatomical feature of the subject. The image processing system includes a position detector configured to identify, using the image data received from the imaging device, the position definition for the image data. The image processing system further includes an image processor configured to generate an imaging result using a portion of the image data at the location for the anatomical feature identified by the position definition.

In some implementations of the image processing system, the first location may identify one or more pixel locations for the anatomical feature shown in the first image data and the second location identifies one or more pixel locations for the anatomical feature shown in the second image data. In such implementations, the one or more locations of input image data indicated by the comparison include one or more pixel locations. Where the location data is identified using pixels, the image processor may be configured to generate the imaging result by comparing, using the processing protocol, first pixel values at the one or more pixel locations of the anatomical feature shown in the first image data with second pixel values at the one or more pixel locations of the anatomical feature shown in the second image data.

In some implementations of the image processing system, the first location may identify one or more voxel locations for the anatomical feature shown in the first image data and the second location identifies one or more voxel locations for the anatomical feature shown in the second image data. In such implementations, the one or more locations of input image data indicated by the comparison include one or more voxel locations. Where the location data is identified using voxels, the image processor may be configured to generate the imaging result by comparing, using the processing protocol, first voxel values at the one or more voxel locations of the anatomical feature shown in the first image data with second voxel values at the one or more voxel locations of the anatomical feature shown in the second image data.

The position detector included in some implementations of the image processing system may be configured to identify the first position by detecting, within the first image data, an identifiable mark associated with the first position. For example, the identifiable mark may be identified on a positioning assembly in which the subject was placed to capture the first image data, at least a portion of the positioning assembly being shown in the first image data.

In a further innovative aspect, a computer implemented method is provided. The method includes receiving position definitions, wherein a position definition identifies, for a given subject imaged while in a position, a location for an anatomical feature of the subject. The method also includes receiving image data from an imaging device. The method further includes identifying, using the image data received from the imaging device, the position definition for the image data. The method also includes generating an imaging result using a portion of the image data at the location for the anatomical feature identified by the position definition.

BRIEF DESCRIPTION OF THE DRAWINGS

Embodiments of various inventive features will now be described with reference to the following drawings.

Throughout the drawings, reference numbers may be reused to indicate correspondence between referenced elements. The drawings are provided to illustrate example embodiments described herein and are not intended to limit the scope of the disclosure.

FIG. 11B depicts a perspective view of a gantry in a closed position in accordance with an illustrative embodiment.

FIG. 31 depicts a perspective view of a gantry in a closed position in accordance with an illustrative embodiment.

FIG. 32 depicts a top view of the gantry of FIG. 31 having several components removed in accordance with an illustrative embodiment.

DETAILED DESCRIPTION

Figure 1A:
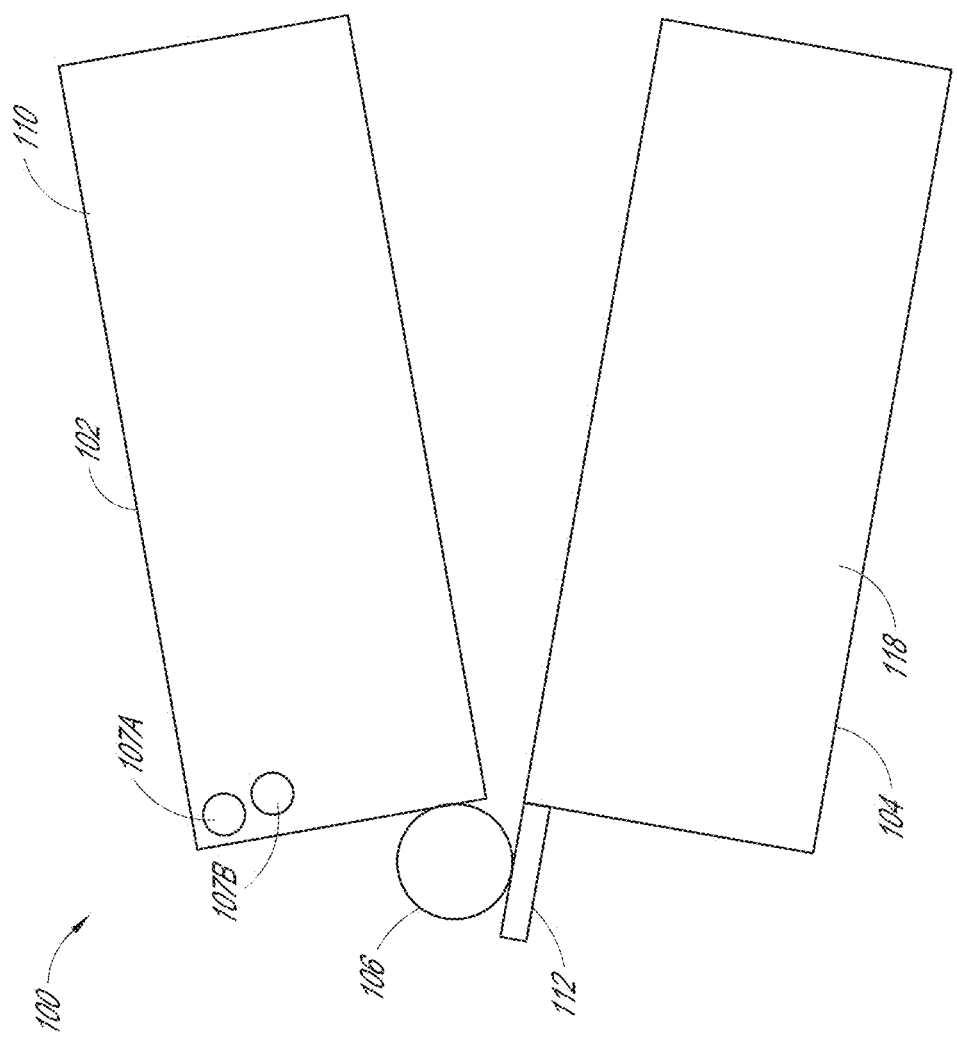
FIG. 1A depicts a schematic view of an animal mold in an open position in accordance with an illustrative embodiment.

The present disclosure includes systems and methods for imaging of an anatomical structure such as an animal and in some embodiments a small animal such as a mouse. The systems and methods of some embodiments are particularly useful for optical imaging such as, for example, bioluminescence imaging ("BLI") or three dimensional ("3D") bioluminescence tomography ("BLT"). However, some features and advantages of embodiments disclosed herein may also have utility in non-optical imaging such as, for example, computed tomography ("CT") scans, positron emission tomography ("PET"), single photon emission counting tomography ("SPECT"), or magnetic resonance imaging ("MRI").

Some aspects of the present disclosure include an animal mold, which can have a shape and size to hold an animal in an immobilized and geometrically defined position. The animal mold can be made of a solid material that is optically transparent or at least partially transparent to facilitate optical imaging of an animal within the interior of the animal mold. In non-optical imaging embodiments, the mold can be mode of a material that is transparent to the imaging modality and does not cause any signal distortions. The animal mold can be made from a variety of techniques such as thermo vacuum molding, injection molding, and 3D stereo lithography. Accordingly, while the term "mold" can sometimes imply something that is formed in a mold or formed from molten state, the term as used in herein is not limited to such a definition or such a technique for forming the animal mold. In some arrangements, the animal mold can be configured so that the mold slightly compresses an animal in the interior of the mold so that the animal is at least partially restrained and so that the outer surface of the animal body can contact the interior surface of the animal mold. In some arrangements, the animal mold can provide a constant spatial frame of reference across different animals, and can also provide a consistent surface for camera detection points. Thus, in some embodiments, the body of the animal mold can provide infrastructure for software analysis of animal data taking advantage of a mutual three dimensional grid between data sets recorded using the body of the animal mold. The mutual spatial coordinate frame provided by the animal mold can further allow for cross-comparison of different preclinical imaging modalities including BLI, BLT, fluorescence, PET, SPECT, MRI, and CT in some arrangements. The animal mold can also be used in the creation of an organ probability map, a statistical representation of the average spatial organ distribution of a given pool of animals with the same body weight while taking the biological variation across different animals into account. The body conforming animal molds can come in a variety of sizes for different weights, sizes, sexes and strains of animals. The mutual spatial coordinate frame provided by the animal mold, as well as an organ probability map, can allow for analysis of imaging data across animals of different weights, sizes, sexes and strains.

In some embodiments, optical imaging is performed on an animal mold using a gantry. A gantry can include multiple optical mirrors to provide for simultaneous imaging of multiple different views of an animal within an animal mold.

In some embodiments, optical imaging is performed simultaneously on a plurality of animal molds. A plurality of animal molds can be secured to a single holder for optical imaging. In some embodiments, the holder can be configured to rotate about an axis to allow for imaging of different views of an animal within an animal mold. In some embodiments, the holder may be a gantry.

Some of the features described allow cross-correlation of image data. In a laboratory setting, experimental data may be obtained in the form of images of a subject. Many experiments are performed on living subjects whom are likely to move and grow over time. As discussed above, this presents a challenge in performing quantitative, reproducible experiments using such image data. Furthermore, image data may be collected from different sensors (e.g., modalities). For example, a protocol may call for BLI and MRI data collection. Cross-correlating the data collected across modalities introduces a further challenged when performing quantitative, reproducible experiments. The image data may include non-optical image data such as positron emission tomography (PET), magnetic resonance imaging (MRI), single-photon emission computed tomography (SPECT), or other nuclear imaging image data.

The cross-correlation features described may be implemented in an image processing device or system. One example implementation may include a hardware plugin unit for bioluminescence imaging, a cloud-based server using image data from the hardware plug in unit for image reconstruction and analysis, and a client-based data communication and pre-processing tool. Some implementations may run in a distributed environment (e.g., cloud computing service) for resource intensive computation tasks and automated analysis of large data sets. In an automated image data processing pipeline, the system may be configured to determine image noise and 3D reconstruction noise prior to receiving image data for analysis using clustering algorithms blinded to cohorts such as control and treatment arms.

Such implementations may afford non-limiting advantages such as increasing the productivity, transparency, and robustness of pre-clinical research and drug development and accelerating scientific discoveries by providing a robust, distributed, and dynamically configured image processing resources. By providing operator-friendly access to image processing resources and an automated workflow-based interface, investigators may carry out, speed up, and standardize many challenging image analysis and reconstruction tasks that are currently impossible or impractical due to the limitations of the existing BLI technology and/or the local computer hardware (e.g. within the lab, on the imaging device). Distributed computing services can be configured for high reliability, flexible scalability, and efficient allocation of a large pool of resources (e.g., memory, power, processor time, network bandwidth, etc.). In some implementations, the system may be accessed as a subscription service by users. The distributed service may be dynamically configured to process and cross-correlate images in a variety of formats, from a variety of imaging devices, and for a variety of experimental purposes such as bacterial infections, cancer, stem cell, and neurology research.

In some implementations, all or some of the features described may be implemented as an integrated hardware add-on or retrofit for commercial BLI systems. In a bioluminescence bacterial study, the system may be configured to calculate a spatial bacterial burden or density (CFU/mm3) distribution inside a living animal. The described features are a departure from current methods at least because: (i) they can quantitate in vivo bacterial organ burden in real-time; and (ii) reliably co-register it to an anatomical reference.

FIG. 1A depicts a schematic view of an animal mold 100 in accordance with an illustrative embodiment of the present disclosure. The animal mold 100 can include a top section 102 and a bottom section 104 The top section 102 can include an animal body conforming section 110, a hinge connection 106, and a pair of openings 107A and 107B. The bottom section 104 can include an animal body conforming section 118 and a corresponding hinge connection 112. The animal mold 100 is shown in an open position. The animal mold 100 can be generally shaped to conform to the body of an animal, such as a rodent, such that the animal mold 100 is generally body conforming to the animal.

The hinge connection 106 of the top section 102 can be engaged to the hinge connection 112 of the bottom section 104 such that the top section 102 can be rotated with respect to the bottom section 104. FIG. 1A depicts the animal mold 100 in an open position in which the body conforming section 110 is positioned apart from the body conforming section 118. The top section 102 can be configured to rotate away from the bottom section 104 so as to provide sufficient space to place an animal within the body conforming section 118 when in the open position. Openings 107A and 107B can be configured to receive gas from a gas supply (not shown). Gas received through the openings 107A and 107B can flow into the animal body conforming sections 110 and 118.

Figure 1B:
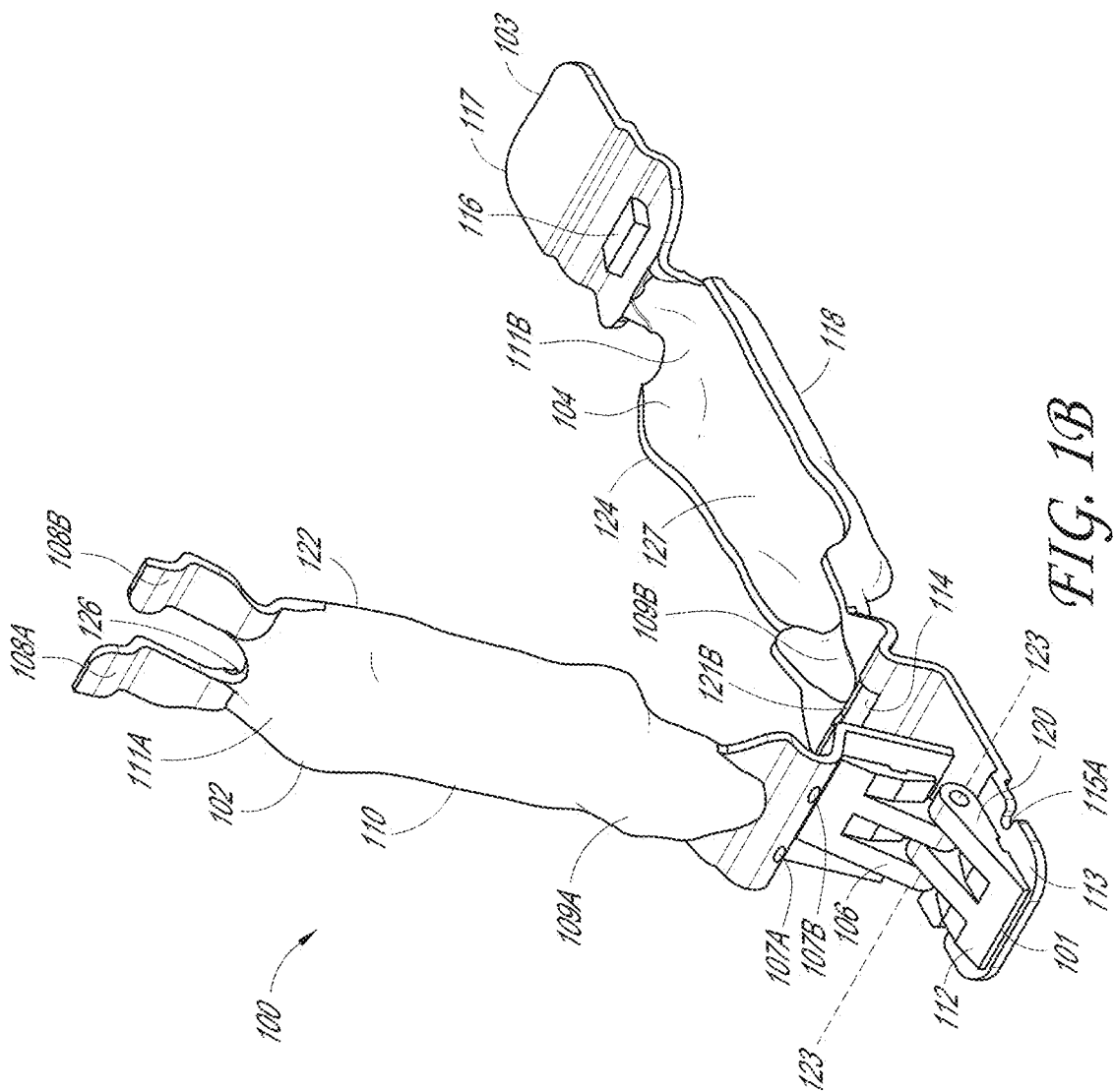
FIG. 1B depicts a perspective view of an animal mold in an open position in accordance with an illustrative embodiment.

FIG. 1B depicts a perspective view of the animal mold 100 in an open position in accordance with an illustrative embodiment of the present disclosure. In this embodiment, the animal mold 100 can be generally shaped to conform to the body of a rodent, such as a mouse, such that the animal mold is generally body conforming to the animal. The animal mold 100 includes a proximal end 101 and a distal end 103. The animal mold 100 can further includes the top section 102 and the bottom section 104. The top section 102 can include openings 107A and 107B, the hinge connection 106, locking arms 108, animal body conforming section 110, and an opening 126. The bottom section 104 can include the corresponding hinge connection 112, a front plate 113, a rear plate 117, a recessed section 114, a locking tab 116, and animal body conforming section 118.

As noted above, the animal mold 100 can be made of a solid material that is optically transparent or at least partially transparent to facilitate optical imaging of an animal within the interior of the animal mold 100. In non-optical imaging embodiments, the animal mold 100 can be mode of a material that is transparent and non-distorting to the imaging modality. The animal mold 100 can be configured so that the animal mold 100 slightly compresses an animal in the interior of the animal mold 100 so that the animal is at least partially restrained and so that the outer surface of the animal body can contact the interior surface of the animal mold 100. As will be explained below, in some arrangements, the animal mold 100 can provide a constant spatial frame of reference across different animals, and can also provide a consistent surface for camera detection points. The top and bottom sections 102, 104 of the animal mold 100 define a pre-defined interior surface 127, which can be correlated to a given animal (for example mouse) age, strain, sex and/or weight. As shown in FIG. 1, a set of molds can be provided that can correspond to different animal (for example mouse) age, strain, sex and/or weight categories. In this manner, the mold 100 can hold the animals in a fixed posture and provide a constant spatial frame of reference across different animals within a category, and can also provide a consistent surface for camera detection point.

The hinge connection 112 can be secured to the front plate 113 of the bottom section 104 at a front end of the animal mold 100. The front plate 113 can be configured to engage a support structure of an imaging apparatus, such as a gantry, in order to maintain the animal mold 100 in a consistent position for optical imaging. The front plate 113 can include openings 115A and 115B (not shown in FIG. 1). Openings 115A and 115B can be configured to receive gas supply components for providing a gas to the animal mold 100. The hinge connection 106 of the top section 102 can be engaged to the hinge connection 112 of the bottom section 104 so as to form a hinge 120 having a pivot axis along line 123-123. The top section 102 can be rotated with respect to the bottom section 104 along the pivot axis. FIG. 1B depicts the animal mold 100 in an open position in which the body conforming section 110 is positioned apart from the body conforming section 118. The top section 102 can be configured to rotate away from the bottom section 104 so as to provide sufficient space to place an animal within the body conforming section 118 when in the open position.

Although hinge connections 106 and 112 are described with respect to the embodiments shown in FIGS. 1A and 1B, it is contemplated that the top section 102 and bottom section 104 can be connected using any coupling technique known in the art. The top section 102 and bottom section 104 may include complementary interlocking components to facilitate coupling of the top section 102 to the bottom section 104. For example, the top section 102 and bottom section 104 may be coupled using a snap-fit or interference fit. The top section 102 and the bottom section 104 may be coupled by one or more fasteners.

The openings 107A and 107B can be positioned distally with respect to the hinge connection 106 and can be configured to receive a gas from a gas supply (not shown). A cranial portion 109A of the body conforming section 110 can be positioned distally from the openings 107A and 107B and at the proximal end of the body conforming section 110. Located between the openings 107A and 107B and the cranial portion 109A can be a passage 121A (not shown in FIG. 1) configured to allow gas to flow from the openings 107A and 107B to the cranial portion 109A when the animal mold 100 is in a closed position. The cranial portion 109A can be configured to receive a cranial segment of the animal. A caudal section 111A is positioned at the distal end of the body conforming section 110 can be configured to receive a caudal segment of the animal. The body conforming section 110 can be shaped and sized so as to generally conform to a dorsal segment of the animal. The body conforming section 110 further can include a bottom edge 122 configured to engage a top edge 124 of the body conforming section 118. The locking arms 108 can extend distally from the body conforming section 110.

Figure 2:
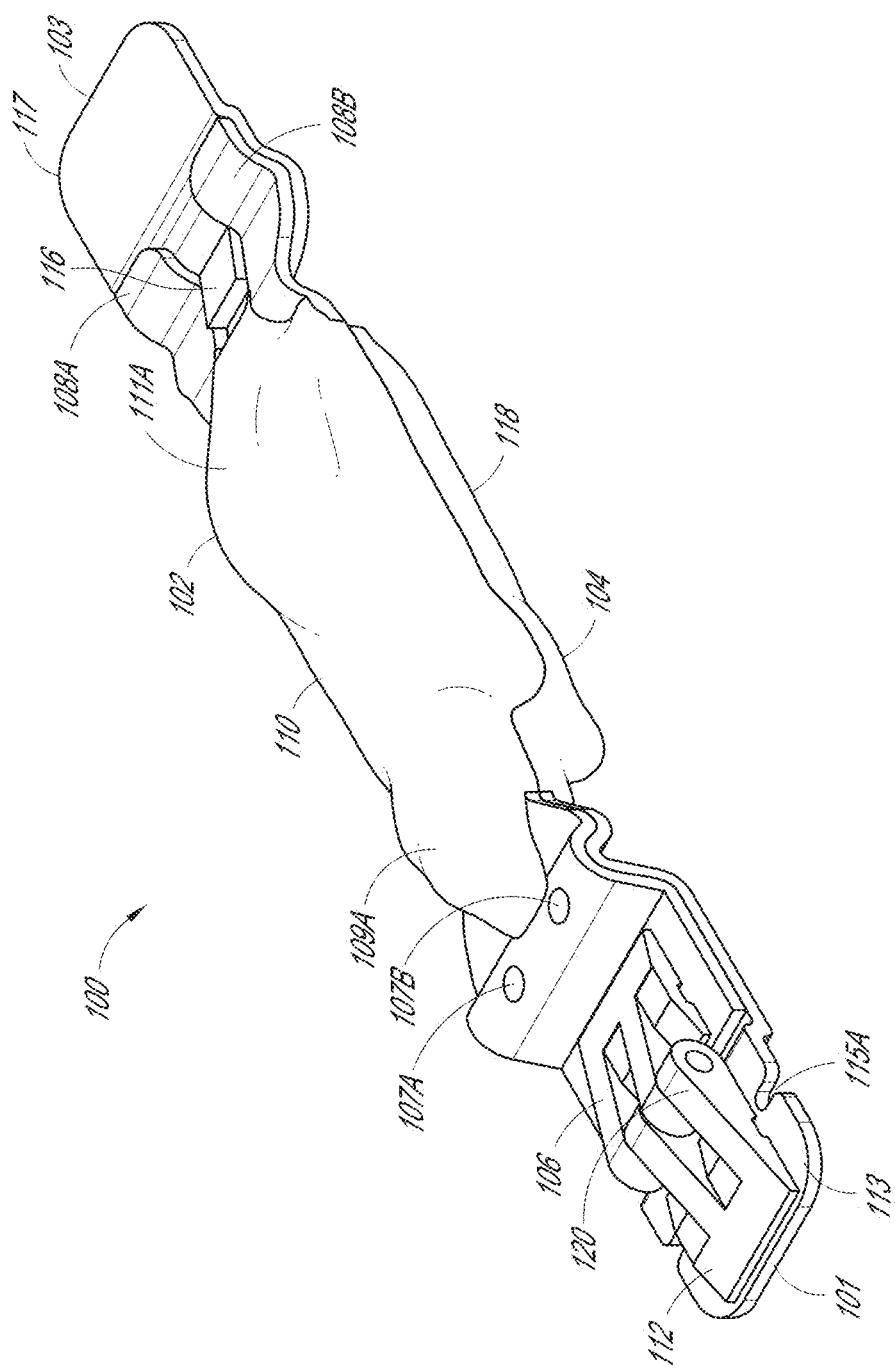
FIG. 2 depicts a perspective view of the animal mold of FIG. 1B in a closed position in accordance with an illustrative embodiment.

The recessed section 114 of the bottom section 104 can be positioned distally with respect to the hinge connection 112 and proximally adjacent to a cranial portion 109B of the body conforming section 118. The recessed portion 114 can also be positioned below the openings 107A and 107B, such that the recessed portion 114 can align with the openings 107A and 107B when the animal mold 100 is in a closed position, as shown in FIG. 2, so that gas received through the openings 107A and 107B can enter the recessed portion 114. A passage 121B can connect the recessed portion 114 to the cranial portion 109B to allow gas to flow from the recessed portion 114 to the cranial portion 109B when the animal mold 100 is in a closed position. The cranial portion 109B can be positioned at the proximal end of the body conforming section 118 and can be configured to receive a cranial segment of the animal. A caudal portion 11B of the body conforming section 118 can be positioned at the distal end of the body conforming section 118 and can be configured to receive a caudal segment of the animal. The body conforming section 118 can be shaped and sized so as to generally conform to a ventral segment of an animal. The locking tab 116 can be positioned distally from the body conforming section 118. The rear plate 117 can be located distally from the locking tab 116 at the distal end 103 of the bottom section 104.

FIG. 2 depicts a perspective view of the animal mold 100 of FIG. 1B in a closed position in accordance with an illustrative embodiment of the present disclosure. In the closed position, the locking arms 108A and 108B can detachably engage the locking tab 116. The locking arms 108A and 108B can engage the locking tab 116 through an interference fit. When in the closed position, the bottom edge 122 of the top section 102 can engage the top edge 124 of the bottom section 104 so as to form a substantially closed inner cavity for housing an animal.

Figure 3:
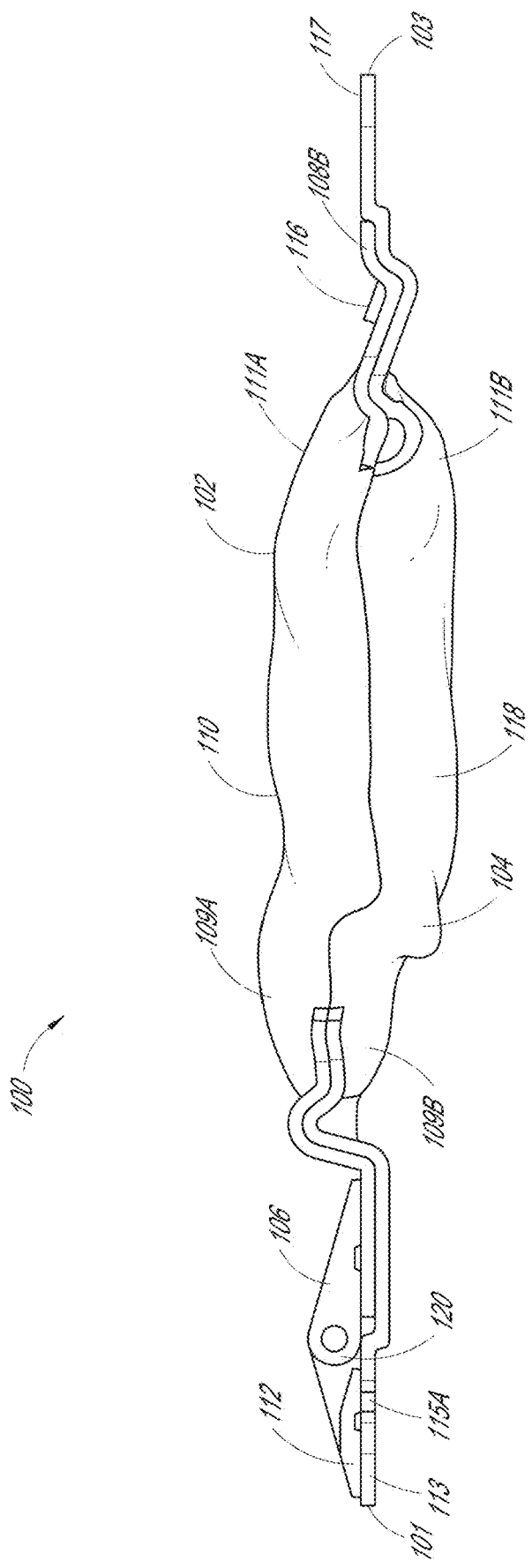
FIG. 3 depicts a side view the animal mold of FIG. 1B in a closed position in accordance with an illustrative embodiment.
Figure 4:
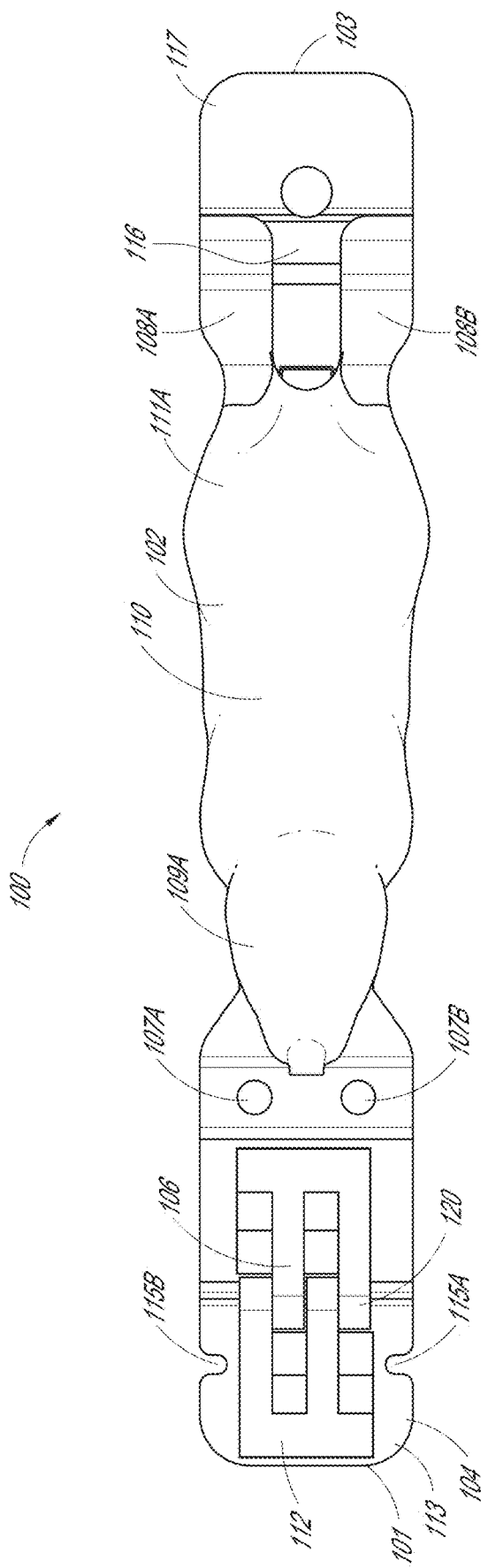
FIG. 4 depicts a top view of the animal mold of FIG. 1B in a closed position in accordance with an illustrative embodiment.
Figure 5:
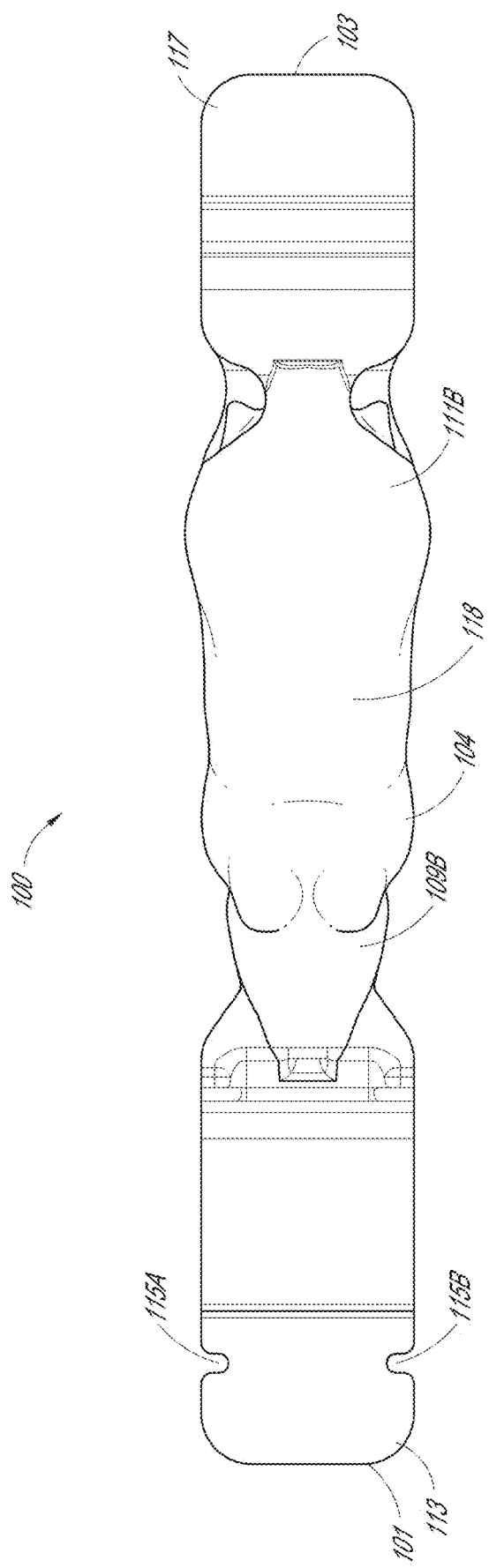
FIG. 5 depicts a bottom view of the animal mold of FIG. 1B in a closed position in accordance with an illustrative embodiment.
Figure 6:
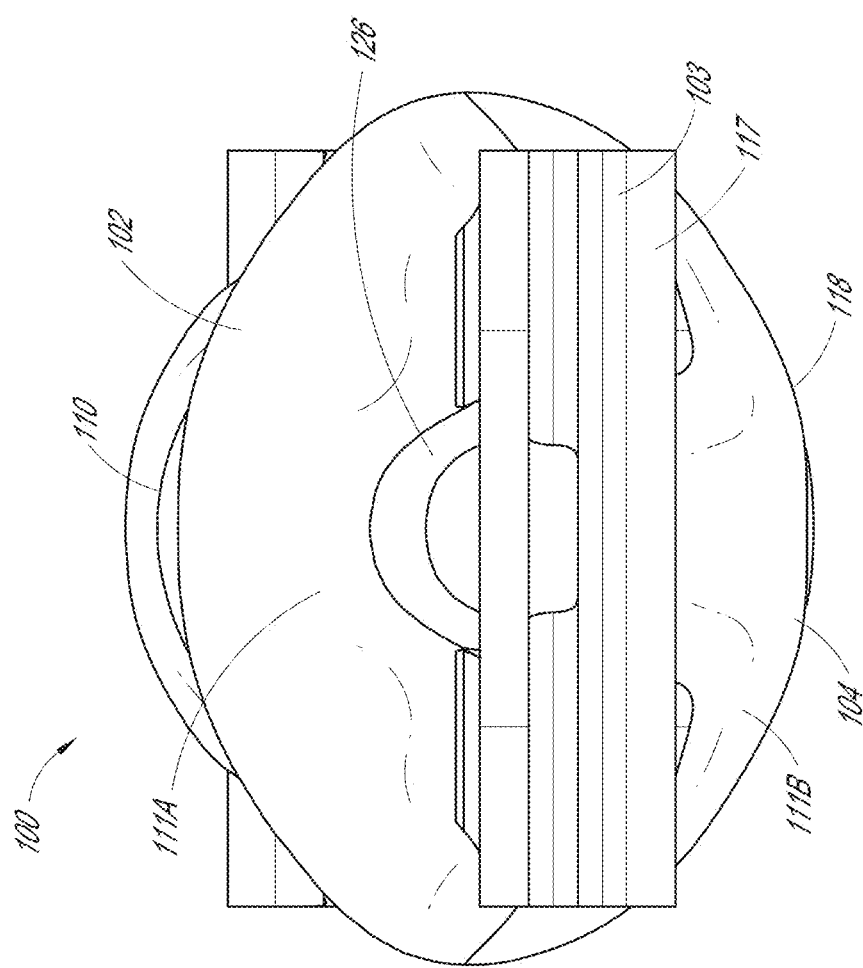
FIG. 6 depicts a rear view of the animal mold of FIG. 1B in a closed position in accordance with an illustrative embodiment.
Figure 7:
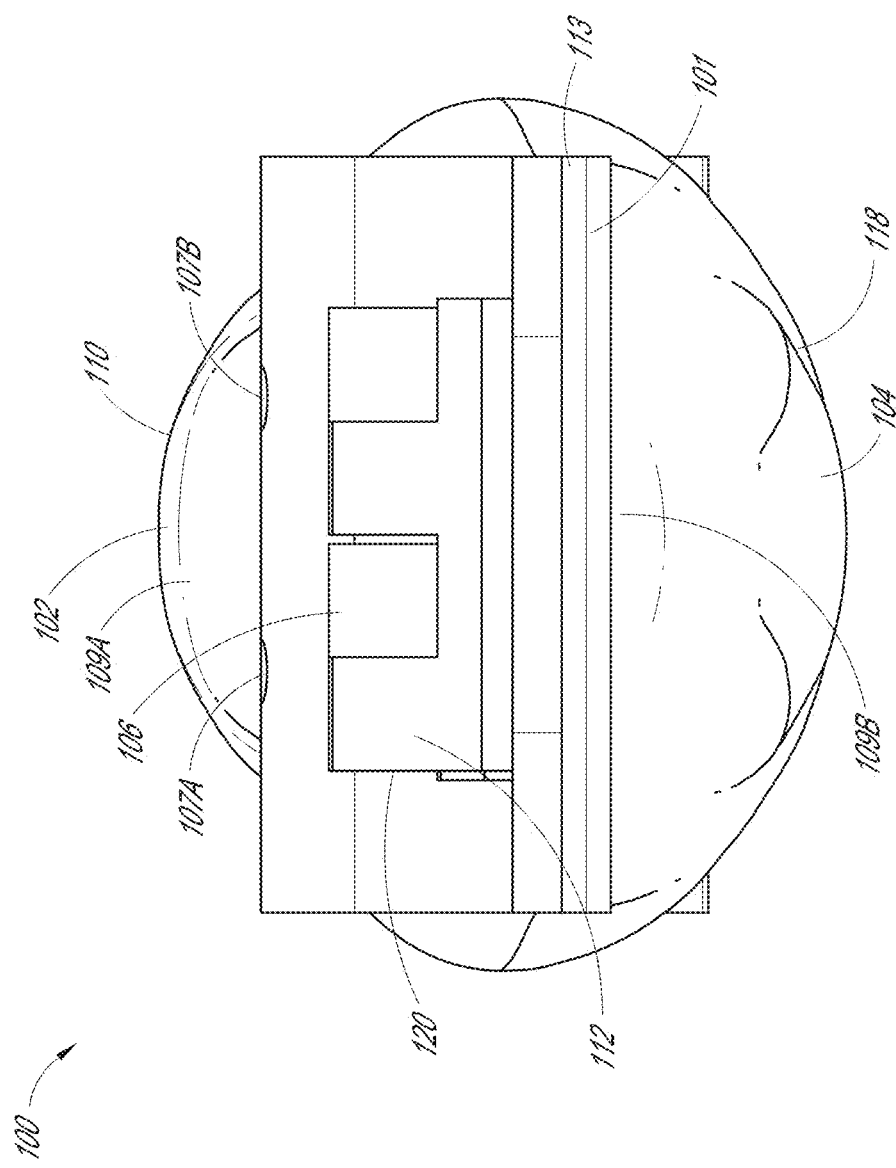
FIG. 7 depicts a front view of the animal mold of FIG. 1B a closed position in accordance with an illustrative embodiment.

FIG. 3 depicts a side view of the animal mold 100 of FIG. 1B in the closed position in accordance with an illustrative embodiment of the present disclosure. FIG. 4 depicts a top view of the animal mold 100 of FIG. 1B in the closed position in accordance with an illustrative embodiment of the present disclosure. FIG. 5 depicts a bottom view of animal mold 100 of FIG. 1B in the closed position in accordance with an illustrative embodiment of the present disclosure. FIG. 6 depicts a rear view of animal mold 100 in the closed position in accordance with an illustrative embodiment of the present disclosure. FIG. 7 depicts a front view of animal mold 100 of FIG. 1B in the closed position in accordance with an illustrative embodiment of the present disclosure.

Figure 8:
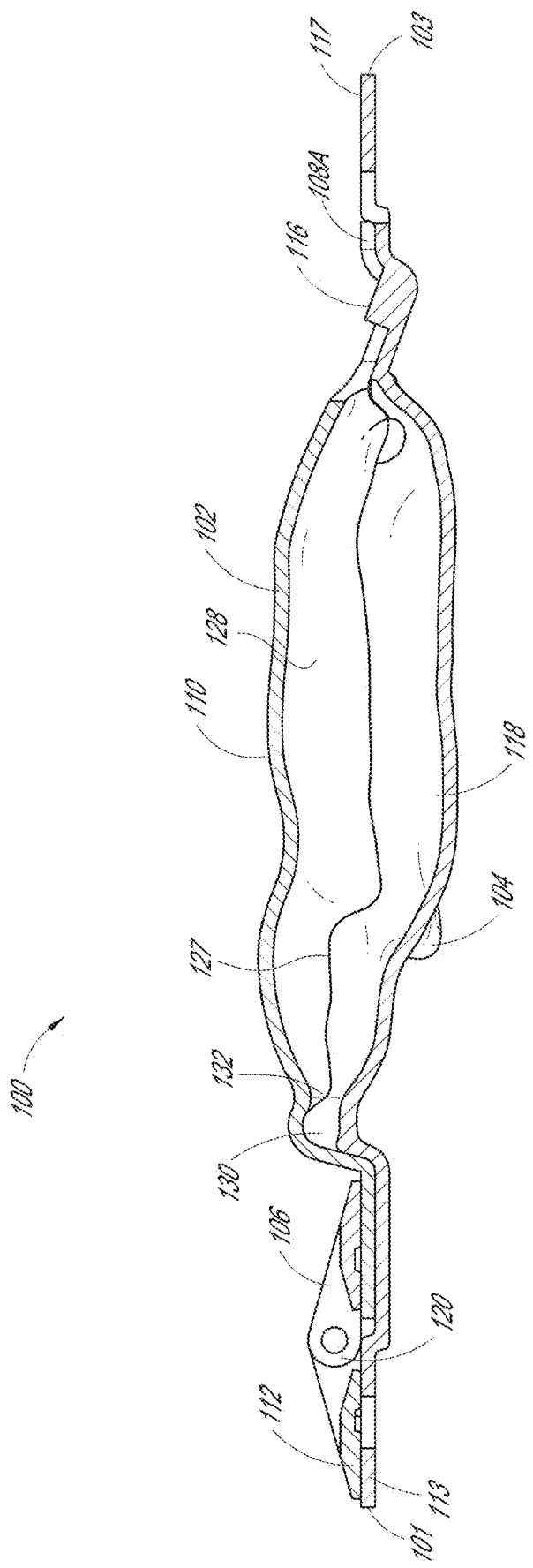
FIG. 8 depicts a cross sectional view of the animal mold of FIG. 1B in a closed position in accordance with an illustrative embodiment.

FIG. 8 depicts a cross sectional view of the animal mold 100 of FIG. 1B in the closed position in accordance with an illustrative embodiment of the present disclosure. When in the closed position, the top section 102 and bottom section 104 can define an inner cavity 128 for encapsulating an animal. FIG. 8 further shows a gas cavity 130 defined by the recessed section 114 and the portion of the upper section 102 including the openings 107A and 107B. FIG. 8 further shows a passage 132 defined by passage 121A of the upper section 102 and passage 121B of the lower section 104. The gas cavity 130 can be configured to receive gas such as an anesthetic from the openings 107A and 107B. The gas can then flow through the passage 132 into the inner cavity 128. Gas can leave the inner cavity 128 through the opening 126.

Figure 9:
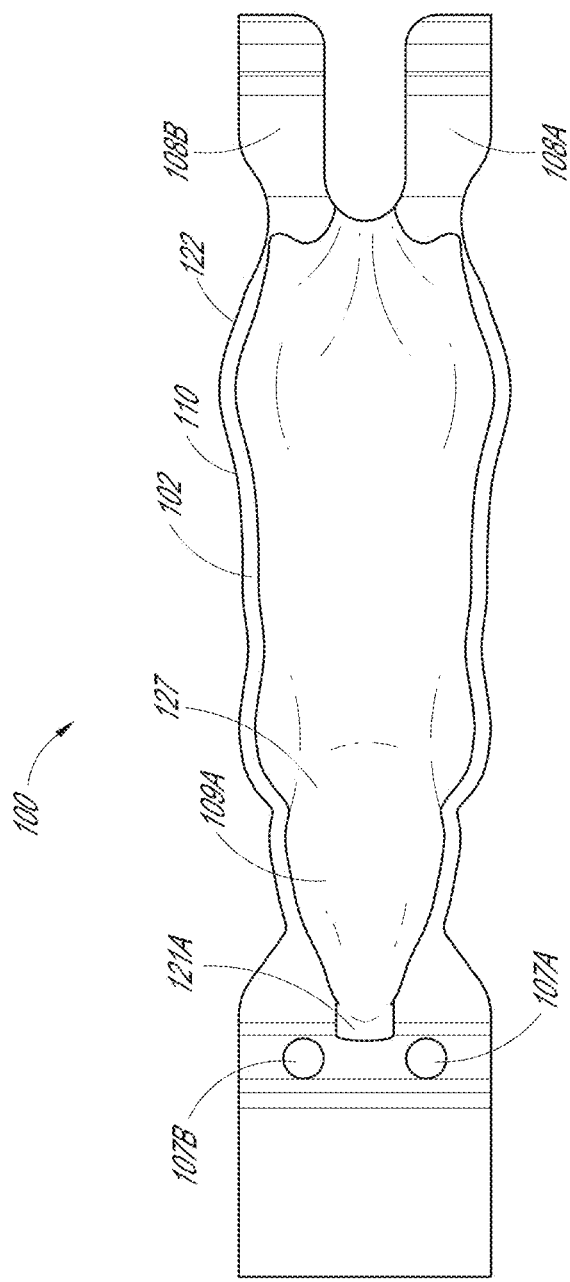
FIG. 9 depicts a bottom view of a top section of the animal mold of FIG. 1B mold in accordance with an illustrative embodiment.

FIG. 9 depicts a bottom view of the top section 102 of the animal mold 100 of FIG. 1B in accordance with an illustrative embodiment of the present disclosure.

Figure 10:
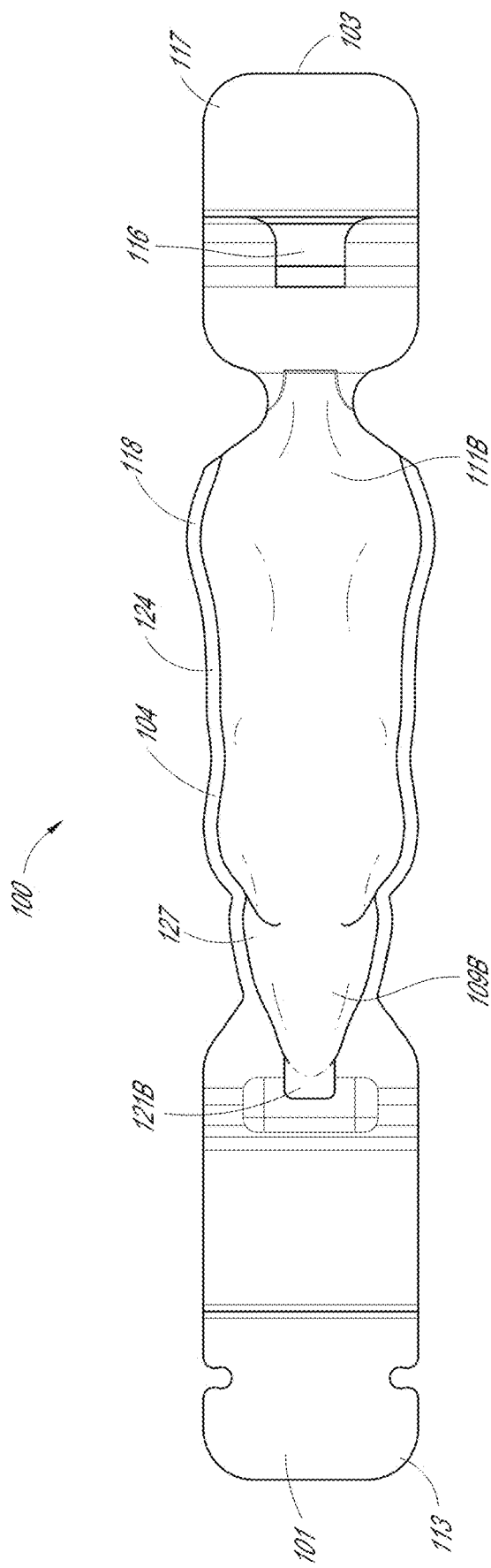
FIG. 10 depicts a top view of a bottom section of the animal mold of FIG. 1B in accordance with an illustrative embodiment.

FIG. 10 depicts a top view of the bottom section 104 of the animal mold 100 of FIG. 1B in accordance with an illustrative embodiment of the present disclosure.

Figure 11A:
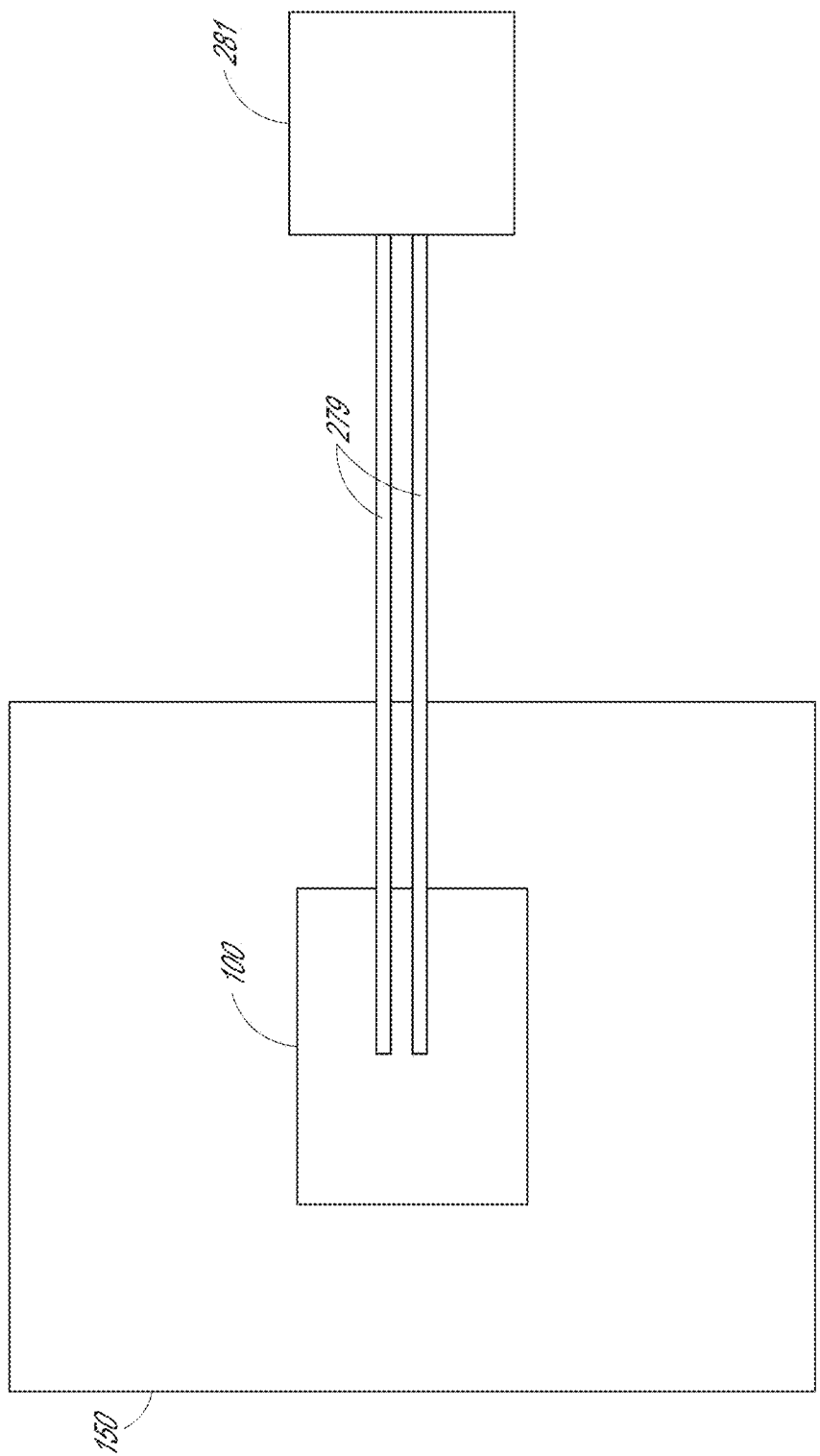
FIG. 11A depicts a schematic view of a gantry in accordance with an illustrative embodiment.

FIG. 11A depicts a schematic view of an illustrative embodiment of a gantry 150 in accordance with an illustrative embodiment of the present disclosure. As will be explained below, in the illustrative embodiment, the gantry 150 can include one or more mirrors that can aid in imaging an animal positioned within an animal mold that is supported by the gantry. The gantry 150 can allow for multi-orientation images. For example, the gantry 150 can allow for simultaneous imaging of dorsal, ventral, and side views of an animal in the animal mold 100. The gantry 150 can be configured to receive an animal mold, such as the animal mold 100 according to one of the embodiments described herein. The gantry 150 can further be configured to receive a gas from a gas supply 281. The gantry 150 can be connected to the gas supply 281 via supply pipes 279. In some embodiments, the animal mold 100 can be configured to receive gas flowing from the gas supply 281 to the gantry 150.

FIG. 11B depicts a perspective view of an illustrative embodiment of gantry 150 in a closed position in accordance with an illustrative embodiment of the present disclosure. As will be explained below, in the illustrative embodiment, the gantry 150 can include one or more mirrors that can aid in imaging an animal positioned within an animal mold that is supported by the gantry 150. In some embodiments, the gantry 150 can be configured to receive an animal mold, such as the animal mold 100 according to one of the embodiments described herein. The gantry can include a lid 151 having a window 152, front plate 154A, a back plate 154B, side walls 156A and 156B (not shown in FIG. 11B), and sliding handle 158, and a support plate 172.

Figure 12:
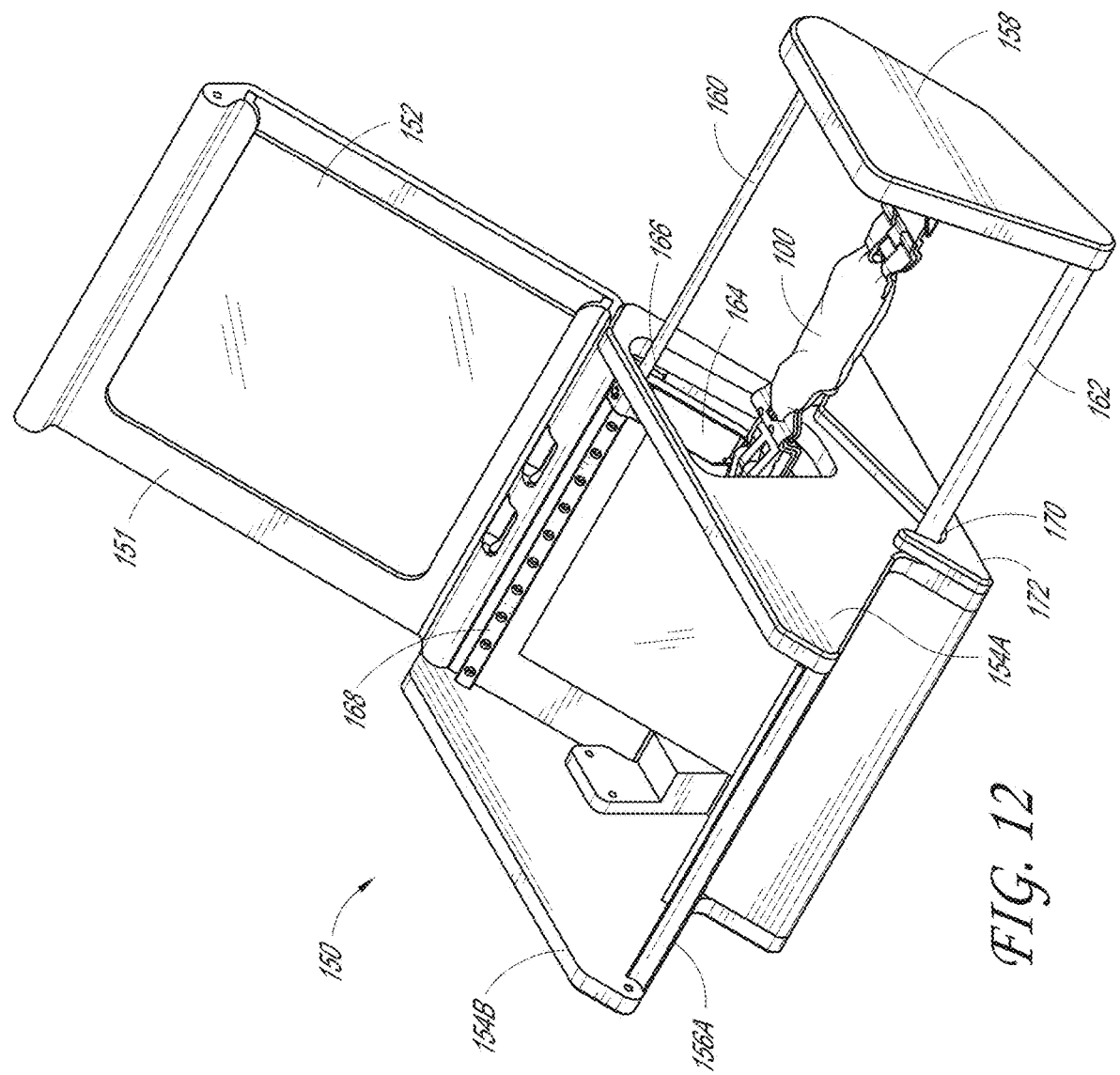
FIG. 12 depicts a perspective view of the gantry of FIG. 11B in an open position in accordance with an illustrative embodiment.

FIG. 12 depicts a perspective view of the gantry 150 in an open position in accordance with an illustrative embodiment of the present disclosure showing the animal mold 100 secured to the gantry 150. FIG. 12 further shows the sliding handle 158 extended distally from the front plate 154A. The sliding handle 158 can be configured to move proximally towards or distally from the front plate 154A in response to the application of manual force. The sliding handle 158 can be engaged to rods 160 and 162. Rod 160 is engaged to a mold support 164. The mold support 164 can be configured to engage the proximal end 101 of the bottom section 104 of the animal mold 100. The distal end 103 of the animal mold 100 can be further secured to an interior surface of the handle 158 through mold supports 182A and 182B (not shown in FIG. 12). The mold support 164 can be further configured to engage a sliding member 166. The sliding member 166 can be slidably mounted to a track 168 such that the handle 158 can translate from the open position shown in FIG. 12 to the closed position shown in FIG. 11B. Rod 162 can be configured to slide through an opening 170 within the front plate 154A. The support plate 172 can be secured to an exterior surface of the front plate 154A and can be positioned such that the rod 162 can contact a portion of the support plate 172 and slide across the support plate 172. The support plate 172 can provide structural support to the rod 162.

Figure 13:
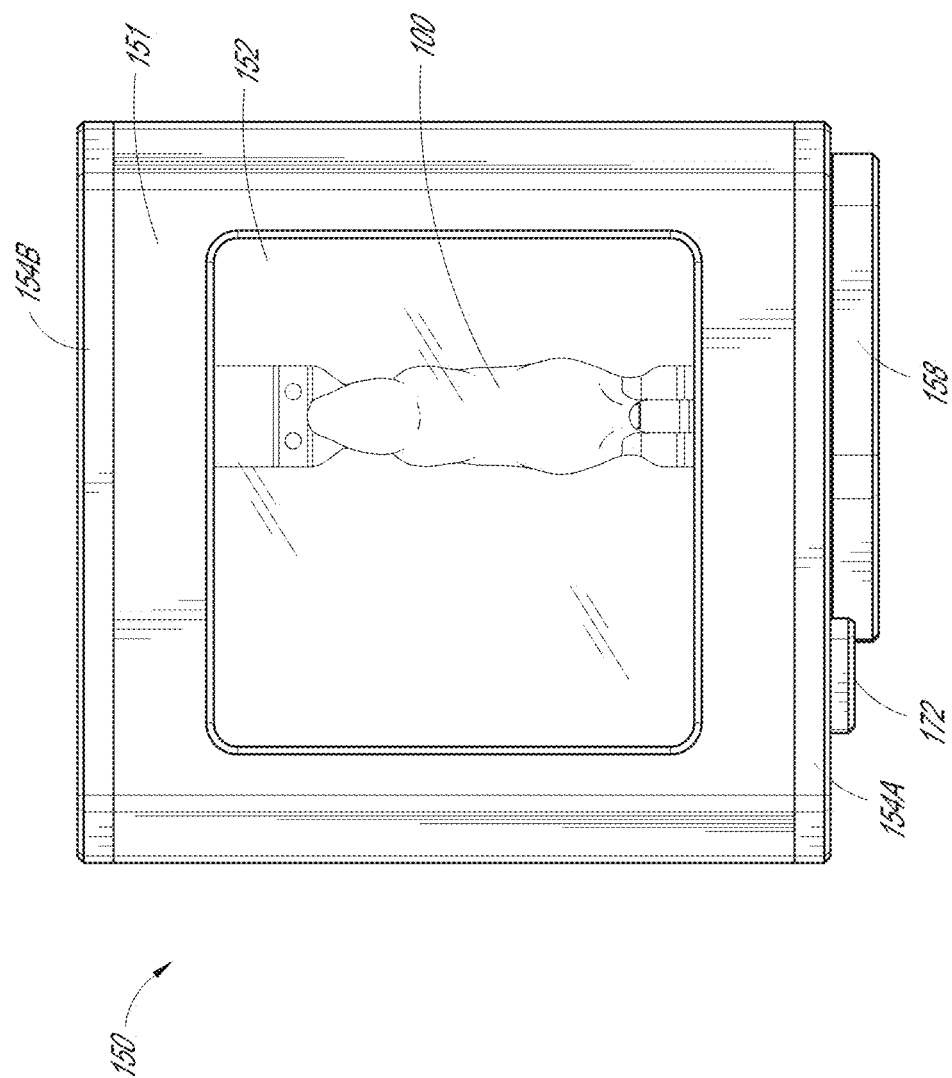
FIG. 13 depicts a top view of the gantry of FIG. 11B in a closed position in accordance with an illustrative embodiment.
Figure 14:
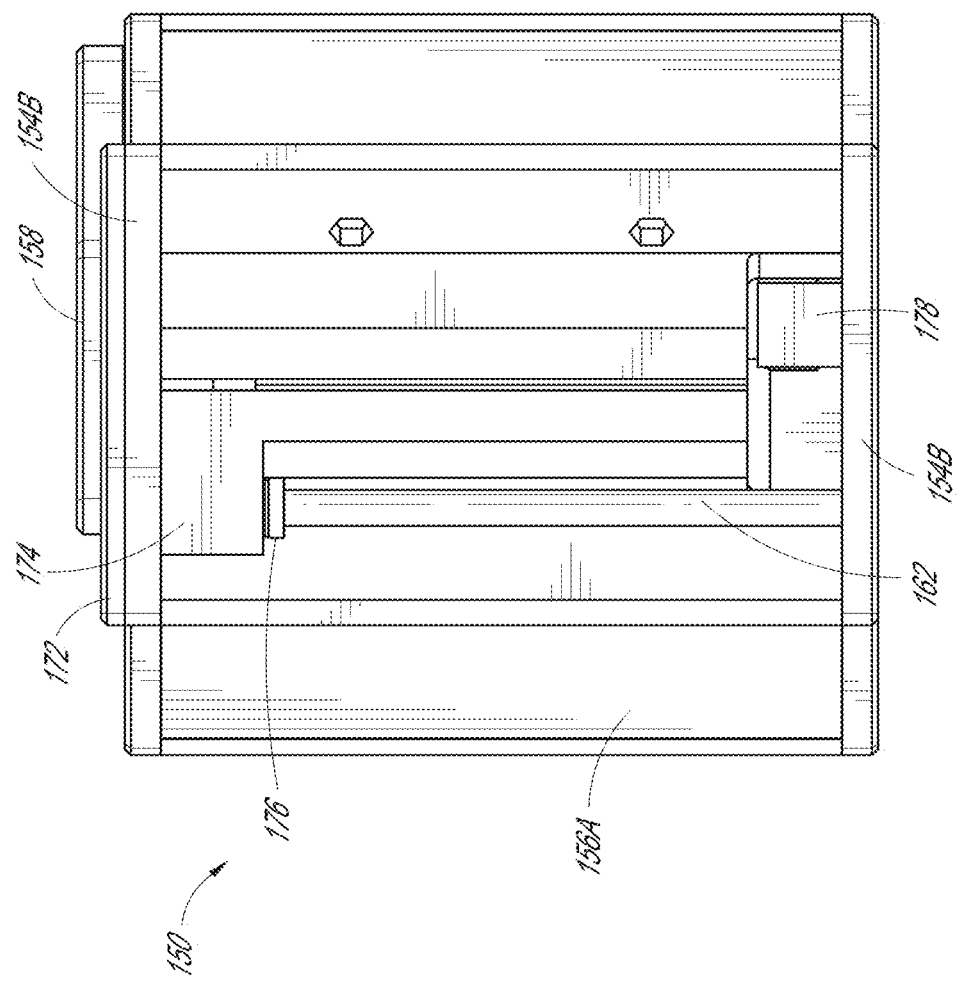
FIG. 14 depicts a bottom view of the gantry of FIG. 11B in a closed position in accordance with an illustrative embodiment.

FIG. 13 depicts a top view of the gantry 150 in a closed position in accordance with an illustrative embodiment of the present disclosure. FIG. 14 depicts a bottom view of the gantry 150 in a closed position in accordance with an illustrative embodiment of the present disclosure. The rod 162 is shown extending through a support section 174 of the side wall 156A and a sliding rail 176 for supporting the movement of the animal mold 100. When in the closed position, the rod 162 can be configured to be received in a recess (not shown) on an interior surface of the back plate 154B. FIG. 14 further shows a gas router 178 that can be to receive gas from a gas supply, such as gas supply 281 shown in FIG. 11A, and to provide gas to the animal mold 100.

Figure 15:
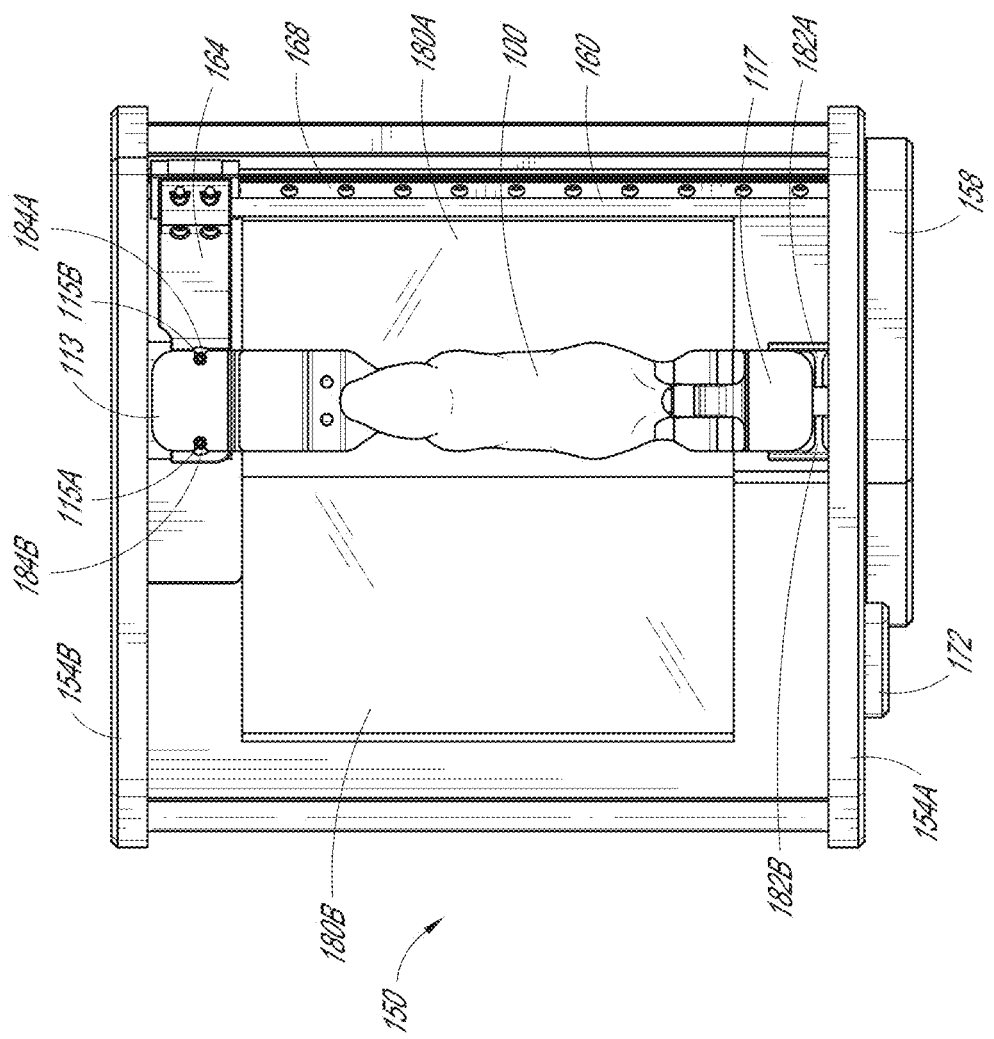
FIG. 15 depicts a top view of the gantry of FIG. 11B having several components removed in accordance with an illustrative embodiment.

FIG. 15 depicts a top view of the gantry 150 having the lid 151 and window 152 removed in accordance with an illustrative embodiment of the present disclosure. FIG. 15 shows mirrors 180A and 180B. The mirrors 180A and 180B can provide for simultaneous imaging of two different views of an animal within the animal mold 100. As depicted in FIG. 15, the front plate 113 at the proximal end 101 of the bottom section 104 can be received by the mold support 164. The mold support 164 further includes an inner cavity configured to receive a gas from gas router 178. FIG. 15 further shows gas channels 184A and 184B that can be configured to receive gas from the inner cavity of the mold support 164. In some embodiments, tubing can be connected to the gas channels 184A and 184B at one end and to the openings 107A and 107B of the animal mold 100 at the other end in order to supply gas to the openings. FIG. 15 further shows mold supports 182A and 182B extending from an interior surface of the handle 158. The mold supports 182A and 182B can be configured to receive the rear plate 117 of bottom section 104. Engagement of the animal mold 100 to the mold support 164 and mold supports 182A and 182B can fix the animal mold 100 in place within the gantry 150 when the gantry 150 is in the closed position to allow for optical imaging of an animal within the animal mold 100.

Figure 16:
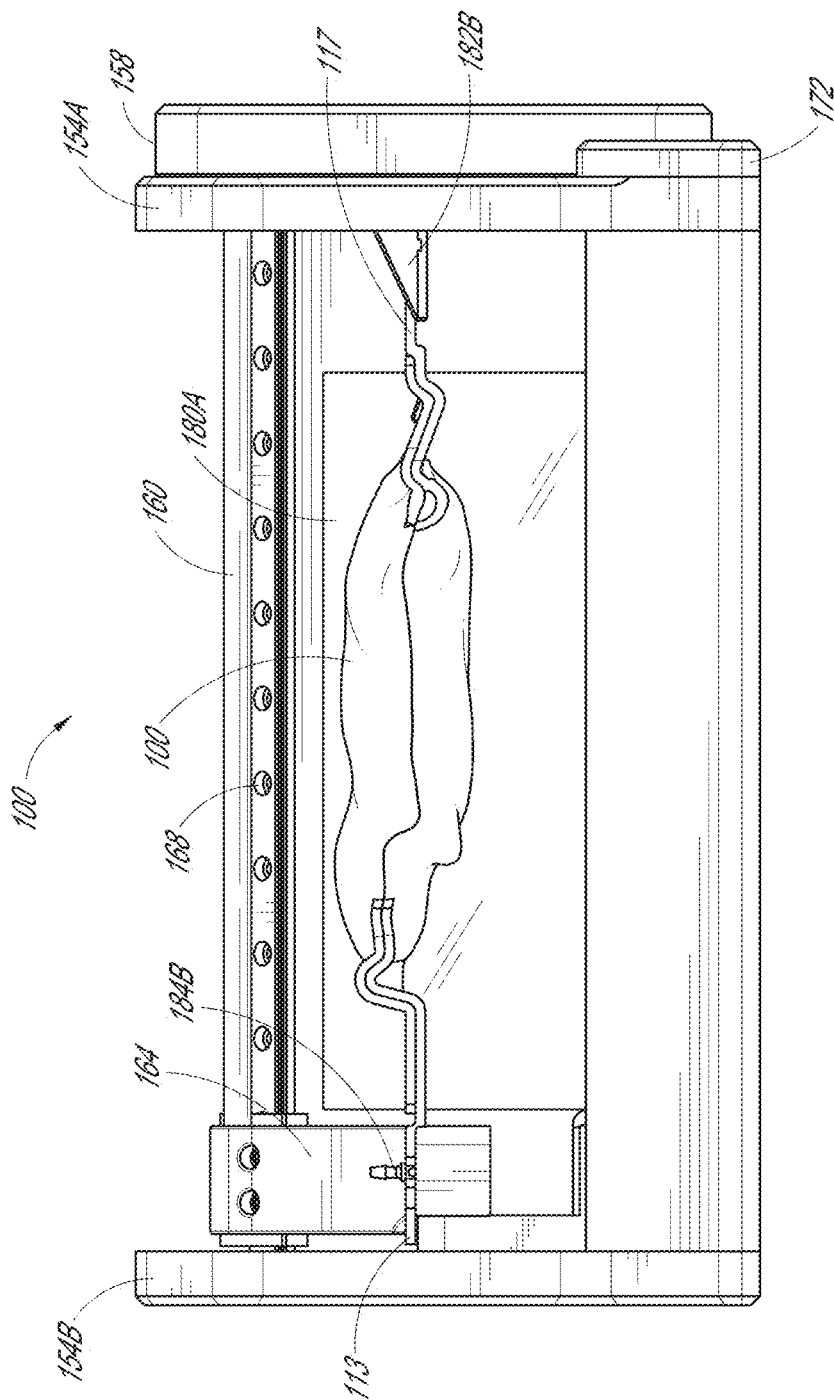
FIG. 16 shows a side view of the gantry of FIG. 11B having several components removed in accordance with an illustrative embodiment.
Figure 17:
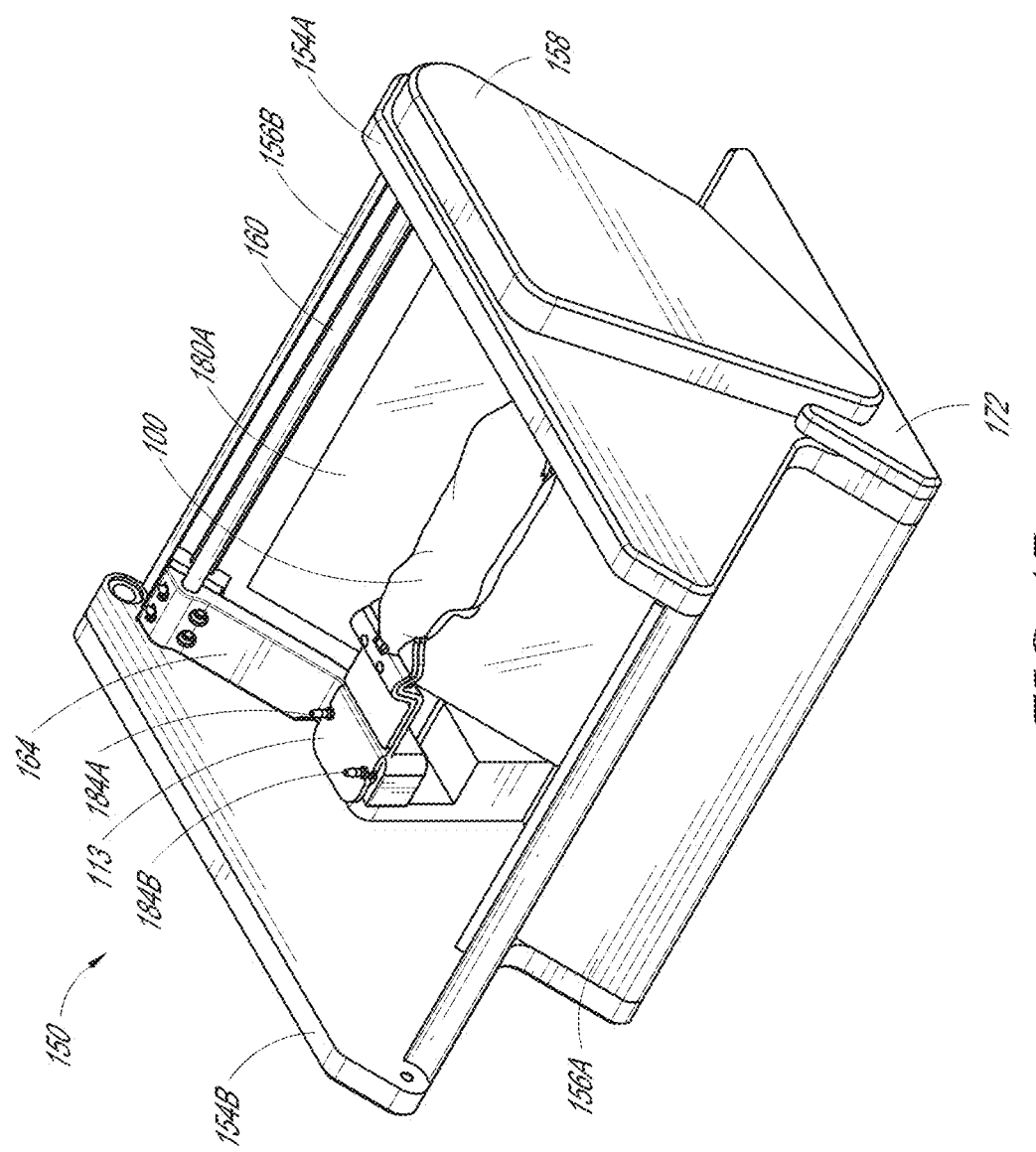
FIG. 17 shows a perspective view of the gantry of FIG. 11B having several components removed in accordance with an illustrative embodiment.
Figure 18:
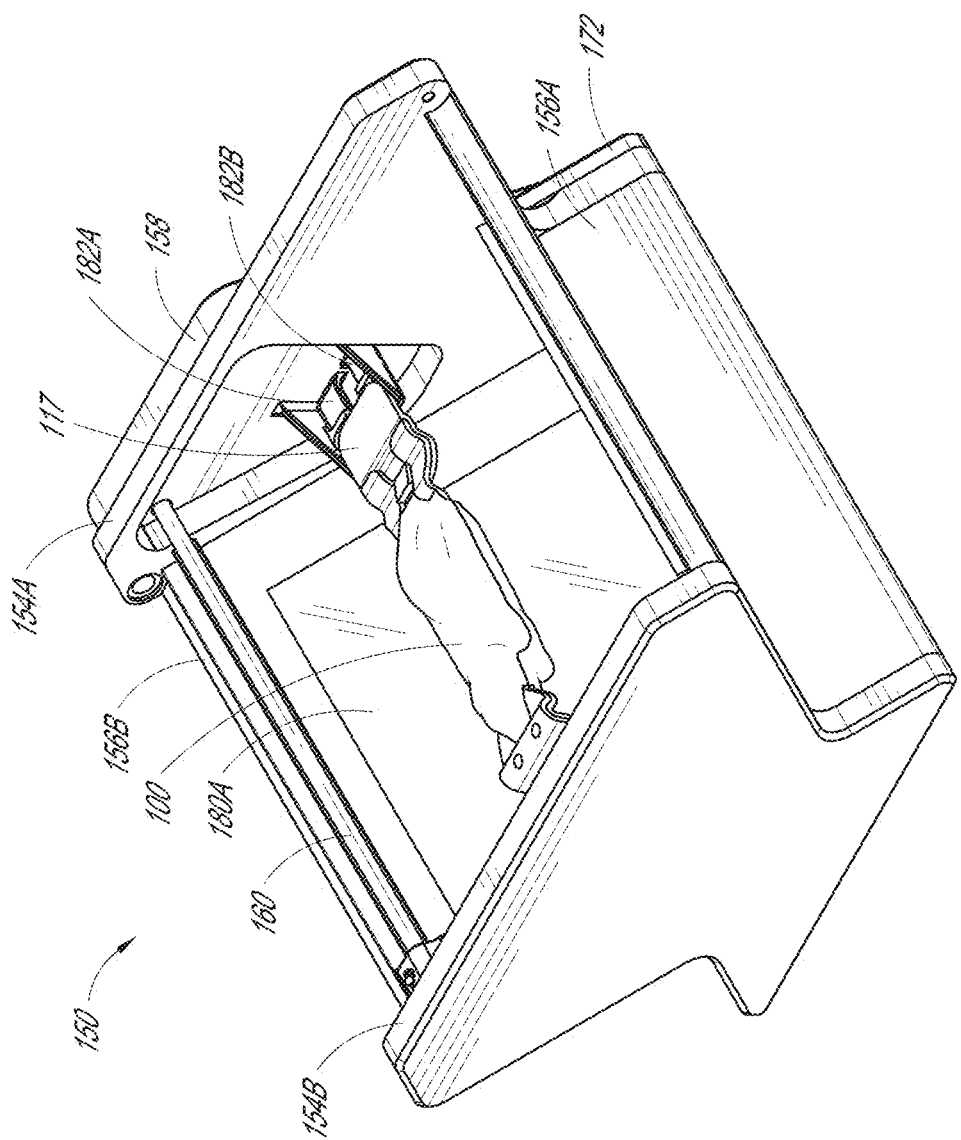
FIG. 18 depicts a perspective view of the gantry of FIG. 11B having several components removed in accordance with an illustrative embodiment.

FIG. 16 shows a side view of the gantry 150 having the side wall 156A, the mirror 180B, lid 151 and window 152 removed in accordance with an illustrative embodiment of the present disclosure. FIG. 17 shows a perspective view of the gantry 150 having lid 151 and window 152 removed in accordance with an illustrative embodiment of the present disclosure. FIG. 18 depicts a perspective view of the gantry 150 having lid 151 and window 152 removed in accordance with an illustrative embodiment of the present disclosure.

Figure 19:
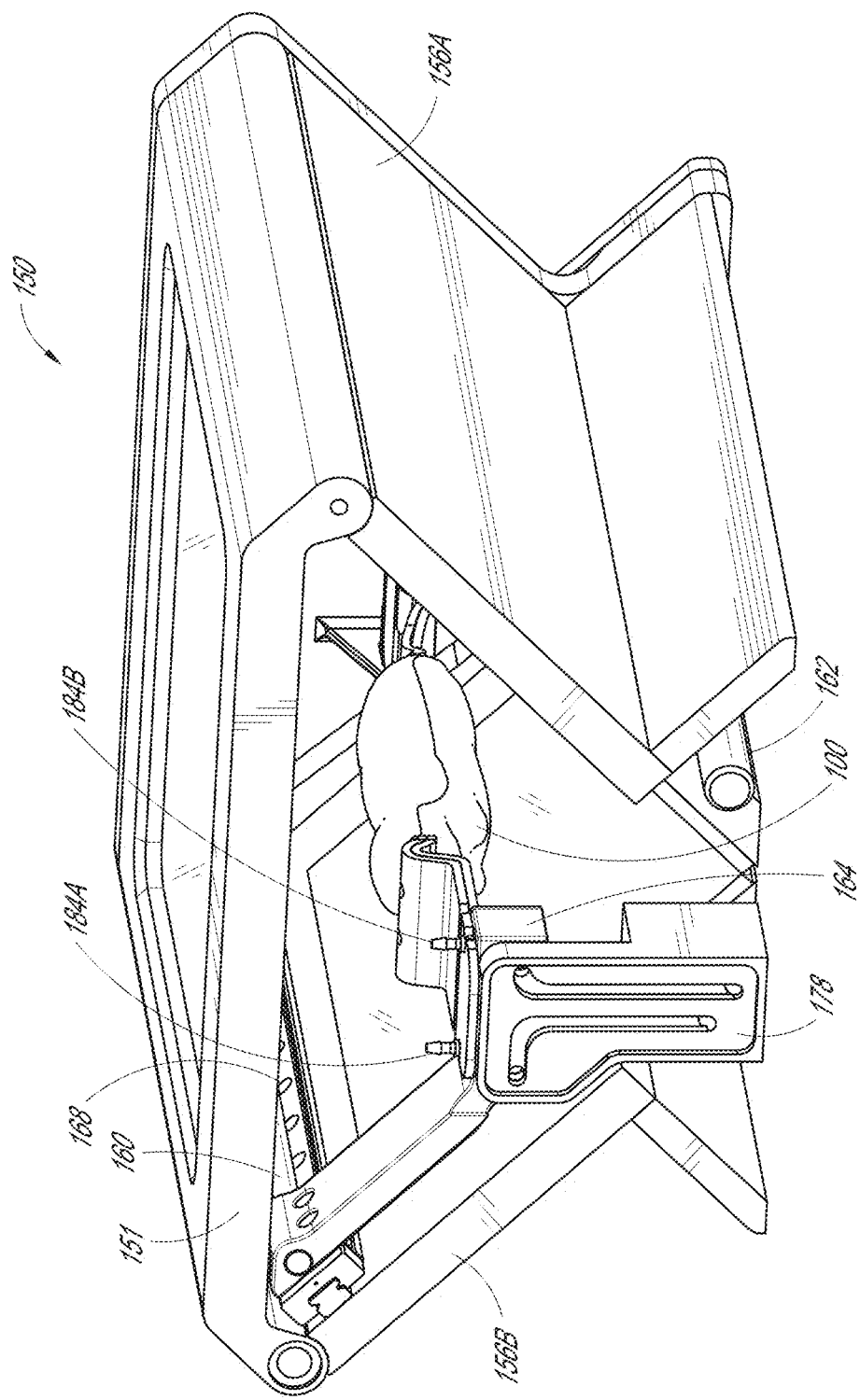
FIG. 19 depicts a perspective view of the gantry of FIG. 11B a closed position in accordance with an illustrative embodiment.

FIG. 19 depicts a perspective view of gantry 150 having back plate 154B removed in accordance with an illustrative embodiment of the present disclosure. As depicted in FIG. 19B, the gas router 178 is positioned to engage the mold support 164 in order to supply gas thereto. The gas router 178 can receive gas from gas supply 281 as shown in FIG. 11A.

Figure 20:
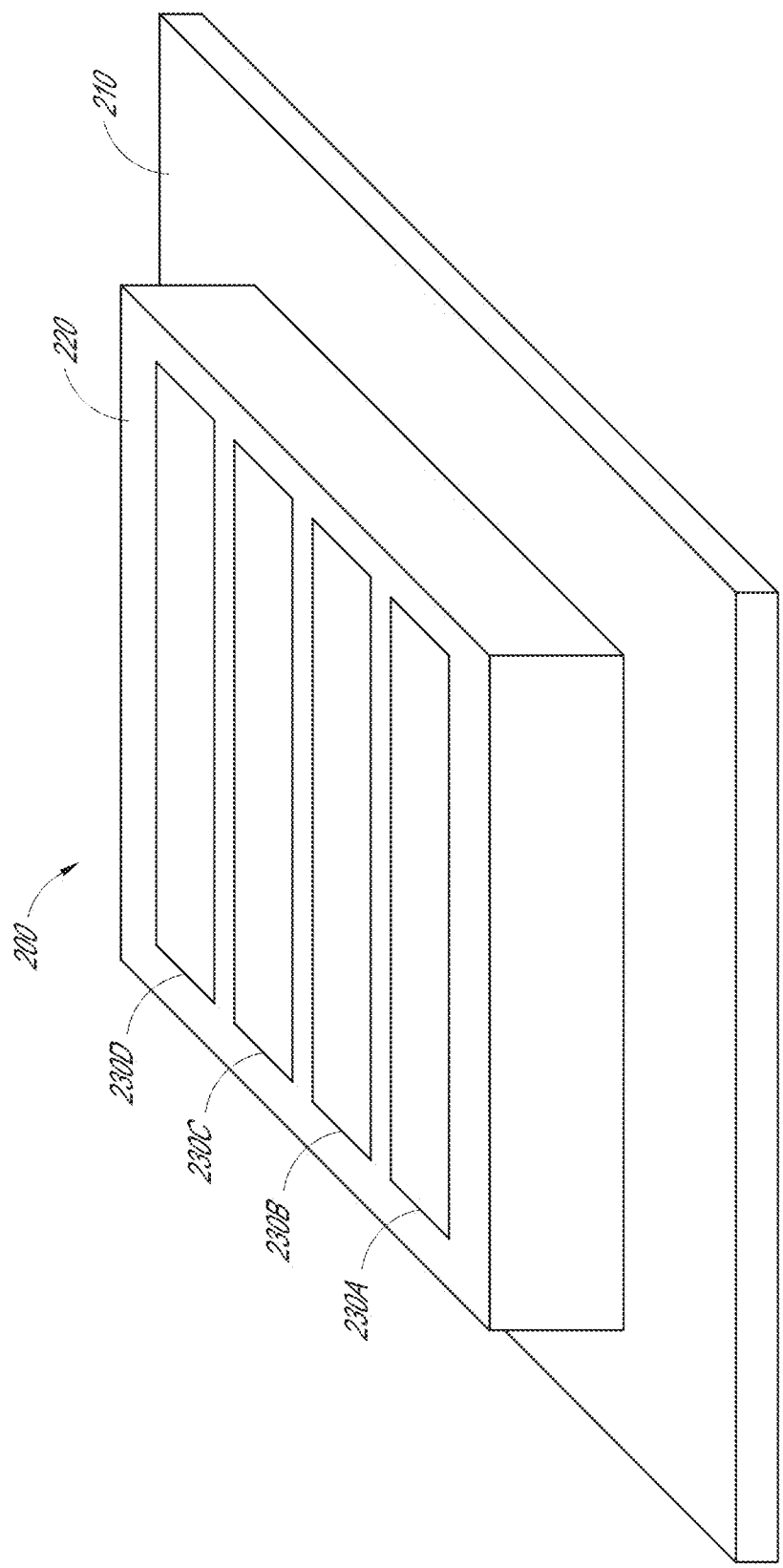
FIG. 20 depicts a perspective view of an imaging gantry in accordance with an illustrative embodiment.

FIG. 20 depicts a perspective view of a two dimensional imaging gantry 200 in accordance with an illustrative embodiment of the present disclosure. The two dimensional imaging gantry can be configured to allow for imaging of multiple animals simultaneously and for simultaneous movement of each of the animals to provide for alternate views. The two dimensional imaging gantry 200 can have a docking interface 210 and a holder 220. The holder 220 can be configured to include a plurality of docking stations 230A, 230B, 230C, and 230D for the receiving animal molds. Each animal mold docking station 230A, 230B, 230C, and 230D can be configured to receive an animal mold, such as animal mold 100, depicted in FIGS. 1-10.

Figure 21:
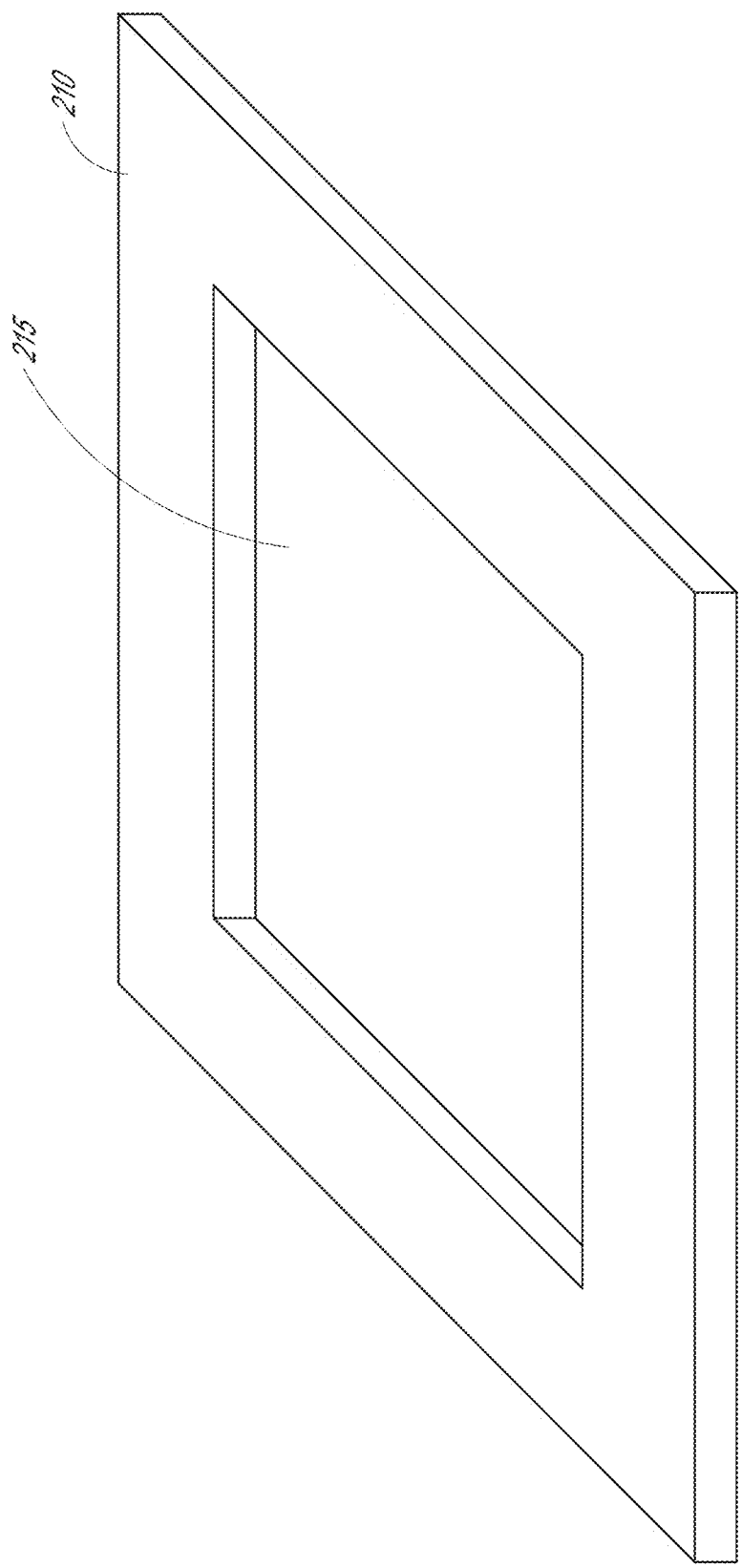
FIG. 21 depicts a perspective view of a docking interface of the imaging gantry in accordance of FIG. 20 with an illustrative embodiment.

FIG. 21 depicts a perspective view of the docking interface 210 of two dimensional imaging gantry 200 in accordance with an illustrative embodiment of the present disclosure. The docking interface 210 includes a recess 215 configured to receive the holder 220. The docking interface 210 can be configured to secure the holder 220 via an interference fit or one or more fasteners. The docking interface 210 can be configured to connect with a system specific interface of an imaging system, for example, by pins, crevices, or any other technique known in the art.

Figure 22:
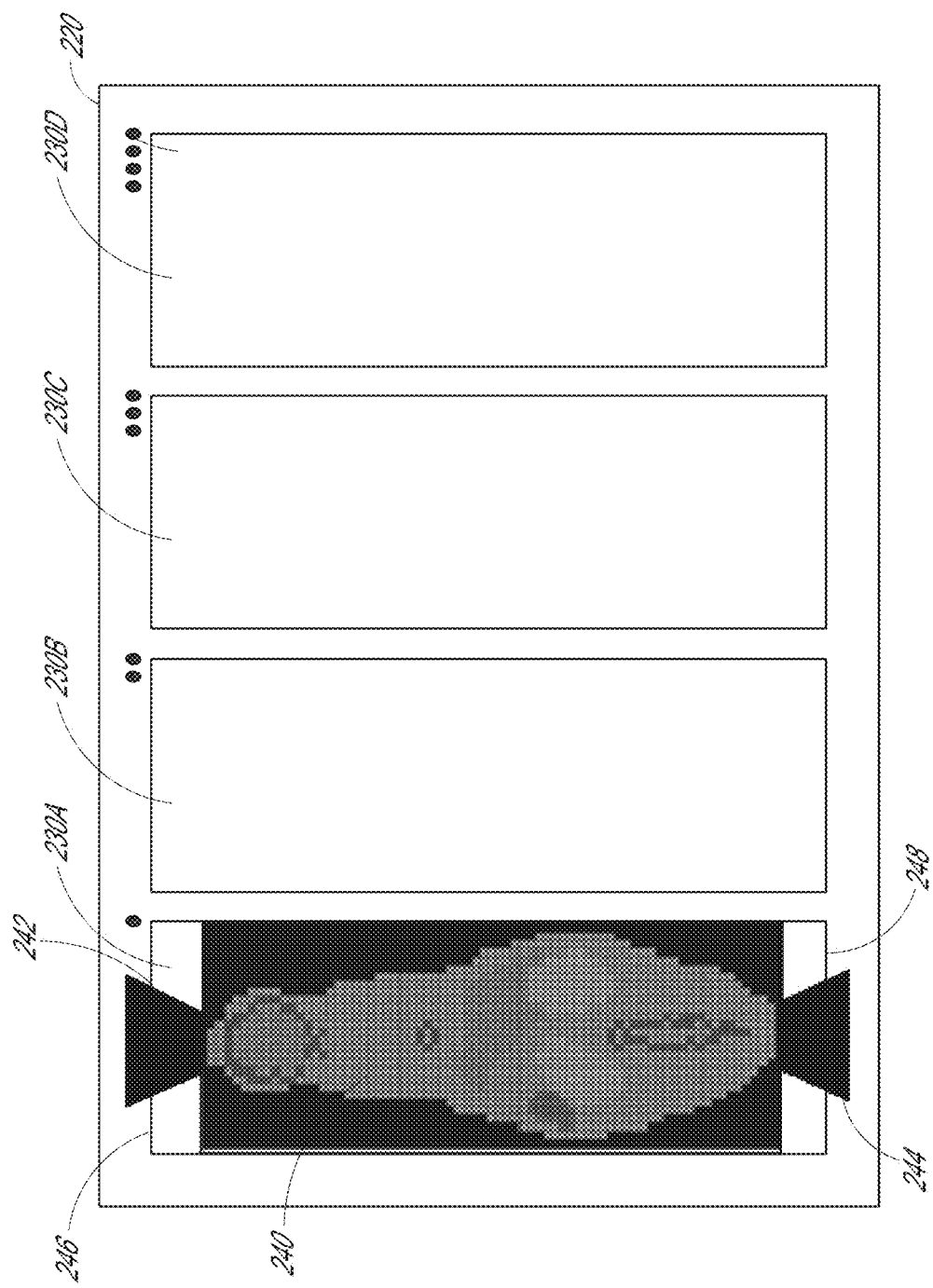
FIG. 22 depicts a top view of a holder of the imaging gantry of FIG. 20 in accordance with an illustrative embodiment of the present disclosure showing several internal components.

FIG. 22 depicts a top view of the holder 220 in accordance with an illustrative embodiment of the present disclosure showing several internal components. FIG. 22 shows an animal mold 240 within chamber 230A of the holder. The animal mold includes a front connection 242 and a rear connection 244 for connecting to an interior front wall 246 and an interior rear wall 248, respectively, of the chamber 230A.

The gantry 200 can be secured to an imaging apparatus, in which the gantry 200 can be rotated by at least 180° in order to image the animals within the holder from at least two different views. The gantry 200 can be connected to a gas anesthesia supply via flexible tubing, which allows movements of the gantry while connected to the gas supply. In some embodiments, the gantry 200 allows for imaging of a dorsal view and a ventral view. In some embodiments, the gantry 200 allows for imaging of opposing lateral views. In some embodiments, the gantry 200 allows for imaging of a cranial view and a caudal view.

Figure 23:
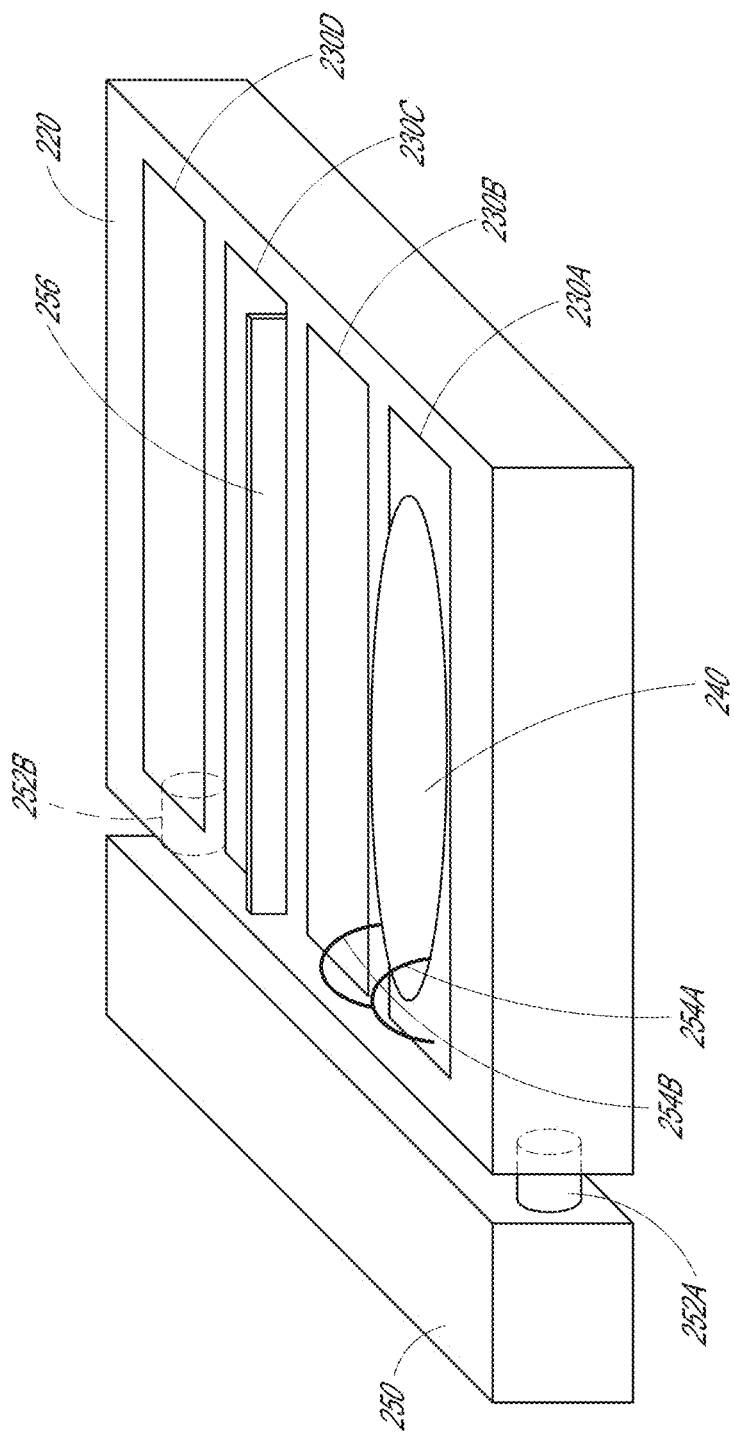
FIG. 23 depicts a perspective view of a holder of the imaging gantry of FIG. 20 connected to a gas supply in accordance with an illustrative embodiment.
Figure 24:
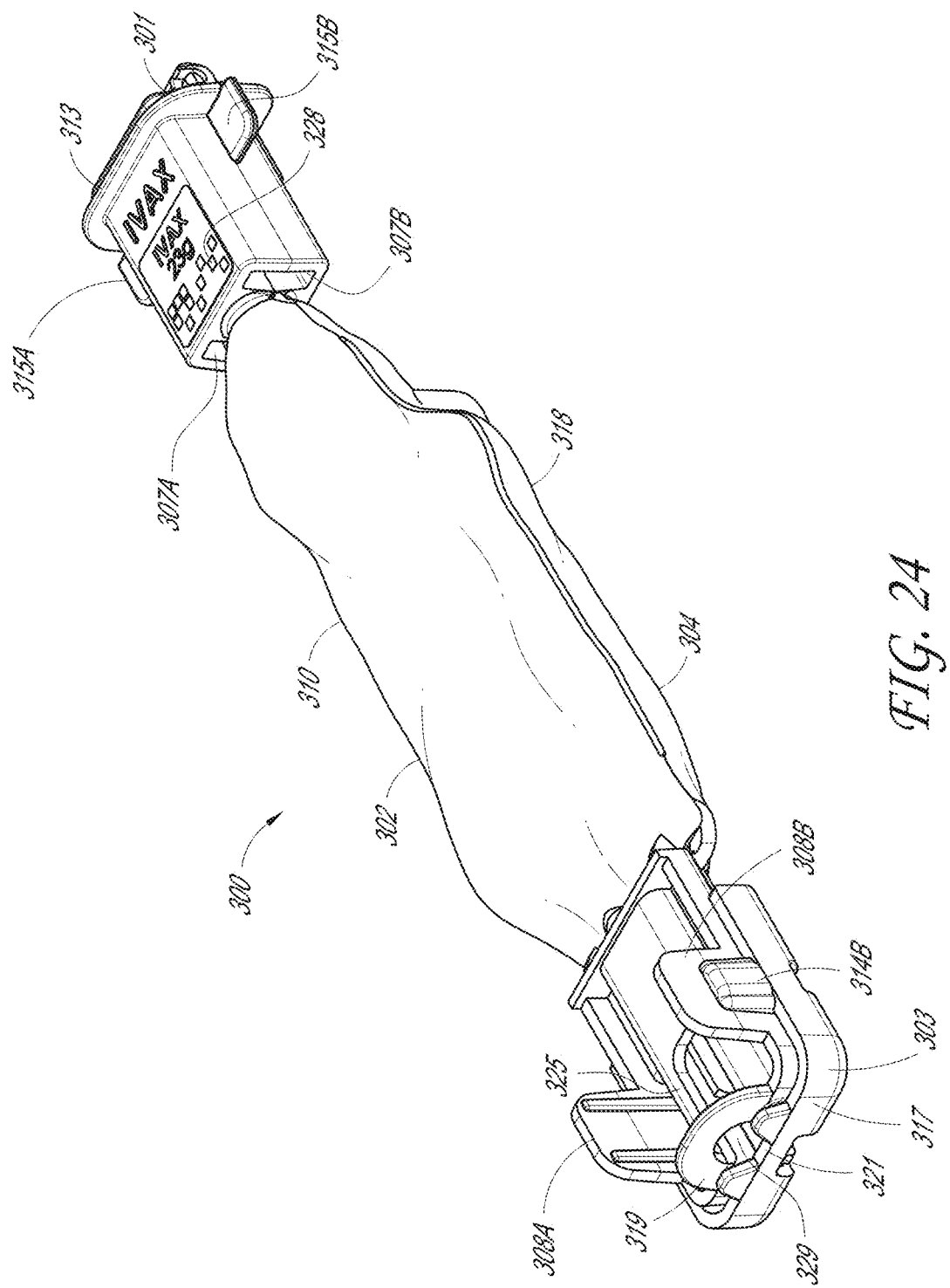
FIG. 24 depicts a perspective view of an animal mold in a closed position in accordance with an illustrative embodiment.
Figure 25:
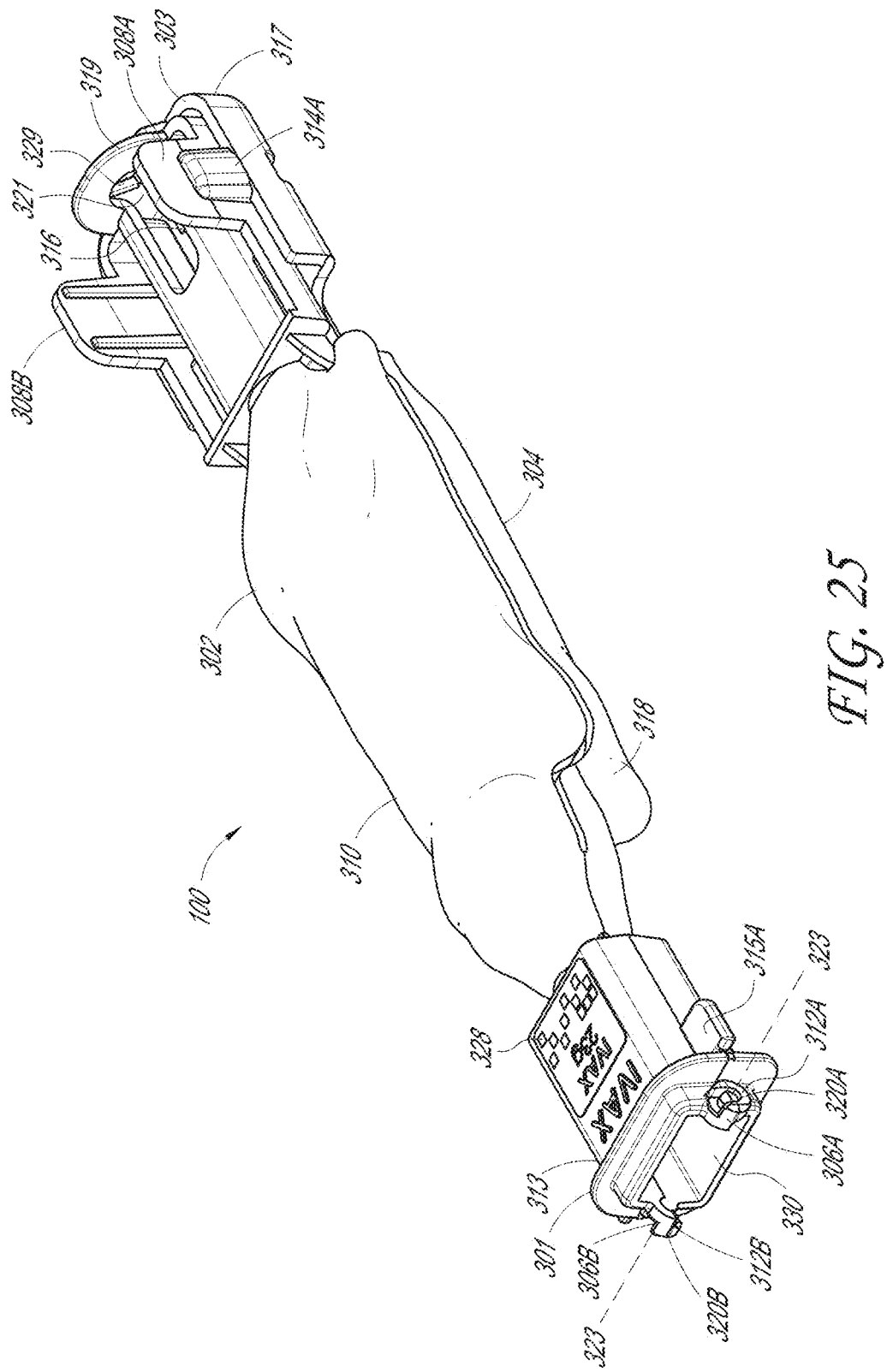
FIG. 25 depicts a perspective view of the animal mold of FIG. 24 in accordance with an illustrative embodiment.
Figure 26:
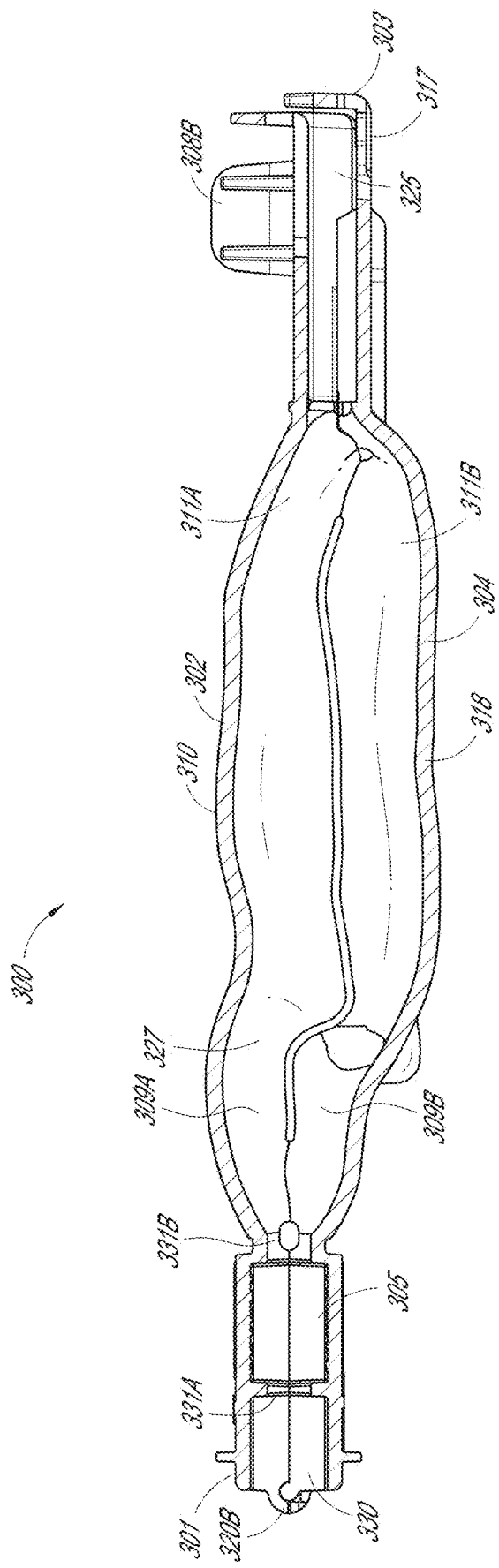
FIG. 26 depicts a cross-sectional view of the animal mold of FIG. 24 in accordance with an illustrative embodiment.
Figure 27:
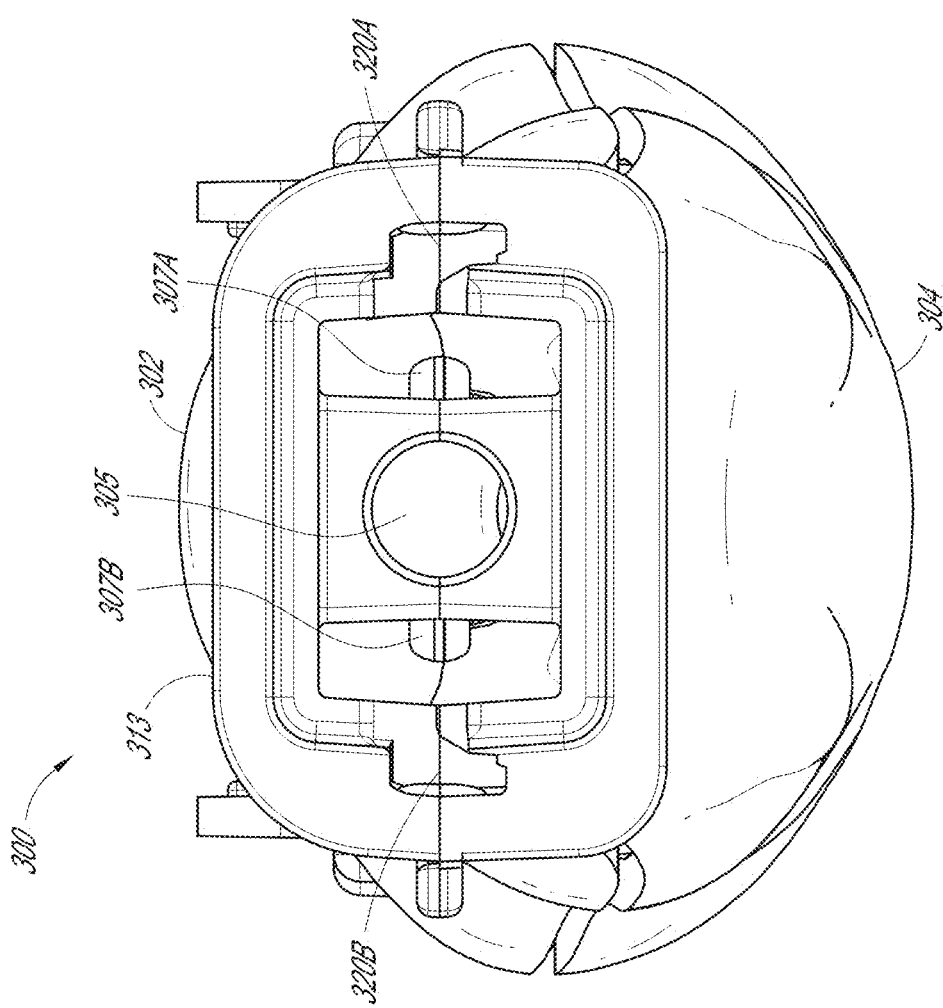
FIG. 27 depicts a front view of the animal mold of FIG. 24 in accordance with an illustrative embodiment.
Figure 28:
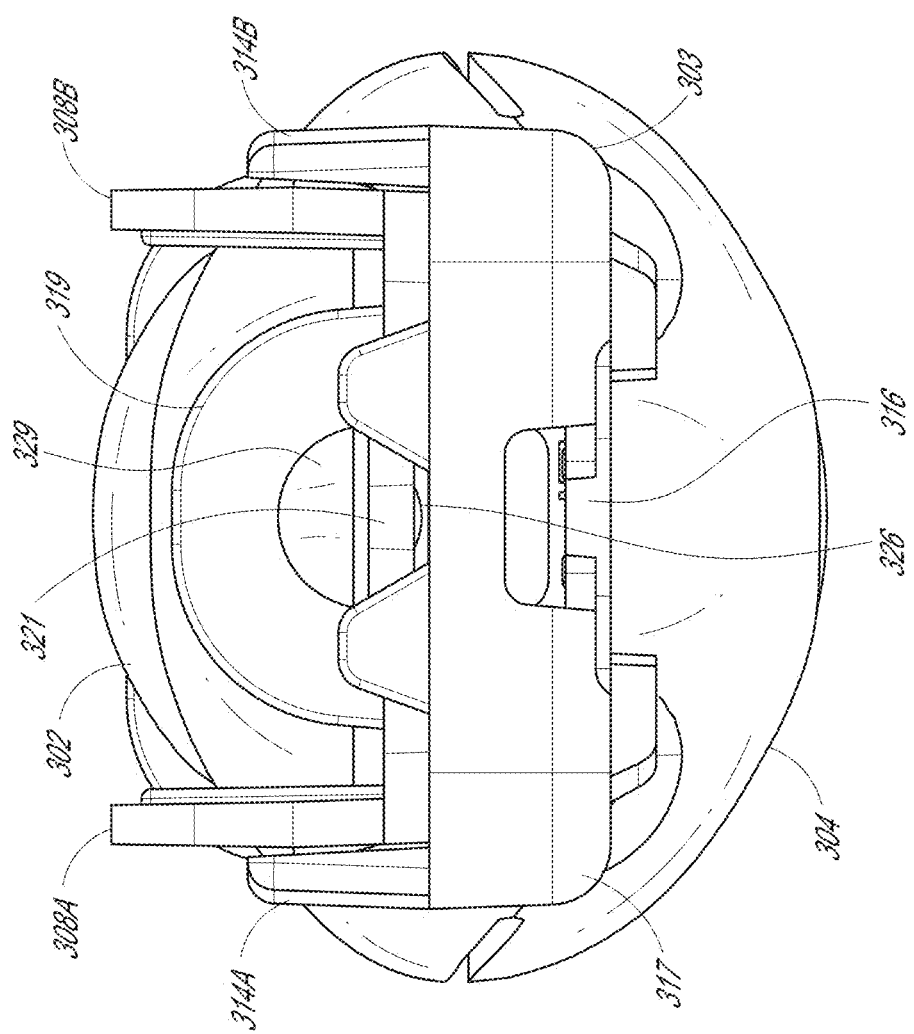
FIG. 28 depicts a rear view of the animal mold of FIG. 24 in accordance with an illustrative embodiment.
Figure 29:
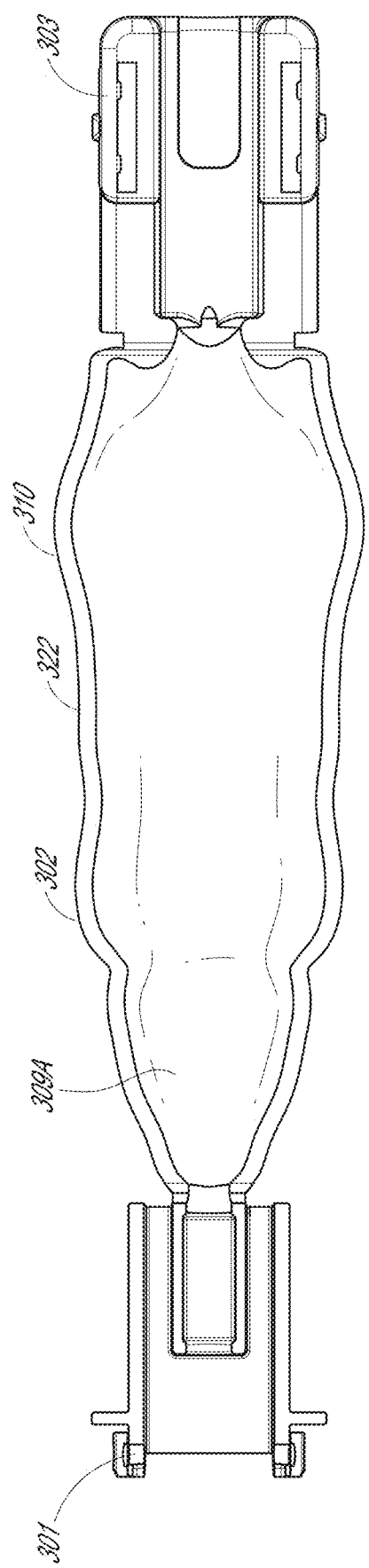
FIG. 29 depicts a bottom view of a top section of the animal mold of FIG. 24 in accordance with an illustrative embodiment.
Figure 30:
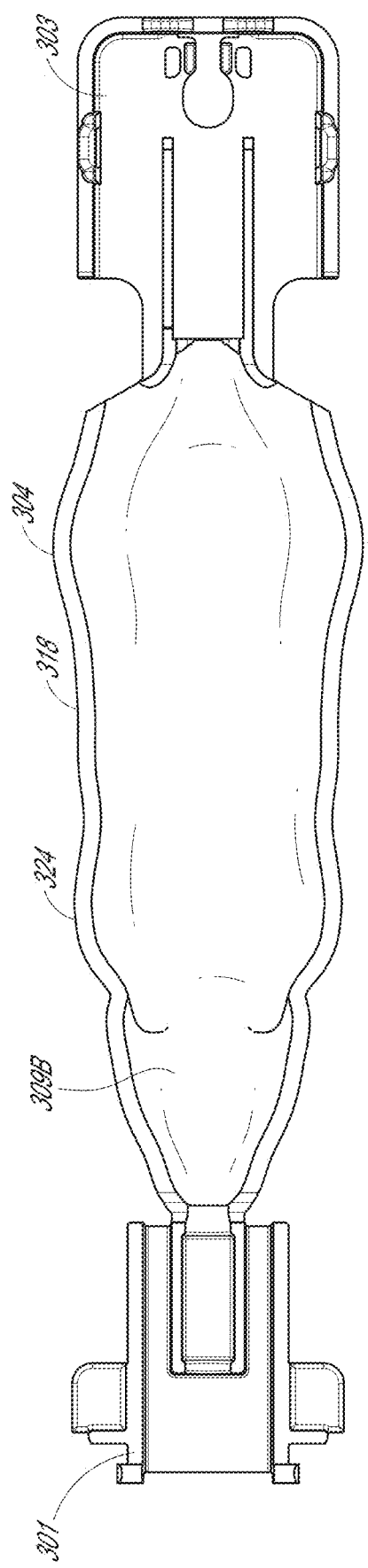
FIG. 30 depicts a top view of a bottom section of the animal mold of FIG. 24 in accordance with an illustrative embodiment.

FIG. 23 depicts a perspective view of the holder 220 connected to a gas supply bar 250 in accordance with an illustrative embodiment of the present disclosure. The gas supply bar can be configured to engage with the docking interface 210 Extending from the gas supply bar 250 are gas supply pipes 252A and 252B, which extend to an inner cavity of the holder 220. Tubes 254A and 254B extend from the inner cavity of the holder 220 to openings within the animal mold 240, which can be similar to openings 107A and 107B of animal mold 100, as discussed above with respect to FIGS. 1-10. Gas, such as anesthesia can flow from the gas supply bar 250 through the pipes 252A and 252B into the inner cavity of the holder 220. From the inner cavity of the holder 220, the gas can flow through the tubes 254A and 254B to the animal mold 240. Optical blinds (screens) may further be positioned between chambers 230A-D in order to prevent light leakage from adjacent animal molds, which are an ambient light source. An optical blind 256 is shown positioned between chambers 230B and 230C.

FIGS. 24-30 depict an embodiment of an animal mold 300 in accordance with an illustrative embodiment. FIGS. 24, 25, 26, 27, 28, 29, and 30 depict a first perspective view, a second perspective view, a cross-sectional view, a front view, a rear view, a bottom view of a top section, and a top view of a bottom section, respectively, of the animal mold 300 in a closed position in accordance with an illustrative embodiment. In this embodiment, the animal mold 300 can be generally shaped to conform to the body of a rodent, such as a mouse, such that the animal mold 300 is generally body conforming to the animal. The animal mold 300 can include a proximal end 301 and a distal end 303. The animal mold 300 can further include a top section 302 and a bottom section 304. The top section 302 can include a body conforming section 310 and the bottom section 304 can include a body conforming section 318. The proximal end 301 of the animal mold 300 can include hinge connections 306A, 306B, 312A and 312B, a proximal passage 330, a gas delivery passage 305, a pair of scavenging passages 307A and 307B, a peripheral edge 313, a computer readable label 328, and a pair of wings 315A and 315B.

The hinge connections 306A and 306B, positioned on the top section 302 can be engaged to the hinge connections 312A and 312B, respectively, positioned on the bottom section 304 so as to form hinges 320A and 320B having a pivot axis along line 323-323. The top section 302 can be rotated with respect to the bottom section 304 along the pivot axis between the closed position shown in FIG. 24 and an open position. The top section 302 can be configured to rotate away from the bottom section 304 so as to provide sufficient space to place an animal within the body conforming section 318 when in the open position.

The passages 330, 305, 307A, and 307B can be formed from sections of the upper portion 302 and lower portion 304 of the animal mold 300 engaging one another when the animal mold 300 is in the closed position. Passages 305, 307A, and 307B can be positioned within the passage 330 distally from a proximal end of the passage 330. Passage 330 can be configured to receive one or more gas supply components. Passage 305 can be configured to receive gas from a gas supply component at its proximal end 331A and to deliver gas to the body conforming sections 310 and 318 at its distal end 331B. The distal end 331B of the passage 305 can open to the proximal end of the body conforming sections 310 and 318. Gas can flow through the body conforming sections 310 and 318 and out of an opening 326 positioned at the distal end of the body conforming sections 310 and 318. Passages 307A and 307B can be configured for scavenging gas flowing out of the animal mold 300. Scavenging may be active, using a suction mechanism, or passive, allowing for the flow of gas without the applying suction.

The peripheral edge 313 and wings 315A and 315B of the animal mold 300 can be configured to engage a support structure of an imaging apparatus, such as a gantry, in order to maintain the animal mold 300 in a consistent position for optical imaging.

The computer readable label 328 can be a barcode, a QR code, or any other computer readable label known in the art. The computer readable label 328 can be configured such that the computer readable label is detectable in a photographic image captured by an optical imaging system, such as, for example, imaging gantry 150, imaging gantry 200, imaging gantry 350, and imaging gantry 400 as described herein. The computer readable label 328 can be configured to be processed by an imaging recognition software following capture of an image by the optical imaging system, for example, to extract data from the computer readable label 328. In some embodiments, the computer readable label 328 can include fields of black and white areas, such as quadrants or bars. Fields of black and white bars may be preferable for creating image contrast for detection by the imaging recognition software. In some embodiments, the computer readable label 328 can encode at least 64 bit information.

The computer readable label 328 can store or be associated with animal mold data, imaging data, customer data, animal specimen data, or any other data relevant to imaging an anatomical structure. For example, a computer readable label 328 can store or be associated with data related to the size of the animal mold 300 and the shape of the animal mold 300. As described herein, animal molds may be produced at various sizes and shapes to accommodate different strains and sizes of animal specimens. Specimen data can include a size, sex, and/or species information for an animal specimen. A computer readable label 328 can also store or be associated with customer/client identification data. This data can facilitate tracking of personalized settings and use in an imaging system. In some embodiments, multiple computer readable labels can be attached to or formed in the animal mold 300 in multiple positions. For example, a first computer readable label can be positioned on the top section 302 and a second computer readable label can be placed on the bottom section 304 to allow for identification of the different components of the animal mold 300 and/or to allow for the identification of images captured by an imaging device as dorsal or ventral views. In some embodiments, the computer readable label 328 can be attached to or formed in the animal mold 300 at a position in close proximity to the body conforming sections 310 and 318. Placement of the computer readable label 328 close to the body conforming sections 310 and 318 can allow for a smaller camera field-of-view ("FOV") for capturing the computer readable label 328 and the animal specimen within the animal mold 300. For example, the computer readable label 328 may be positioned close to a cranial section of the body conforming sections 310 and 318. In some embodiments, the computer readable label 328 can be positioned close in proximity to a section of the animal mold 300 intended to receive a nose or snout of an animal specimen placed therein.

At the distal end 303 of the animal mold 300, the bottom section 304 can include a plate 317. The plate 317 can include a pair of locking members 314A and 314B extending vertically, a recess 316, and a crossbar 321. At the distal end 303 of the animal mold 300, the top section 302 can include a plate 325 having tabs 308A and 308B and a curved crossbar 319.

The plate 317 can be configured to engage a support structure of an imaging apparatus, such as a gantry, in order to maintain the animal mold 300 in a consistent position for optical imaging. The recess 316 can be configured to receive a fastener in order to further secure the animal mold 300 to an imaging apparatus. A bottom surface of the plate 325 can be shaped to detachably engage a top surface of the plate 317 when the animal mold 300 is in the closed position. Locking member 314A and tab 308A can comprise complementary connection components for detachably securing to one another. Likewise, locking member 314B and tab 308B can comprise complementary connection components for detachably securing to one another. In some embodiments, each locking member 314A and 314B can include a recess on an interior surface of the locking member configured to receive a protrusion on the exterior surface of the tabs 308A and 308B, respectively. In some embodiments, a force can be applied to each tab 308A and 308B in a direction away from the corresponding locking members 314A and 314B to disengage the tabs 308A and 308B from the locking members 314A and 314B.

An upper surface of the crossbar 321 and lower surface of the crossbar 319 can define an opening 329 when the animal mold 300 is in the closed position. The opening 329 can be configured to secure the tail of an animal, such as a rodent. Securing the tail of an animal can facilitate tail vein catheterization, which may provide an additional mechanism for applying anesthesia to the animal.

As noted above, the animal mold 300 can be made of a solid material that is optically transparent or at least partially transparent to facilitate optical imaging of an animal within the interior of the animal mold 100. In non-optical imaging embodiments, the animal mold 300 can be mode of a material that is transparent to the imaging modality. The animal mold 300 can be configured so that the animal mold 300 slightly compresses an animal in the interior of the animal mold 300 so that the animal is at least partially restrained and so that the outer surface of the animal body can contact the interior surface of the animal mold 300. In some arrangements, the animal mold 300 can provide a constant spatial frame of reference across different animals, and can also provide a consistent surface for camera detection points. The top and bottom sections 302 and 304 of the animal mold 300 define a pre-defined interior surface 327, which can be correlated to a given animal (for example mouse) age, strain, gender and/or weight. As shown in FIGS. 24-28, a set of molds can be provided that can correspond to different animal (for example mouse) age, strain, gender and/or weight categories. In this manner, the mold 300 can hold the animals in a fixed posture and provide a constant spatial frame of reference across different animals within a category, and can also provide a consistent surface for camera detection point.

A cranial portion 309A of the body conforming section 310 can be positioned distally from the distal end 331B of the passage 305 and at the proximal end of the body conforming section 310 and can be configured to receive a cranial segment of the animal. A cranial portion 309B can be positioned at the proximal end of the body conforming section 318 and can be configured to receive a cranial segment of the animal. The distal end 331B of the passage 305 can be configured to allow gas to flow to the cranial portions 309A and 309B when the animal mold 300 is in a closed position. A caudal section 311A can be positioned at the distal end of the body conforming section 310 can be configured to receive a caudal segment of the animal. The body conforming section 310 can be shaped and sized so as to generally conform to a dorsal segment of the animal. A caudal portion 311B of the body conforming section 318 can be positioned at the distal end of the body conforming section 318 and can be configured to receive a caudal segment of the animal. The body conforming section 318 can be shaped and sized so as to generally conform to a ventral segment of an animal. The body conforming section 310 can further include a bottom edge 322 configured to engage a top edge 324 of the body conforming section 318.

FIGS. 31-38 depict an embodiment of a gantry 350 in accordance with an illustrative embodiment of the present disclosure. The gantry 350 can include many components that are the same as or similar to components of the gantry 150 depicted in FIGS. 11A-19. FIG. 131 depicts a perspective view of the gantry 350 in accordance with an illustrative embodiment of the present disclosure. As will be explained below, in the illustrative embodiment, the gantry 350 can include one or more mirrors that can aid in imaging an animal positioned within an animal mold that is supported by the gantry. The gantry 350 can be configured to receive an animal mold, such as the animal mold 300 according to one of the embodiments described herein. The gantry 350 can further be configured to receive a gas from a gas supply.

The gantry 350 can include a lid 351 having a window 352, a front plate 354A, a back plate 354B, side walls 356A and 356B, and a sliding handle 358. In some embodiments, the sliding handle 358 can be configured to move proximally towards or distally from the front plate 354A in response to the application of manual force. The handle 358 may be operated in a similar manner to the handle 158 described above with respect to FIGS. 11A-19.

FIG. 32 depicts a top sectional view of the gantry 350 in accordance with an illustrative embodiment of the present disclosure showing the animal mold 300 secured to the gantry 350. The sliding handle 358 can be engaged to a rod 360. Rod 360 can be engaged to a mold support 364, which can be configured to support the proximal end 301 of the animal mold 300. The distal end 303 of the animal mold 300 can be further secured to an interior surface of the handle 358 through a mold support 382. The distal end 303 can be received by a recess 383 of the mold support 382. Engagement of the animal mold 300 to the mold support 364 and mold support 382 can fix the animal mold 300 in place within the gantry 350 when the gantry 350 is in the closed position to allow for optical imaging of an animal within the animal mold 300. The mold support 364 can be further configured to engage a sliding member 366 that can be slidably mounted to a track 368 such that the handle 358 can translate from an open position to a closed position.

FIG. 32 further shows a gas output nozzle 379 configured to receive gas from the scavenging passages 307A and 307B. The gas output nozzle 379 can be engaged to the back plate 354B and can extend into an opening in the back plate 354B to receive gas from the scavenging passages 307A and 307B. The gantry 350 can further include a gas block 384. The gas block 384 can include a mount 385 and a mold receiving channel 387 configured to engage the proximal end 301 of the animal mold 300. The mount 385 can be secured to the interior wall of the front plate 354A by one or more fasteners, or can be integrally formed with the front plate 354A. The channel 387 can be shaped and sized to receive the hinges 320A and 320B and a proximal end of the passage 330. The channel 387 can be configured such that when the proximal end 301 of the animal mold 300 is received in the channel 387, the peripheral edge 313 fits within channel 387 to seal or substantially seal the channel 387. Engagement of the peripheral edge 313 within the channel 387 can allow gas to flow between the block 384 and the animal mold 300 while preventing gas from leaking out of the channel 387 and into the gantry 350. The channel 387 can further include a pair of slots 373A and 373B (not shown in FIG. 32) configured to receive wings 315A and 315B, respectively, of the animal mold 300. The slots 373A and 373B can provide an indexing feature to assure alignment of the animal mold 300 with the gas block 384.

FIG. 32 further depicts mirrors 380A and 380B. The mirrors 380A and 380B can provide for simultaneous imaging of two different views of an animal within the animal mold 300.

Figure 33A:
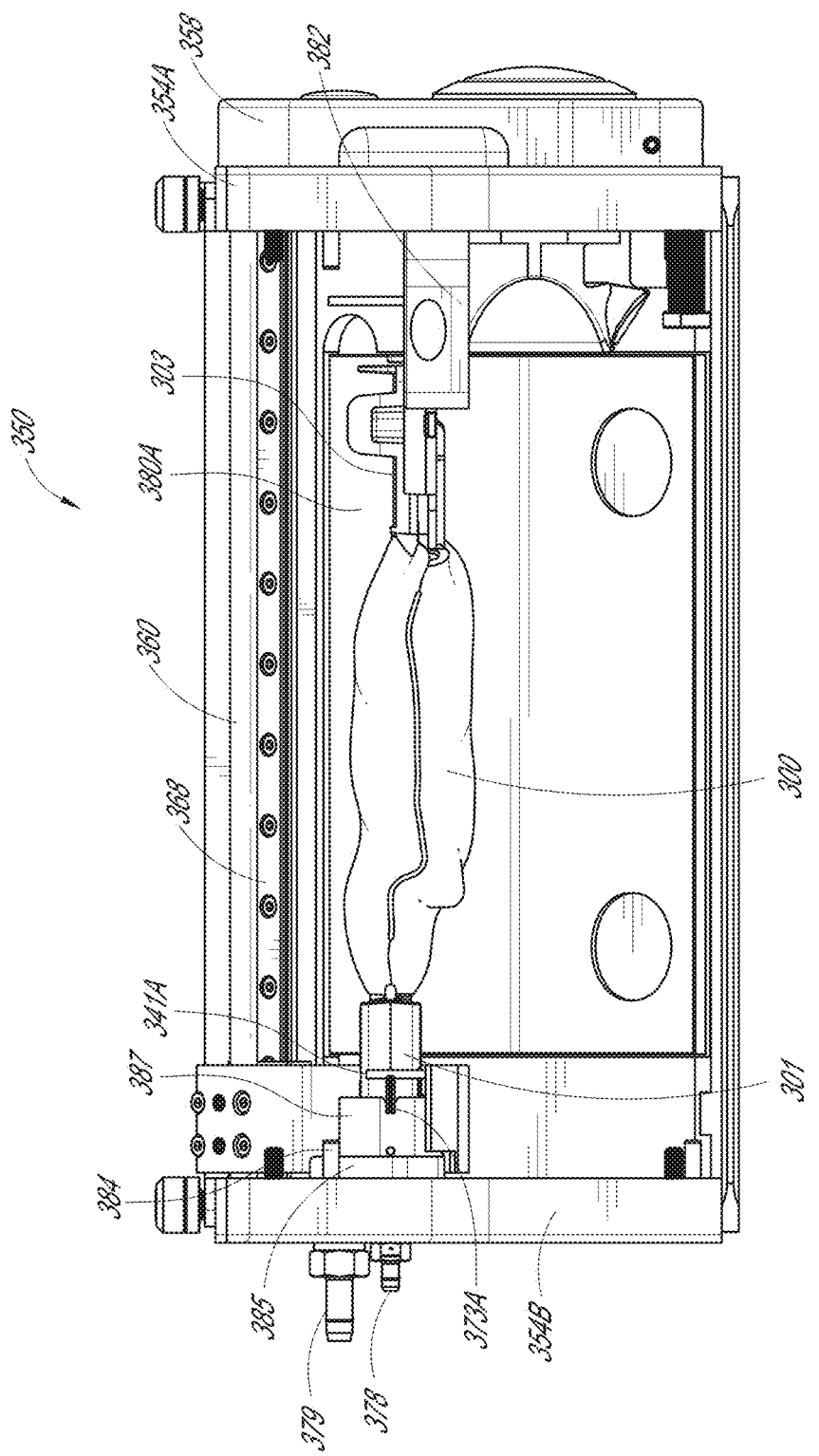
FIG. 33A depicts a side view of the gantry of FIG. 31 having several components removed in accordance with an illustrative embodiment.

FIG. 33A shows a side view of the gantry 350 having the side wall 356A, the mirror 380B, lid 351 and window 352 removed in accordance with an illustrative embodiment of the present disclosure. FIG. 33 further shows the wing 315A of the animal mold 300 engaged with the slot 373A and a fastener 341A. The fastener 341A can be positioned distally from the wing 315A when the wing 315A is engaged with the slot 373A and can secure the animal mold 300 in position with the gas block 384. The fastener 341 can prevent distal movement of the wing 315A in order to prevent distal movement of the animal mold 300. A fastener 341B (not shown in FIG. 33A) can be positioned behind the wing 315B when the wing 315B is positioned within the slot 373B and can function to prevent distal movement of the wing 315B in order to prevent distal movement of the animal mold 300. The gantry 350 further includes a gas supply nozzle 378 engaged to the back plate 354B. The gas supply nozzle 378 can be configured to provide gas into an opening in the back plate 354B in order to direct the gas to the passage 305.

Figure 33B:
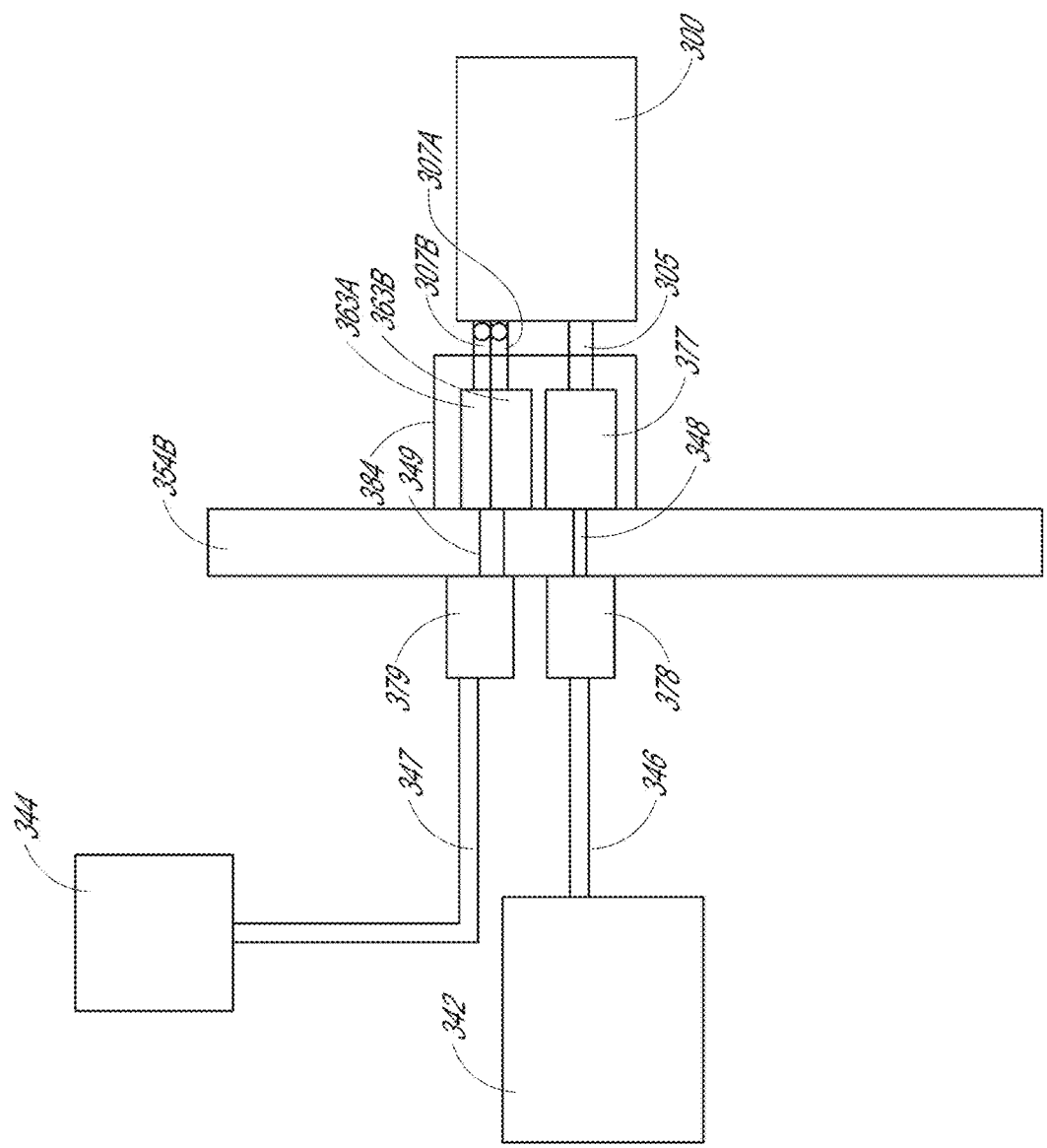
FIG. 33B depicts a schematic side view of the gantry of FIG. 31 having several components removed in accordance with an illustrative embodiment.

FIG. 33B shows a schematic side view of the gantry 350 having several components removed. A gas supply source 342 can be connected to the gas supply nozzle 378 by a pipe 346. Gas can flow from the gas supply source 342 to the gas supply nozzle 378. The gas can then flow into the nozzle 378 and through a conduit 348 in the back plate 354B. The gas can flow through the back plate 354B into a nozzle 377 extending from the interior wall of the back plate 354B and through the gas block 384. The nozzle 377 can direct gas to the gas delivery passage 305 of the animal mold 300. A vacuum source 344 can be connected to the gas output nozzle 379 by a pipe 347. The gas output nozzle 379 is connected to a conduit 349 within the back plate 354B. The conduit 349 is connected to scavenging channels 363A and 363B positioned within the gas block 384. Scavenging channels 363A and 363B are connected to scavenging passages 307A and 307B, respectively, of the animal mold 300. A vacuum force can be applied by the vacuum source 344 to draw excess gas into the passages 307A and 307B from the gantry 350, including excess gas escaping the animal mold 300.

Figure 34:
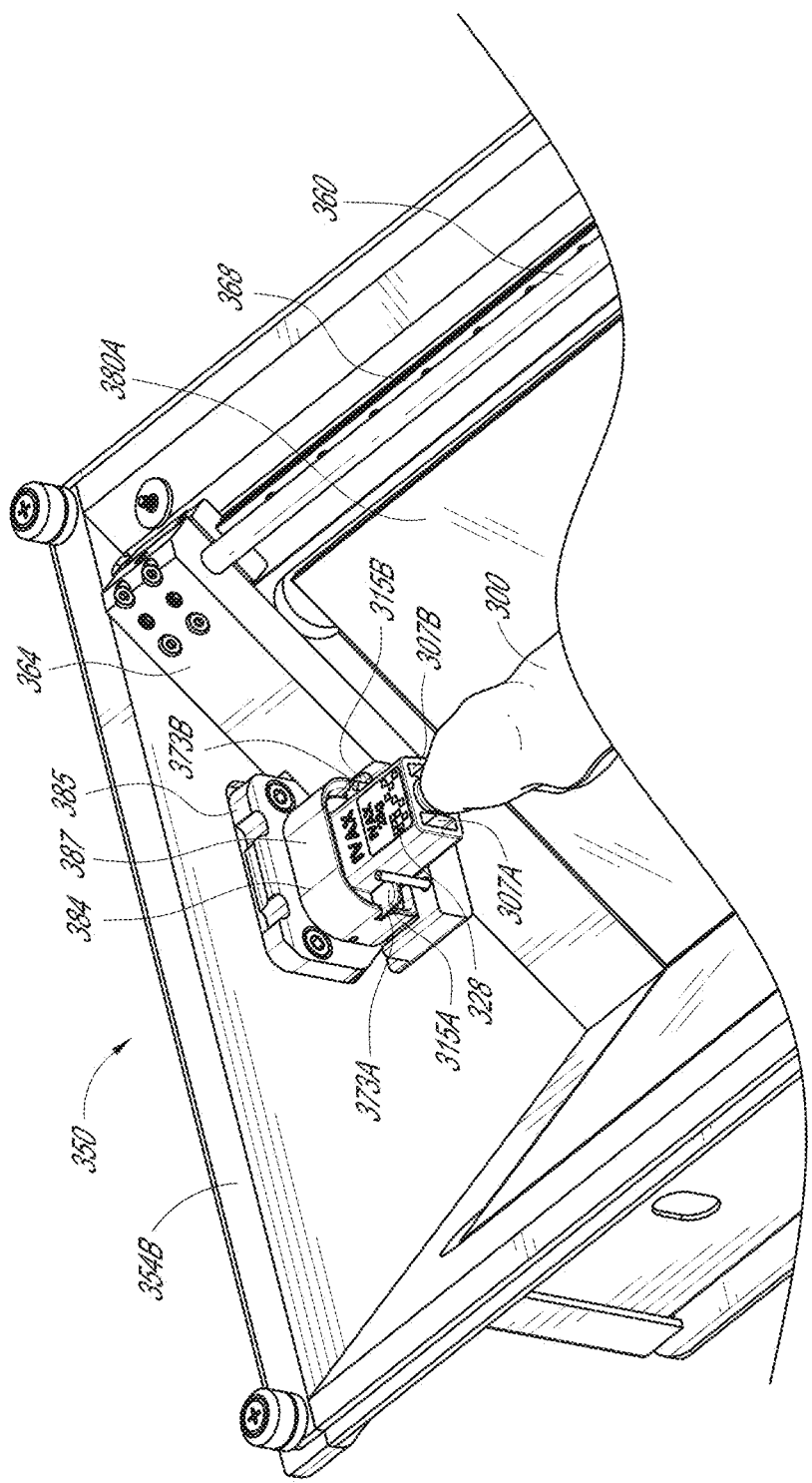
FIG. 34 depicts a perspective view of the gantry of FIG. 31 having several components removed in accordance with an illustrative embodiment.

FIG. 34 shows a perspective view of a section of the gantry 350 having the lid 351 and window 352 removed. FIG. 34 shows the wing 315B engaged with the slot 373B. FIG. 34 further shows the fastener 373B positioned behind the wing 315B.

Figure 35:
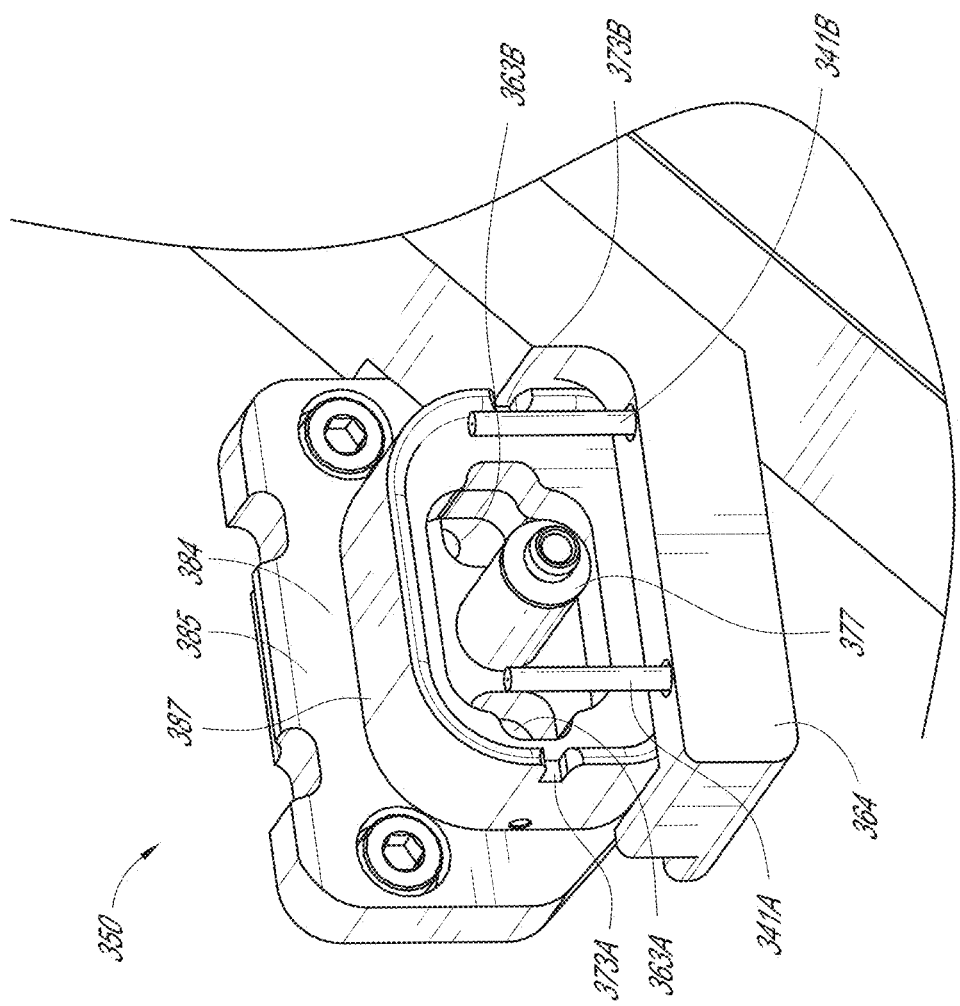
FIG. 35 depicts a perspective view of the gantry of FIG. 31 having several components removed in accordance with an illustrative embodiment.

FIG. 35 shows a perspective view of a section of the gantry 350 having the lid 351, window 352, and animal mold 300 removed. FIG. 35 shows the nozzle 377 extending from the interior wall of the back plate 354B and through the gas block 384. The nozzle 377 can be configured to receive gas from the gas supply nozzle 378 and to direct gas to the gas delivery passage 305. The gas block 384 can also include scavenging channels 363A and 363B configured to receive gas from the scavenging passages 307A and 307B. As described above, gas can flow from the scavenging passages 307A and 307B through the scavenging channels 363A and 363B and to the gas output nozzle 379.

Figure 36:
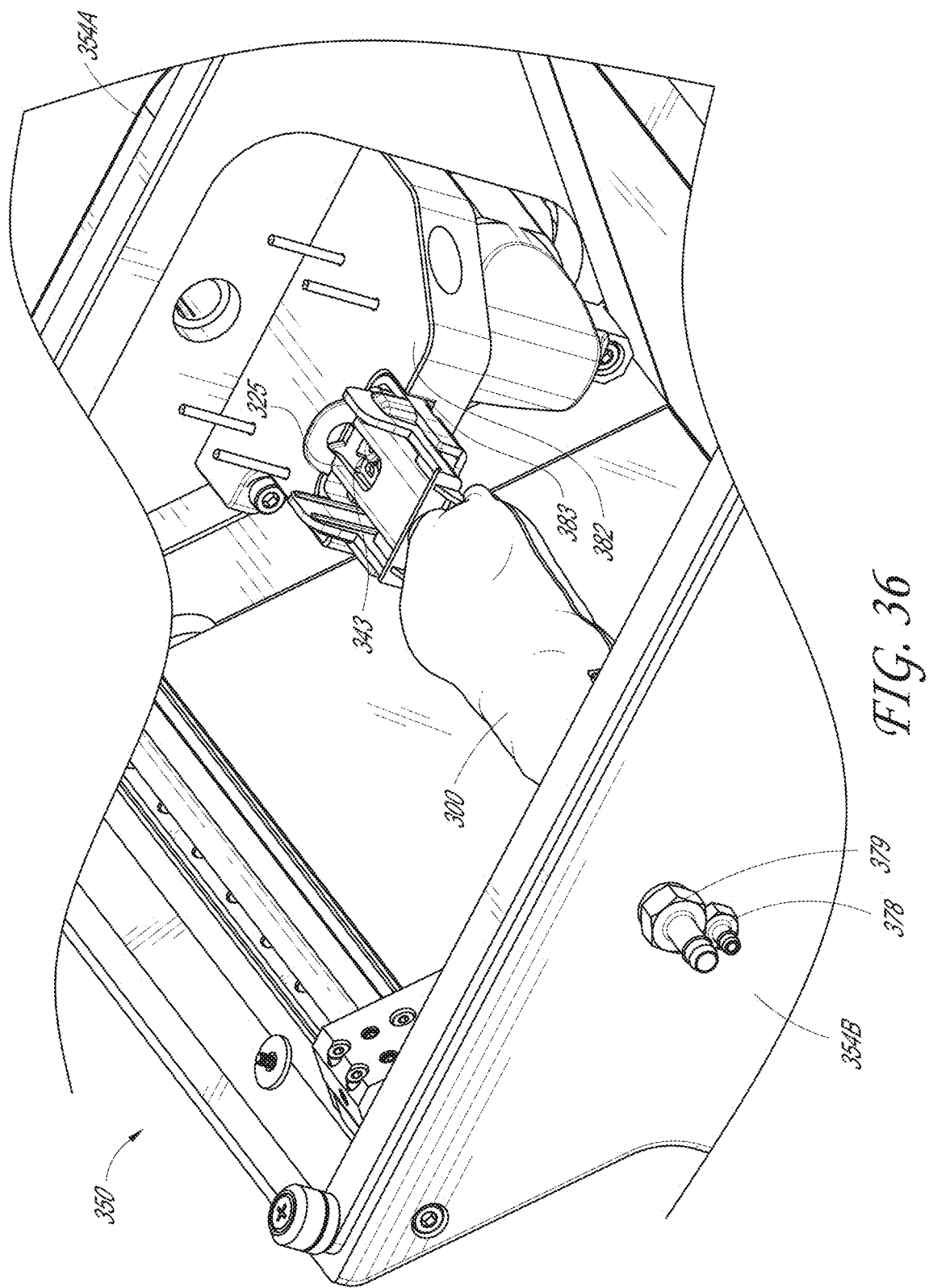
FIG. 36 depicts a perspective view of the gantry of FIG. 31 having several components removed in accordance with an illustrative embodiment.
Figure 37:
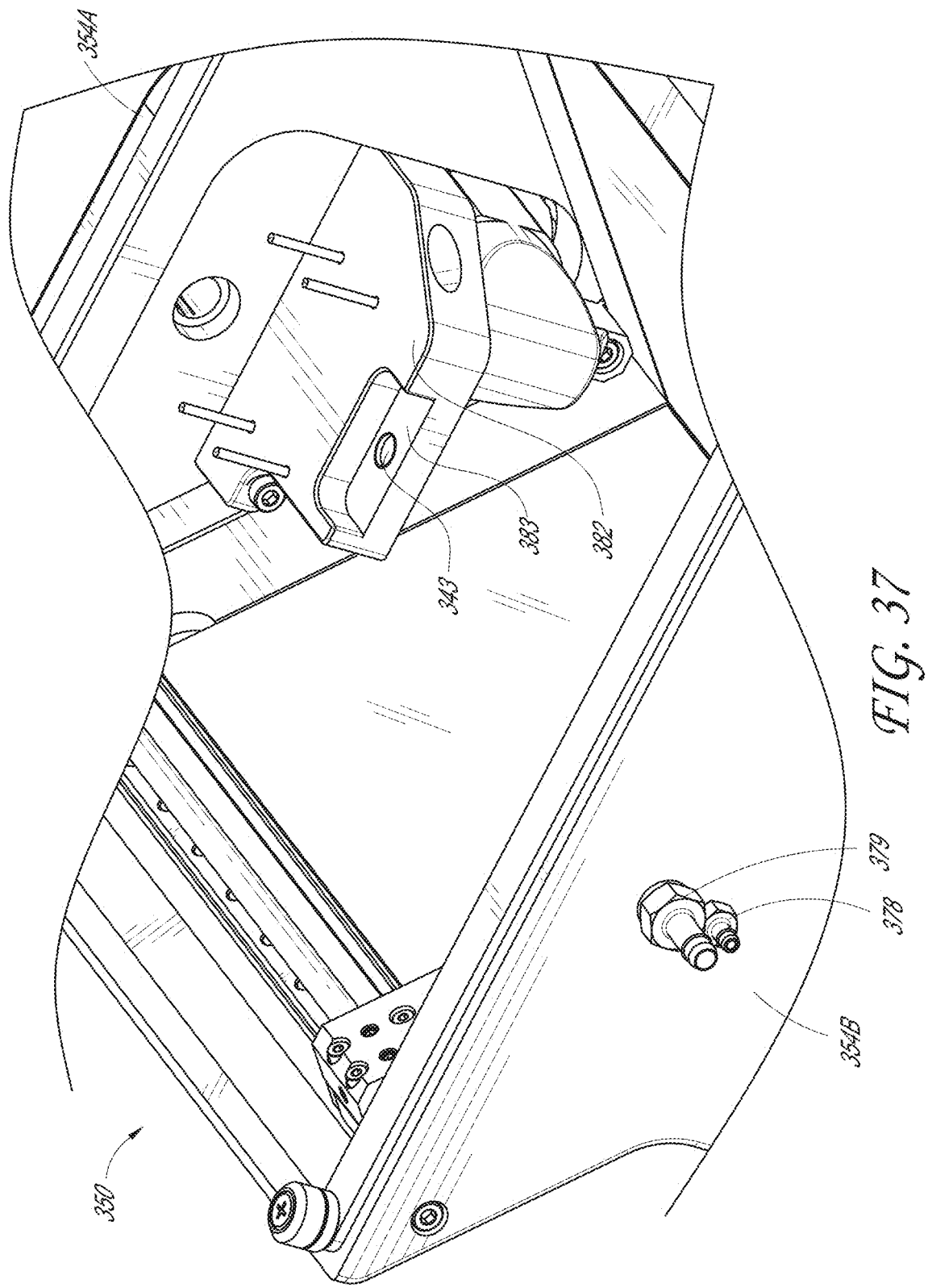
FIG. 37 depicts a perspective view of the gantry of FIG. 31 having several components removed in accordance with an illustrative embodiment.

FIG. 36 shows a perspective view of a section of the gantry 350 having the lid 351 and window 352 removed. FIG. 36 shows the distal end 303 of the animal mold 300 positioned in the recess 383 of the mold support 382. The distal end 303 of the animal mold 300 can be secured to the mold support 382 by a fastener 345 extending through the recess 316 of the animal mold 300. FIG. 37 shows a perspective view of a section of the gantry 350 having the lid 351, window 352, and animal mold 300 removed. The recess 383 of the mold support 382 includes an aperture 343 for receiving the fastener 345.

Figure 38:
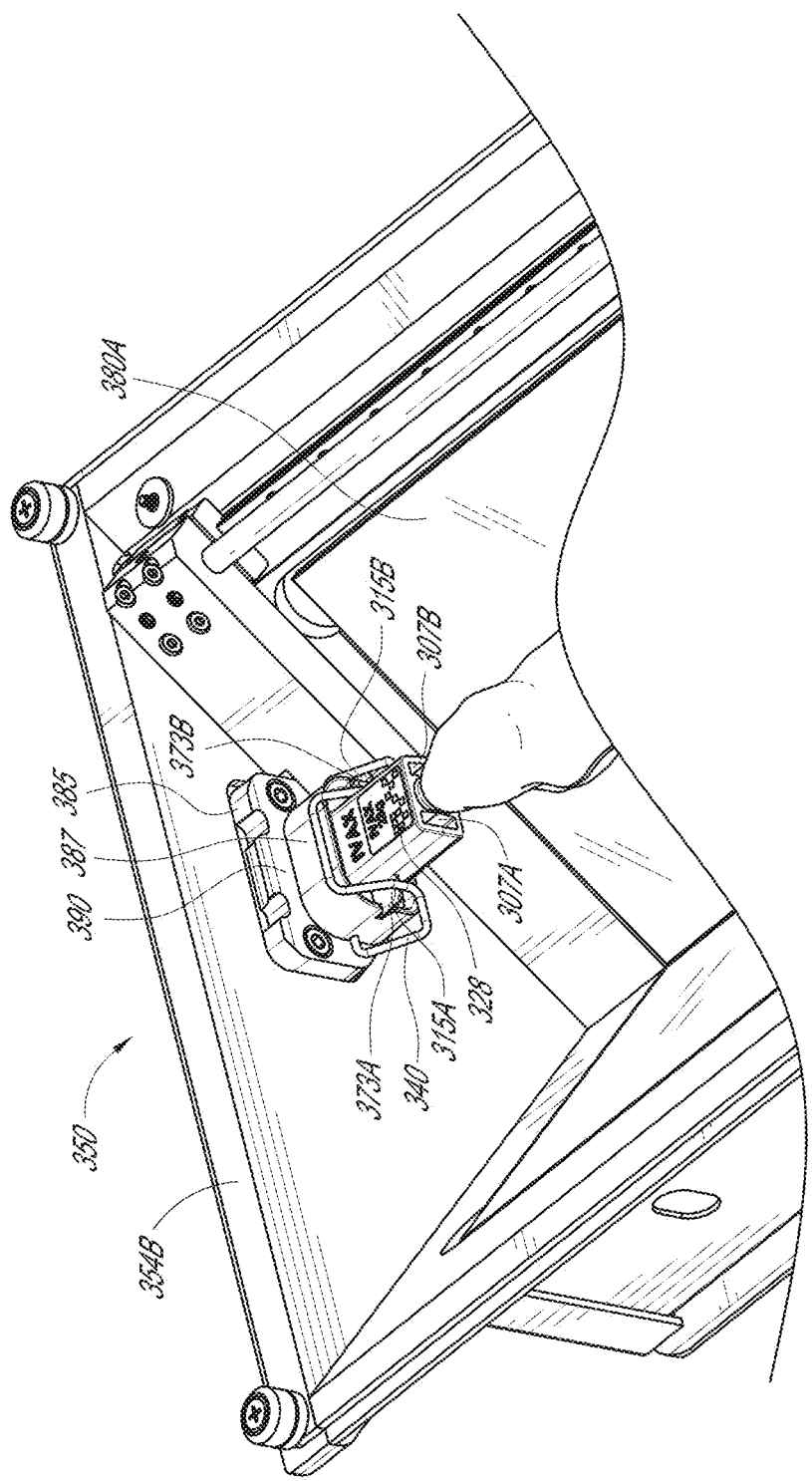
FIG. 38 depicts a perspective view of an alternative embodiment of the gantry of FIG. 31 having several components removed in accordance with an illustrative embodiment.

FIG. 38 shows a perspective view of a section of the gantry 350 having the lid 351 and window 352 removed and showing an alternative embodiment of a gas block 390. The gas block 390 can include many of the same or similar components to the gas block 384. The gas block 390 further includes a wire latch 340 extends from the channel 387. The wire latch 340 can extend around a distal portion of the wings 315A and 315B when the wings 315A and 315B are engaged with the slots 373A and 373B. The wire latch 340 can secure the animal mold 300 in place when the animal mold 300 is engaged with the gas block 390. The wire latch 340 can prevent distal movement of the wings 315A and 315B in order to prevent distal movement of the animal mold 300 when the wire latch 340 engages the animal mold 300. In some embodiments, the wire latch 340 can support the animal mold 300 without the use of the mold support 364.

Figure 39:
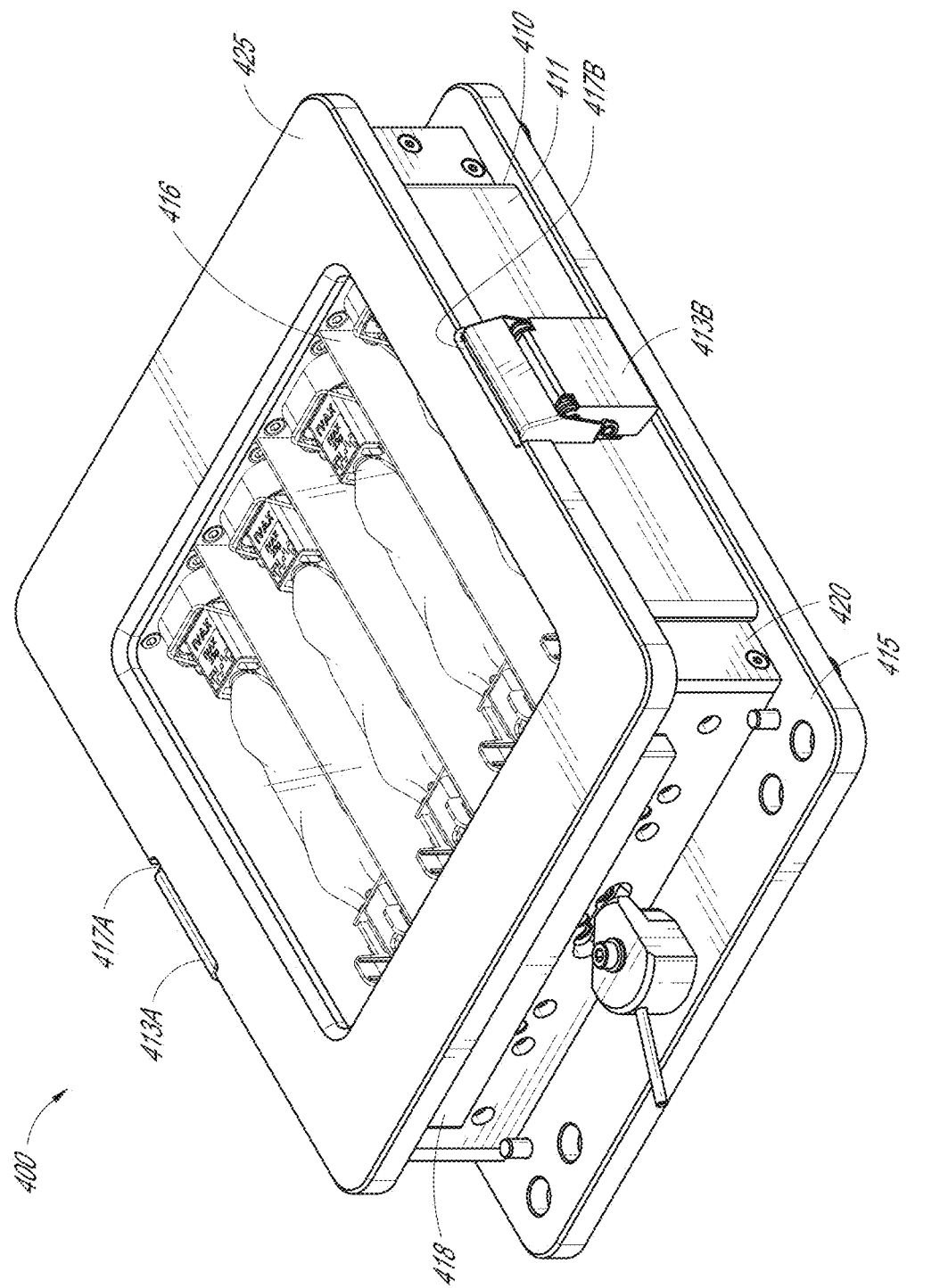
FIG. 39 depicts a perspective view of a gantry in a closed position in accordance with an illustrative embodiment.

FIG. 39 depicts a perspective view of an alternative embodiment of a two dimensional imaging gantry 400 in accordance with an illustrative embodiment of the present disclosure. The two dimensional imaging gantry 400 includes a lid 425 including a window 416 and recesses 417A and 417B. The gantry 400 further includes a docking interface 410 having a base plate 415, a first side wall 411 and a second side wall (not shown) positioned opposite the side wall 411. Latches 413A and 413B are secured to the second side wall and the first side wall 411, respectively. The latches 413A and 413B are configured to engage with the recesses 417A and 417B respectively, of lid 425 to secure the lid 425 to first side wall 411 and the second side wall. The gantry 400 further includes a holder 420 positioned on top of the bottom plate 415 and between the first side wall 411 and second side wall. The gantry 400 can also include a tail stop 418 configured to prevent a tail from an animal within the gantry from extending outside of the gantry.

Figure 40:
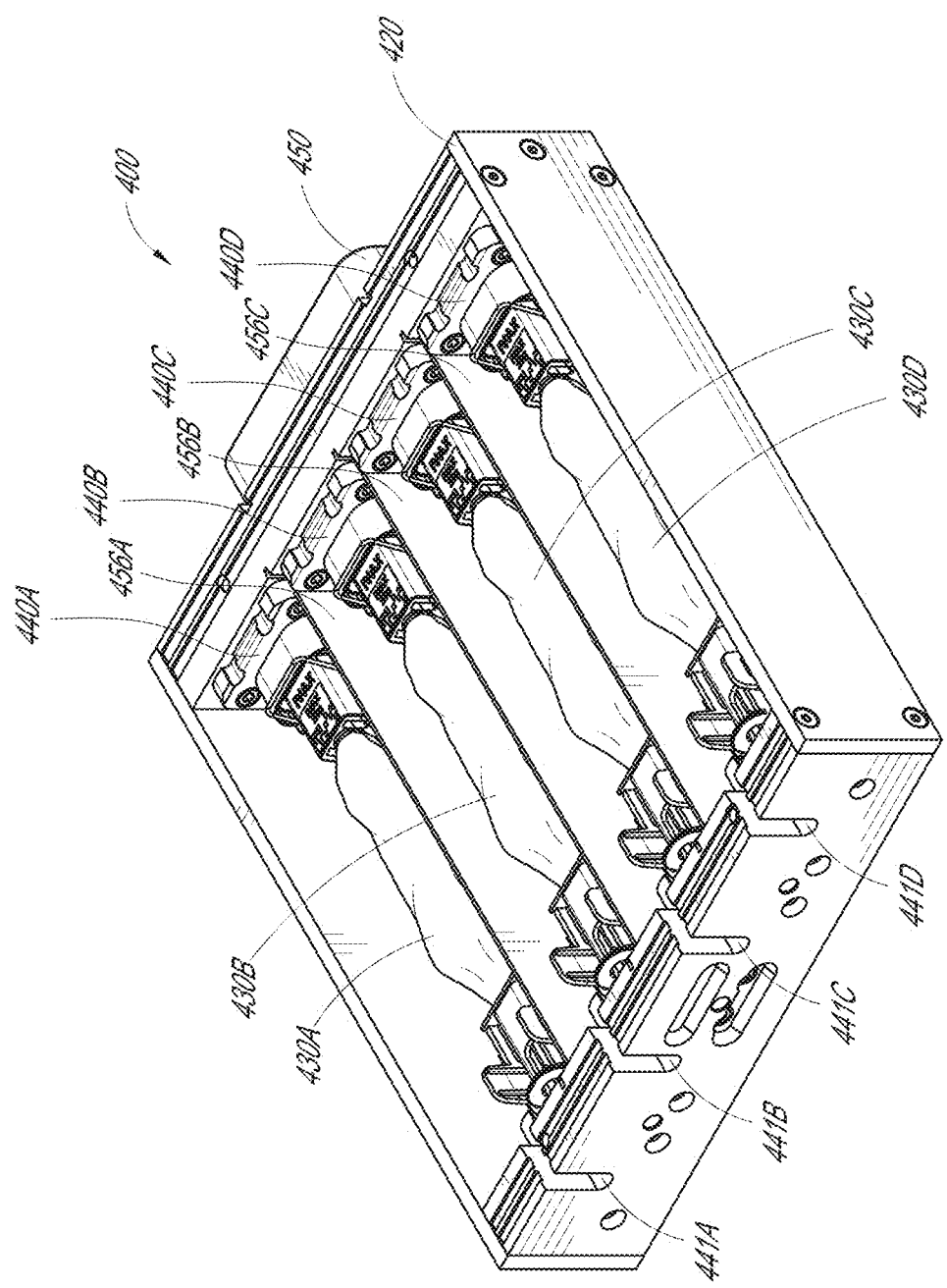
FIG. 40 depicts a perspective view of the gantry of FIG. 40 having several components removed in accordance with an illustrative embodiment.

FIG. 40 shows a perspective view of the gantry 400 with the lid 425, first side wall 411, second side wall, and tail stop removed. The holder 420 can be configured to secure a plurality of animal molds 430A-430D in position within the gantry 400. The animal molds 430A-430D can include the same components or generally similar components to the animal mold 300 described with respect to FIGS. 24-29. The holder 420 can further include a plurality of optical mirrors or optical blinds 456A-C, and a plurality of apertures 441A-D, each aperture configured to receive a tail of an animal in the molds 430A-D. The holder can further includes gas blocks 440A-D. Gas blocks 440A-D can include the same components or generally similar components to gas block 390 depicted in FIG. 38. In an alternative embodiment, the gas blocks 440A-D can include the same components or generally similar components to gas block 384 depicted in FIGS. 30-37.

Figure 41:
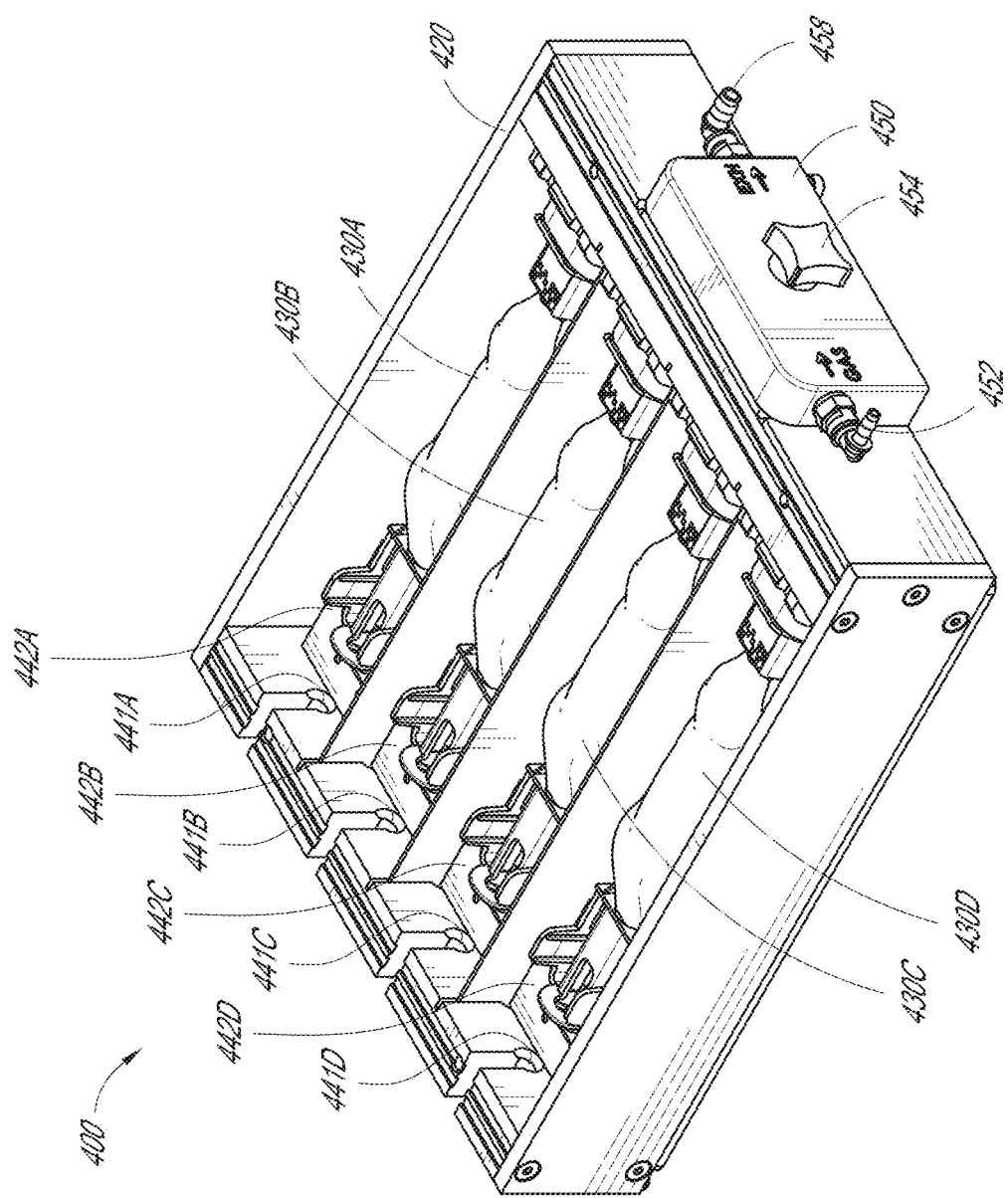
FIG. 41 depicts a perspective view of the gantry of FIG. 40 having several components removed in accordance with an illustrative embodiment.

FIG. 41 shows a perspective sectional view of the gantry 400 with the lid 425, first side wall 411, second side wall, and tail stop removed. The holder 420 further includes a plurality of mold supports 442A-D configured to engage and secure a distal end of the molds 430A-D. The mold supports 442A-D can include many similar components to the mold support 382 as depicted in FIGS. 30-37. For example, the mold supports 442A-D can include a recess and an aperture for receiving a fastener.

FIG. 41 further depicts a gas manifold 450 having a supply nozzle 452, a knob 454, and an output nozzle 458. The manifold 450 can include channeling for directing gas between the nozzles 452 and 458 and the animal molds 430A-D. The supply nozzle 452 can be configured to receive gas from an external source for supply to the gas blocks 440A-D and into the molds 430A-D. The output nozzle 458 can be configured to receive gas scavenged through scavenging passages of the animal molds 430A-430D for removal. The knob 454 can be configured to allow for the opening and/or closing of one or more channels within the manifold 450 to allow or prevent the flow of gas.

The gantry 400 can be secured to an imaging apparatus, in which the gantry 400 can be rotated by at least 180° in order to image the animals within the holder from at least two different views. In some embodiments, the gantry 400 allows for imaging of a dorsal view and a ventral view. In some embodiments, the gantry 400 allows for imaging of opposing lateral views. In some embodiments, the gantry 400 allows for imaging of a cranial view and a caudal view.

Figure 42:
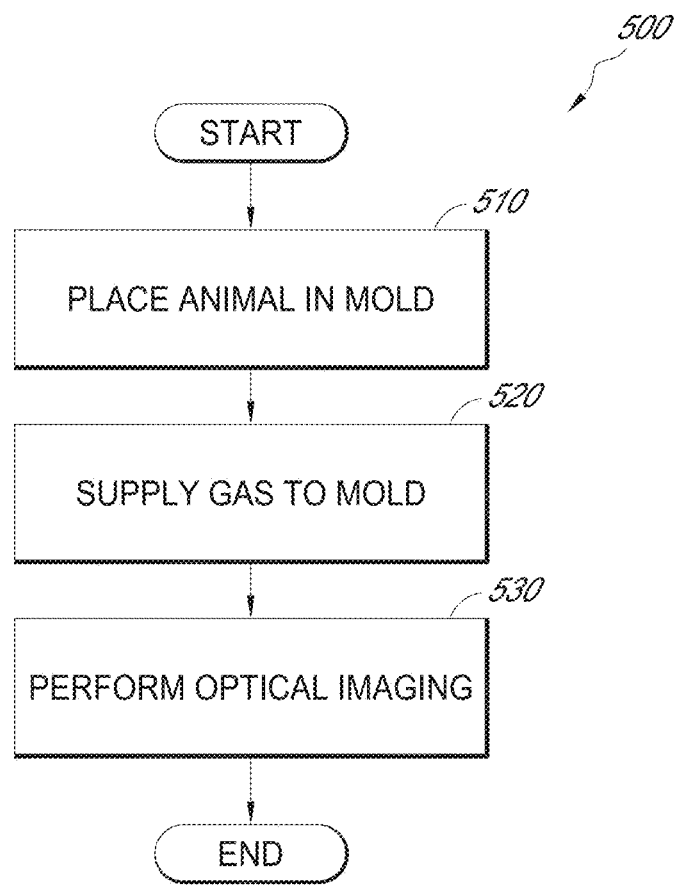
FIG. 42 depicts a flowchart of a process for collecting optical imaging data of an animal in accordance with an illustrative embodiment.

FIG. 42 depicts a flowchart of a process 500 for collecting optical imaging data of an animal in accordance with an illustrative embodiment of the present disclosure.

The process 500 beings at a step 510, wherein an animal is placed in an animal mold, such as animal molds 100 as depicted in FIGS. 1-10, animal mold 240 as depicted in FIGS. 20-23, animal mold 300 as depicted in FIGS. 24-30, or animal molds 440A-D as depicted in FIGS. 39-41. After the animal is placed in the animal mold, the animal mold by be moved from an open position to a closed position in order to at least partially immobilize the animal in a geometrically defined position. In some embodiments, the animal mold may be placed in a gantry, such as gantry 150 shown in FIGS. 11-19, gantry 200 shown in FIGS. 20-23, gantry 350 shown in FIGS. 31-38, or gantry 400 shown in FIGS. 39-41.

After the animal is placed in the animal mold, the process 500 moves to a step 520, wherein a gas, such as anesthesia, is supplied to the animal mold. The anesthesia can act to further immobilize the animal within the mold to prevent movement or distress while image is performed. The gas can be supplied to the animal mold from a gas supply, such as gas supply 281, gas supply nozzle 378, supply nozzle 452, or a gas supply bar, such as gas supply bar 250.

After gas is supplied to the animal mold, the process 500 moves to a step 530 wherein optical imaging is performed. Optical imaging can include two dimensional biolumines- cence imaging or three dimensional bioluminescence tomography. In some embodiments, after optical imaging is performed, data can be collected from one or more imaging devices and compared between two or more animals or between multiple images taken from the same animal.

The embodiments described herein can be used with image processing devices or systems for the collection and analysis of data related to an imaged animal. For example, the embodiments described herein can be used in with the image processing devices or systems described herein such as those shown and described with respect to FIGS. 43-54.

Figure 43:
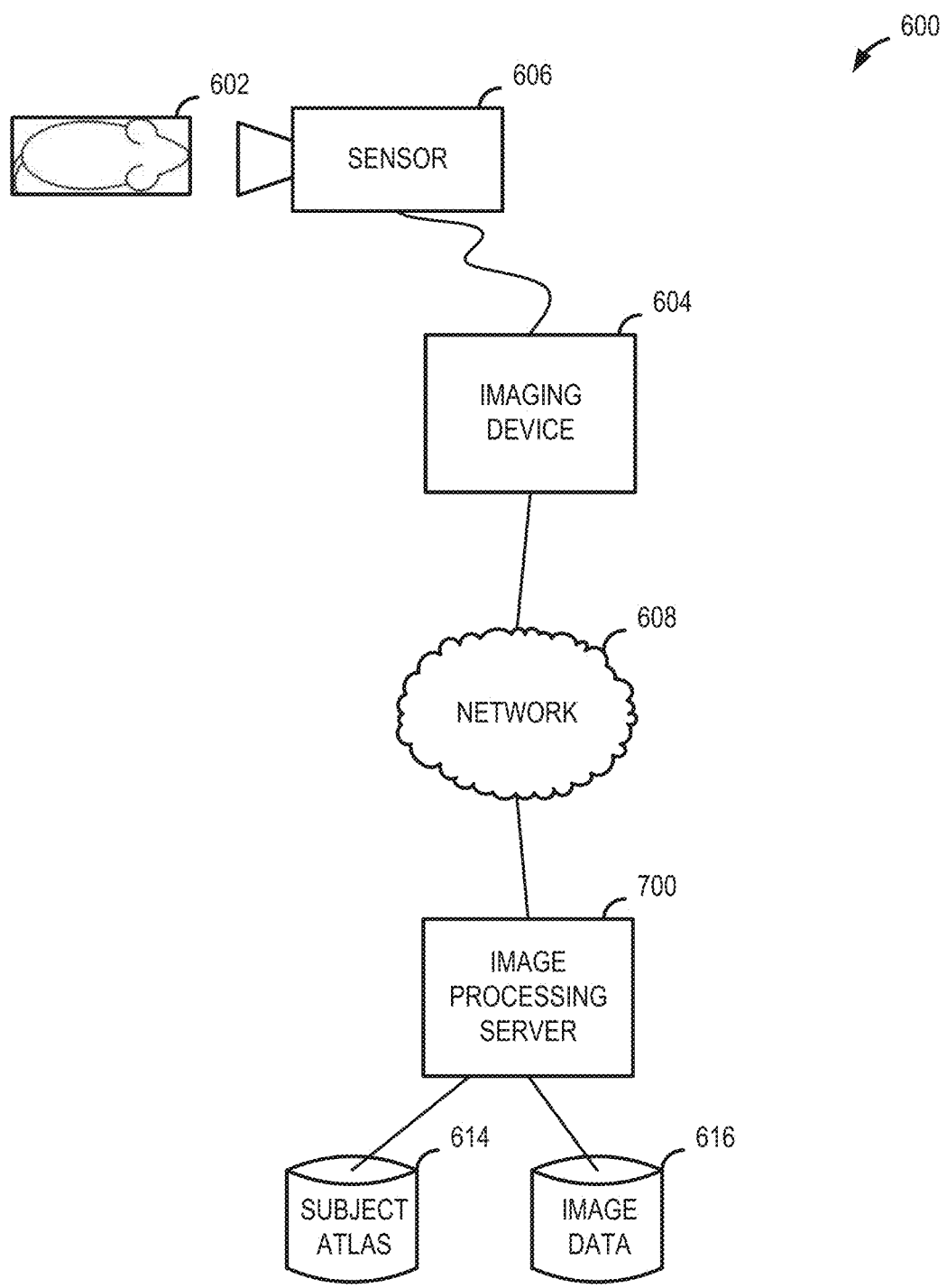
FIG. 43 shows a system diagram showing several components that may be included in a cross-correlation imaging system.

FIG. 43 is a system diagram showing several components that may be included in a cross-correlation imaging system. The system 600 may include a positioning assembly 602, an imaging device 604, and an image processing server 700. As shown in FIG. 43, the imaging device 604 and the image processing server 700 are in data communication via a network 608. The network 608 may include one or more of a LAN, WAN, cellular network, satellite network, and/or the Internet. Connection to the network 608 may be, for example, via a wired, wireless, or combination of wired and wireless, communication link. The communications via the network 608 may include messages. The messages may be formatted and transmitted according to a standardized pro- tocol such as TCP/IP, HTTP, FTP, or the like.

The positioning assembly 602 is configured to maintain a subject in a known pose. One example of a positioning assembly is a body-shape-conforming animal mold such as those described in U.S. patent application Ser. No. 14/319, 504 entitled "SYSTEM, METHOD AND COMPUTER-ACCESSIBLE MEDIUM FOR PROVIDING BODY-CON- FORMING ANIMAL BED, CALIBRATION CELL AND ORGAN PROBABILITY MAP FOR QUANTITATIVE OPTICAL IMAGING OF ANATOMICAL STRUC- TURES", the disclosure of which is incorporated by refer- ence in its entirety. The positioning assembly 602 may be implemented as a body conforming animal mold such as those shown and described herein with respect to FIGS. 1-42. To facilitate imaging, the positioning assembly 602 may be optically transparent. The subject, when placed into the positioning assembly 602, may be in an immobilized and geometrically defined position without the need for any additional surface registration hardware to detect the pose. As such, the positioning assembly 602 provides a defined geometry that can be detected. For example, in BLT experi- ments, the subject's surface geometry may need to be determined for proper light propagation modeling. The light propagation model may be based on simplified spherical harmonics ($SP_N$), which is a high-order transport that can be applied to the entire bioluminescence spectrum. This may afford a high level of quantification accuracy in the BLT experimental data. Including that the $SP_N$ solutions can increase the image processing accuracy over other imple- mentations, such as those relying on diffusion, when con- sidering strongly absorbing tissue.

The positioning assembly 602 and the subject therein may be detected using a sensor 606 coupled with or included in the imaging device 604. Examples of the sensor 606 include positron emission tomography, single photon emission counting tomography, magnetic resonance tomography, x-ray computed tomography, and optical fluorescence tomography. The sensor 606 may be configured to provide image data for cross-correlation as described herein. It will be understood that the imaging device 604 may be coupled with or include multiple sensors, of the same or different types.

The imaging device 604 may be configured to label image data files. For example, the image data files may be named using a convention that permits efficient identification of the experiment, subject, and/or imaging device. The imaging device 604 may be configured to bundle multiple image data files for transmission to the image processing server. The bundling may include collecting image data based on one or more of subject identifier, subject weight, spectral band, experimental notes, calibration files, time of luciferin injec- tion, imaging time, or some combination of one or more of these factors.

In some implementations, the imaging device 604 may include an interface to receive an input from a user indicat- ing the initiation of an imaging session. The imaging device 604 through a hardware and/or software add-on may be configured to provide image data to the image processing server 700. In such implementations, the imaging device 604 may receive an input indicating where the acquired image data should be saved. When a new dataset shows up in the specified location, the interface of the imaging device 604 may present an interface to receive information identifying a database line ID such as a mouse ID or calibration set) which with to associate the acquired image data and record this information in association with the image data. Once the acquisition is completed, the imaging device 604 may bundle the data stored in the specified location. The comple- tion of the acquisition may be specified, for example, through an additional input received by the imaging device 604. Upon completion of the bundling, the imaging device 604 may transmit the bundled image data to the image processing server 700 for further processing as described below. The image processing server 700 may store the received image data in the image data store 616.

Having the subject in a known pose may also permit generation of information used for the reconstruction and/or cross-correlation of experimental images prior to receiving an image for processing. For example, a kernel matrix may be used for recurring BLT imaging reconstructions. Gener- ating the kernel matrix may include using expectation-maximization (EM), an Algebraic Reconstruction Technique (ART), or other image reconstruction techniques. Generat- ing this kernel matrix can be resource intensive (e.g., time, power, processor, bandwidth, memory, etc.). As such, gen- erating the kernel matrix as part of image processing can introduce resource constrains on the system 700. In contrast, the described features allow the generation of an accurate kernel matrix for subsequent image data processing.

Having the subject in a known pose also enables the construction of a subject atlas for one or more subject types.

One example of a subject atlas is a mouse atlas. FIG. 43 shows a subject atlas data store 614 that may store subject atlas data used by the image processing server 610. The subject atlas data store 614 may include one or more position definitions. A position definition may identify, for a subject having certain attributes, one or more locations for features of interest. For example, for an animal subject, a position definition may indicate, for an animal in a known pose, where the animal subject's organ (e.g., liver) is located. In some implementations, a position definition may be represented as an organ probability map.

An organ probability map (OPM) may include a statistical representation of the 'average' spatial organ distribution of a given pool of animals with same or similar (e.g., within a tolerance) attributes such as body weight and gender while taking the biological variation across different animals into account. A particular position definition may be associated with a specific positioning assembly (e.g., body-shape-conforming animal mold) for a defined attribute (e.g., body weight). The atlas depends neither on posture registration hardware or complex deformation modeling, is operator-independent without manual surface alignment, and provides an instantaneous anatomical reference for the image reconstruction, such as BLT reconstruction. Some implementations of the OPM may include one thousand data points for each view of the subject (e.g., the animal holder can be rotated to image dorsal, ventral, and/or side views of the subject). For three-dimensional implementations, the OPM may include 10,000 data points. Thus, the imaging results provide a more realistic representation of the expected organ distribution than an atlas merely based on a single mouse. Furthermore, the surface shape of the OPM can be co-aligned with the positioning assembly and without the need for additional surface registration methods or manual observer interaction. Still further, where a study has a control and multiple cohorts with an N=10-50 and images captured more than 10 times yields millions of data points. Not only does this provide rich data, the data is also standardized for cross-correlation with data collected from previous or future studies.

Some cross-correlation implementations align a subject atlas either morphologically or by the aid of some additional registration hardware and software to the silhouette of a mouse with arbitrary posture and weight. However, these implementations may be computationally demanding because they uses an elastic tissue deformation model that overlays a digitally deformed mouse atlas with the measured surface geometry of each individual animal. Besides providing an anatomical reference for a given strain and body weight, the OPM may also provide spatially non-uniform optical parameter distributions of tissue that is needed for the light propagation model. The known absorption ($\mu_a$) and scattering ($\mu_s'$) coefficients of various organ tissue can be assigned to different locations (e.g., organs or other anatomical features) defined by the OPM.

For instance, in bioluminescence tomography experiments, having the subject in a known pose can also enables the use of non-uniform optical property maps for the BLT algorithm while significantly enhancing the image reconstruction accuracy. For example, because the experimental images are captured in a known pose, non-uniformities in the images can be accounted for based on the pose and attributes of the subject.

Further corrections to the captured experimental data can be achieved based on the pose and attributes of the subject. For example, a high-order transport model for light propagation can be used for the bioluminescence tomography analysis. The model may be generated using statistical Monte-Carlo methods or other computationally intensive photon transport methods (finite-difference or finite-element methods for solving the Boltzmann transport equation). Since an output of a model depends on the quality of the values input to the model, having well-defined and constrained inputs, such as those afforded by having the subject in a known pose and known attributes, can yield a more accurate model. Furthermore, the amount of computation needed for photon transport methods can be reduced. For example, the photon transport method for a subject imaged in a pose as described herein can be solved once to generate an image kernel for each animal pose. This can significantly reduce the computational burden of subsequent image reconstructions using the same image kernel.

The position definitions may be generated through direct measurement of subjects in the associated poses. In some implementations, the position definitions may be interpolated based on other pose definitions. For example, from a first position definition, a second position definition may be generated by scaling across subjects with different weights (e.g., 14 g-36 g) and/or within a similar weight range (±1 g), age, gender (male/female), strain, or other variable s of a subject.

As shown in FIG. 43, one positioning assembly 602 is provided. In some implementations, a set of positioning assemblies may be provided whereby each positioning assembly is associated with different attributes of a subject (e.g., weight, age, gender, strain, etc.).

The system 600 may also include an in vitro optical calibrator. The in vitro optical calibrator processes the experimental data captured to provide an output that mimics the average spectral optical properties of a mouse. The in vitro optical calibrator may enable the generation of a calibration factor needed for in vivo quantification of experimental values such as bacterial density. In one implementation, the in vitro optical calibrator enables the translation of a physical quantity (e.g., photons $cm^3 \ s^{-1}$) into a biologically relevant quantity (e.g., number of colony forming units (CFU) number of cancer cells, etc.). Some BLI systems are configured to measure the light intensity (photons $s^{-1} \ cm^{-2}$) at the tissue surface. However, this intensity at the tissue surface may not provide an accurate and/or direct determination of a biologically relevant quantity (e.g., the bacterial density ($CFU/mm^3$)) of the tissue. The in vivo bacterial density calculation may include a calibration factor to transform the physical quantity (e.g., photons $s^{-1} \ cm^{-3}$) into the sought biological indicia (e.g., CFU count). Such calibration factor can be determined with the in vitro optical calibrator. The in vitro optical calibrator may include of synthetic tissue phantom material that mimics some average optical tissue properties at four different spectral windows of the bioluminescence spectrum. The calibration factor may then be generated by using a known amount of CFU placed inside the calibrator and reconstructing its photon emission density.

In some implementations, the system 600 may be portable and configured to be plugged into an optical small animal imaging system. Bioluminescence images may be bundled and sent by the system to a centralized image processing server via a network. The image processing server may be configured to perform the BLT reconstruction and automated image analysis software. The image processing server maybe configured to generate a final and comprehensive study report. The report may be automatically transmitted to a user device such as the imaging device, hardware add-on/retrofit thereof, or other computing device.

Figure 44:
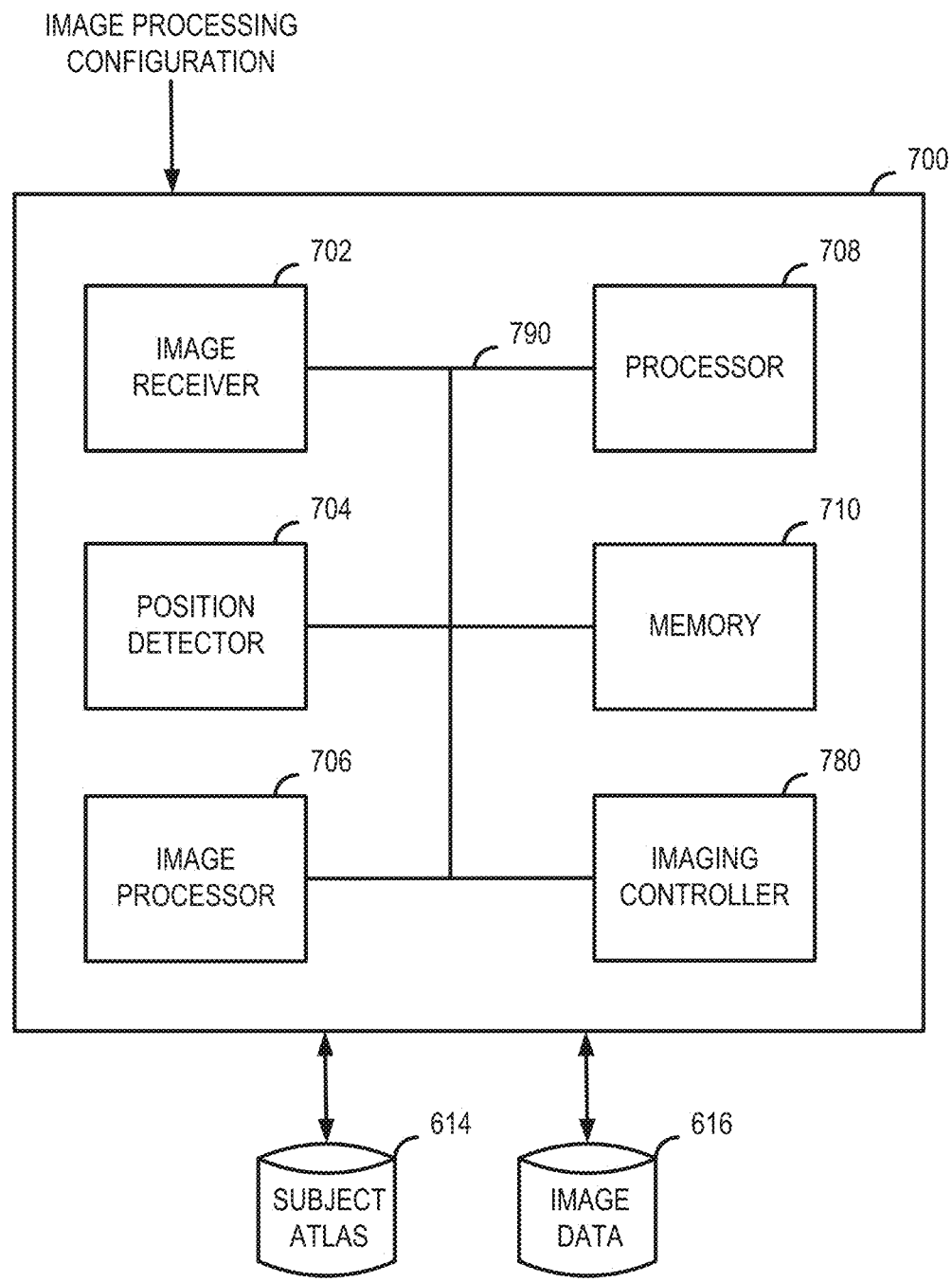
FIG. 44 shows a functional block diagram showing an example image processing server.

FIG. 44 shows a functional block diagram showing an example image processing server. The image processing server 700 includes an image receiver 702, a position detector 704, an image processor 706, a processing unit 708, a memory 710, and an imaging controller 780. The elements included in the image processing server 700 may be coupled by a bus 790. The bus 790 may be a data bus, communication bus, or other bus mechanism to enable the various components of the image processing server 700 to exchange resources (e.g., power) and/or information.

The processing unit 708 may be configured to coordinate the activities of the image processing server 700. For example, an image may be received by the image receiver 702. The image receiver 702 may obtain the image data for the image and receive instructions from the processing unit 708 indicating where the image data should be sent (e.g., memory 710, image data store 616, image processor 706, etc.). In some implementations, the image receiver 702 may forward the image data to the processing unit 708 for further processing.

The image receiver 702 may be configured to receive the image data via wired, wireless, or hybrid wired-wireless channels. The image data received by image receiver 702 may include two-dimensional image data or three-dimensional image data. In some implementations, the image receiver 702 may receive information about the imaging device and/or sensor that generated the image data. The image receiver 702 may be configured to receive image data represented in a variety of machine-readable formats such as JPG, TIFF, GIF, SVG, PNG, XML, DICOM, or the like. The image data may include a representation of a single image or of a series of images (e.g., video, time lapse sequence, etc.).

An image data set may include or be accompanied by meta data. The meta data may include information which further describes the experimental setting, the animal (e.g., age, weight, sex), the administered therapy, the instrument settings (e.g., focal length, shutter time, F-ratio), project name, study time point, or the like.

The position detector 704 may be configured to identify a position of a subject shown in an image included in the image data. In some implementations, the position detector 704 may identify the position through analysis of an image included in the image data. For example, the image may include a machine readable identifier (e.g., barcode, QR code, icon, graphic, text). Embodiments of a machine readable identifier are described herein with respect to FIGS. 24-41. The identifier may be associated with a particular positioning assembly. By identifying the positioning assembly used when capturing the image, the position may be identified. The identification process may include querying the subject atlas data store 614 or other data storage device that includes a data record associating the machine readable identifier with a positioning assembly. In some implementations, an image processing configuration may be provided to the image processing server 700. The image processing configuration may include the associations between the identifier and the positioning assembly.

The position detector 704 may receive a message from the processing unit 708 to initiate position detection for an image identified in the message. The identification of the image may be through a unique image identifier that can be used to identify the image data including the image within the image data store 616. In some implementations, it may be desirable to include the position information with the image data (e.g., as metadata). In such implementations, the position information for the image data may be generated using image data stored in a buffer or the memory 710 before storage in the image data store 616. In such implementations, the processing unit 708 may provide a memory location from which the position detector 704 can access the image data to be analyzed.

The position detector 704 may be calibrated prior to an imaging session. The calibration may utilize a calibration device (not shown). The calibration device may include unique image position identifiers that can be correlated with position information detected by the position detector 704. The spatial location of the calibration image identifiers may be stored on a storage device and made available for use for subsequent imaging sessions.

The image processor 706 is configured to process image data to generate an imaging result. The image processor 706 may receive a message from the processing unit 708 that image data is available for processing. The message may include information the image processor 706 is configured to use to obtain the image data. The information may include an identifier for the image data or a memory location where the image data is located. In some implementations, the image processor 706 may be configured to monitor a memory location for arriving image data. For example, a directory may be specified within the memory 710 where image data (or identifiers therefor) that is ready for processing is placed. As the image processor 706 generates imaging results for the respective images, the image data may be removed from the directory. The directory may be specified via the image processing configuration. The imaging results may be stored in the image data store 616 in association with the image data.

The image processor 706 may be configured to obtain a processing protocol to process the image data. Because the image processing server 700 may be used to process image data from a variety of sources, for a variety of experiments, processing protocols may be provided to allow dynamic adjustment of the image processing server 700 to analyze different image data. A processing protocol may be specific to one or more of: an experiment, an image data type, a positioning assembly, a location, or other feature detectable by or provided to the image processing server 700.

For an identified experiment and image data type, the processing protocol may identify a portion of the image data the image processor 706 may use for generating the image processing result. For example, in an experiment testing delivery of a drug to the liver, it may be desirable to focus the image data processing on the portion of the image data corresponding to the liver.

The processing protocol may indicate specific values for processing the image data. For example, it may be desirable to provide imaging results that indicate levels of bacteria within an area. The levels may be identified as ranges of values. These ranges of values may be specified using the processing protocol. Accordingly, when the image processor 706 analyzes image data at a location, the output of the analysis uses the image data as categorized into one of the ranges.

It will be appreciated that in addition to specific values, the combination of values may also be specified using a processing protocol. For example, it may be desirable to provide a ratio of values between two locations of the image.

The image processor 706 may also be configured to cross-correlate image data between two or more images. For example, in a time series study, it may be desirable to track a change at a location for a subject over time. The processing protocol may identify which images to use (e.g., which of the images in a sequence of images) and a comparison to perform for the image data. As another example, in a multi-modality study, two or more types of image data may be collected. The image data may not readily combine to provide an imaging result. A processing protocol may be specified to indicate how, for example, MRI image data may be cross-correlated with spectral image data.

The image processor 706 may use the position information identified by the position detector 704 to process the image data. The image processor 706 may identify the portion of the image data specified by the processing protocol based on the position information. Several non-limiting advantages of image data processing based on position information are described in further detail below.

The image processing server 700 may be configured to guide the collection of image data. The imaging controller 780 may generate configuration instructions to adjust an imaging device. The adjustment may allow the imaging device or sensor coupled therewith to accurately capture the image data needed for an experiment. For example, an image may be captured that shows the entire subject. However, the area of interest for the experiment may be the head. In such instances, the imaging controller 780 may receive a configuration request from the imaging device. The request may indicate the experiment, the imaging device, and a subject to be imaged. In some implementations, the request may include an image of the subject within the positioning assembly. Using the provided information, the imaging controller 780 may identify the position of the subject to be imaged. Based on the position and the desired anatomical feature to be imaged, the imaging controller 780 may identify an area of the subject where the imaging device will obtain data. With the area determined, the imaging controller 780 may then generate a specific command to cause adjustment of the imaging device for capturing the desired image data for the identified area.

The memory 710 may contain computer program instructions that the processing unit 708 executes in order to implement one or more embodiments. The memory 710 may include random access memory, read only memory, and/or other persistent, non-transitory computer readable media. In some implementations, the memory 710 may be implemented in whole or in part as a remote memory device (e.g., at a network location in data communication with the image processing server 700). The memory 710 can store an operating system that provides computer program instructions for use by the processing unit 708 or other elements included in the image processing server in the general administration and operation of the image processing server 700. The memory 710 can further include computer program instructions and other information for implementing aspects of the present disclosure.

Figure 45:
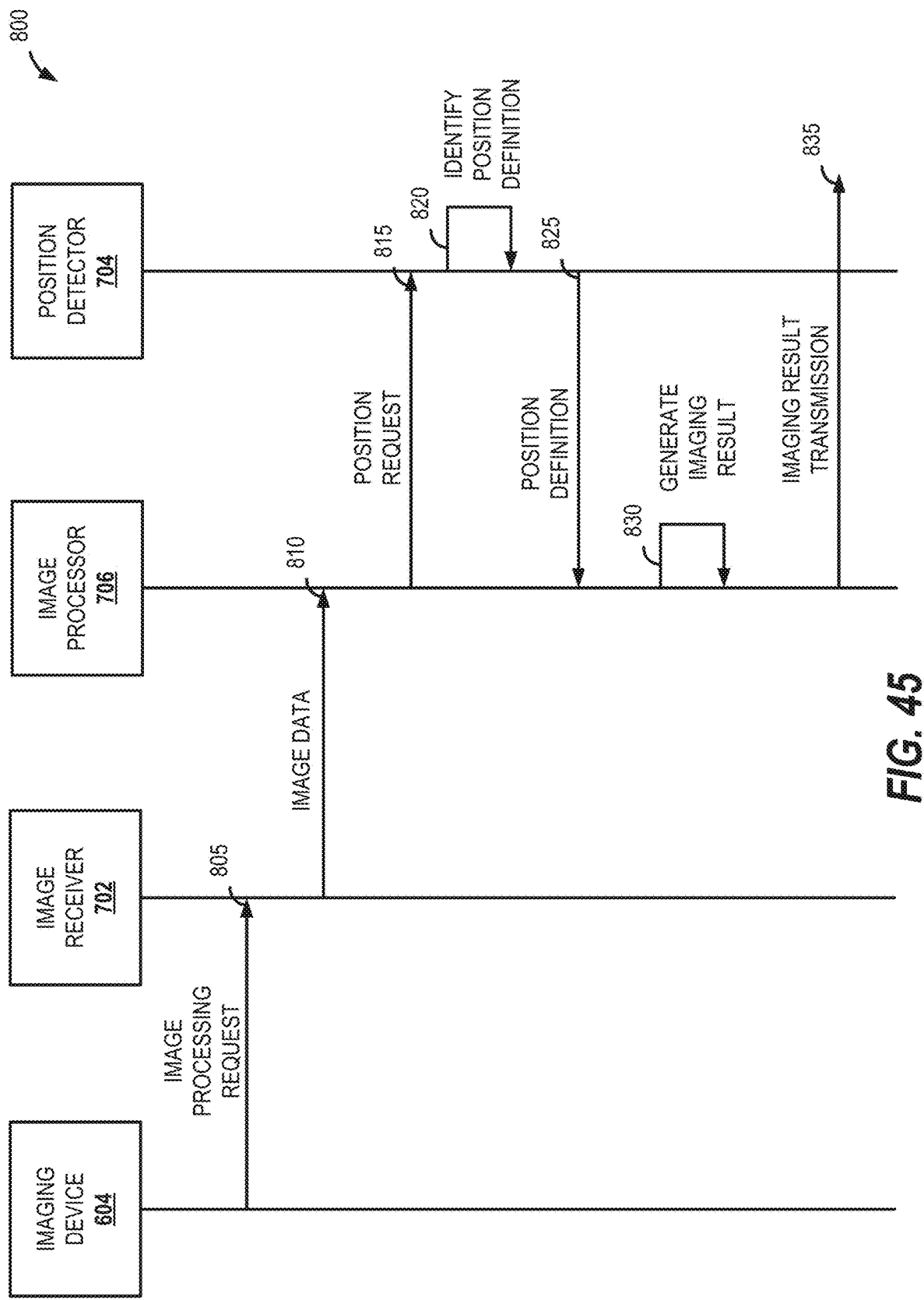
FIG. 45 shows a message flow diagram for an example position based image processing.

FIG. 45 shows a message flow diagram for an example position based image processing. For example, the message flow 800 shown in FIG. 45 illustrates how image data may be received by an image processing server to generate an image processing result. The message flow 800 shown in FIG. 45 provides a simplified view of messages that may be exchanged between the entities shown for position based image processing. It will be understood that additional entities may mediate one or more of the messages shown in FIG. 45.

An image processing request message 805 may be transmitted from an imaging device 604 to the image receiver 702 included in the image processing server 700. The imaging device 604 may include a hardware adapter configured to transmit the image processing request message. The image processing request message may include information identifying one or more of: an experiment, a subject, the imaging device 604, images, text, audio, a reference to the image data (e.g., network location, uniform resource locator), a sensor used to obtain the image data, security/authorization information (e.g., a token), conditions at the imaging device 604 (e.g., temperature, humidity, pressure, light level, sound level), conditions of the imaging device 604 (e.g., resource levels (e.g., power, fluid or other experimental materials), time since last maintenance, available sensors, etc.), conditions of the sensor used to generate the image data (e.g., resource levels, time since last maintenance, capture settings), and the like. Collectively, this information may be referred to as "image data."

The image receiver 702 may determine the message 805 is an image processing request message based on information included in the message 805. The image receiver 702 may then send a message 810 to the image processor 706 including the image data or a reference to the image data to be processed. The image processor 706 may provide a position request message 815 to the position detector 704. The position request message 815 may include all or a portion of the image data received from the image receiver 702. In some implementations, the image processor 706 may perform preliminary processing of the image data to extract a portion of the image data that identifies the positioning assembly used to capture the image data. This may include identifying a portion of the image data including a machine readable identifier for the positioning assembly.

Via messaging 820, using at least some of the information included in the position request message 815, the position detector 704 identifies the position definition corresponding to the request 815. The identification may include querying the subject atlas data store 614 or other data storage device that includes a data record associating the machine readable identifier with a positioning assembly. In some implementations, an image processing configuration may be provided to the image processing server 700. The image processing configuration may include the associations between the identifier included in the image data and the positioning assembly.

The identified position definition is then transmitted via a position definition message 825 to the image processor 706. In some implementations, the image processing server 700 may be processing multiple images. In such implementations, it may be desirable to include information to distinguish message flows for respective image data. The position definition message 825 may include an identifier to facilitate coordinate of a response with a particular request. The identifier may be specific to the overall image processing flow or to a portion of the processing flow such as the position request.

Via messaging 830, the image processor 706 generates an imaging result. The image processor 706 may generate the imaging result based on the position definition received via the position definition message 825. The image processor 706 may be configured to identify a processing protocol using one or more of the image data, the detected position, and the position definition. As discussed above, the processing protocol may identify which values to use for generating the imaging result. The processing protocol may identify how to combine or compare the values for generating the imaging result. The processing protocol may identify a desired output for the imaging result (e.g., text, image, data plot, etc.). In some implementations, the processing protocol may identify one or more destinations for the imaging result. For example, it may be desirable to deliver the imaging result to an electronic communication device associated with a researcher for the experiment. This may include generating and transmitting an email message, a text message, a multimedia messaging server message, a fax message, or other digital communication for delivery to the identified destination(s).

As shown in FIG. 45, the image processor 706 provide an imaging result transmission message 835 to a destination, such as the destination specified in the processing protocol. In some implementations, the imaging result transmission message 835 may be stored for presentation in response to a request. For example, the imaging result transmission message 835 may include a report. The report may be published and made available through a web-server. A researcher using an electronic device connected to a network may access the web-server and request presentation of the report.

Figure 46:
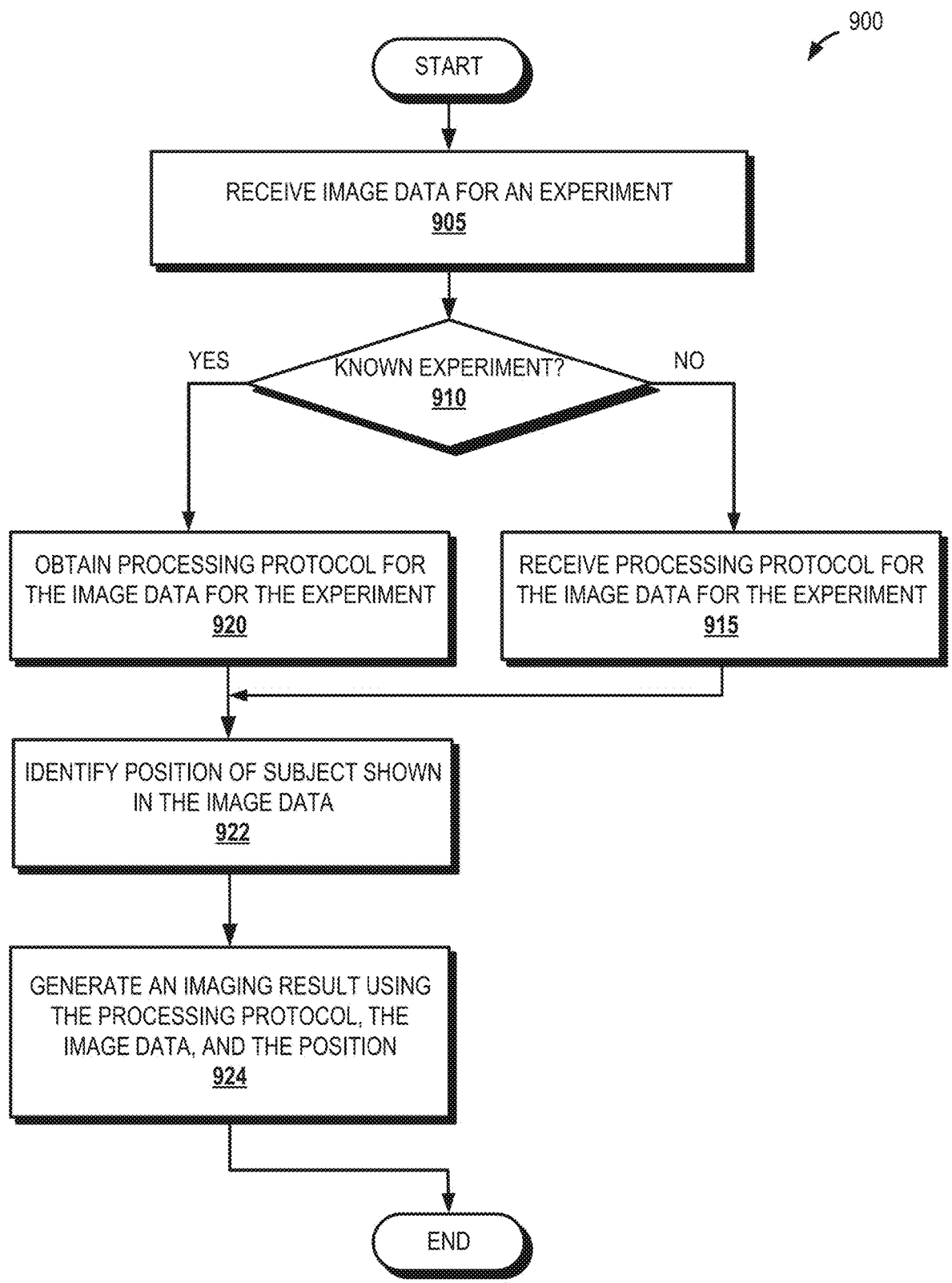
FIG. 46 shows a process flow diagram for an example method of generating an imaging result.

FIG. 46 shows a process flow diagram for an example method of generating an imaging result. The method 900 may be implemented in whole or in part by one or more of the devices described in this application such as the image processing server 700 shown in FIG. 43 or FIG. 44. In some implementations, the method 900 may be implemented on device that includes an integrated global memory shared by a plurality of programmable compute units that includes a buffer, wherein the buffer may include a first-in-first-out (FIFO) buffer. The device may further include an integrated circuit (IC) that may include at least one processor or processor circuit (e.g., a central processing unit (CPU)) and/or an image processing unit (IPU), wherein the IPU may include one or more programmable compute units.

At block 905, image data for an experiment is received. The image data may be received from an imaging device, such as the imaging device 604. The image data may be received via wired, wireless, or hybrid wired-wireless channels. The image data may be received by an image data receiver, such as the image receiver 702. Receiving the image may include receiving a machine-readable message including the image data. The image data may include an identifier for the experiment. This identifier may be used to determine how the image data should be processed.

At block 910, a determination is made as to whether the experiment associated with the image data is known. For example, a processing protocol may be stored in a data storage device in communication with the image processing server. In some implementations, the processing protocol may be specified using the image processing server configuration. The processing protocol may be stored in association with an identifier for the experiment. The determination at block 910 may include accessing the data source for processing protocols to determine whether the experiment has a defined processing protocol.

If the determination at block 910 is negative, at block 915, processing protocol information for the experiment is received. The processing protocol information may be included in a message. It may be desirable to include an identifier for the experiment along with the processing protocol information in the message. The message may be received via a user interface (e.g., web-page, client application, etc.). The processing protocol information may be received via wired, wireless, or hybrid wired-wireless channels. In some implementations, the processing protocol information may be received via a protocol definition file. The protocol definition file may be a structured data file including the information specifying one or more of: which image data is used for processing, how the image data is combined or compared, output for the imaging result, and destination for the imaging result. At block 915, the received processing protocol information may be validated. For example, the type of image data included in the protocol (e.g., MRI information) may be unavailable from the identified image sources (e.g., X-ray images). In such implementations, an indication of the invalid information may be provided.

Once a valid processing protocol is defined (e.g., block 915) for the experiment, or previously defined (e.g., affirmative determination at block 910), at block 920, the processing protocol for the image data for the experiment is obtained. The processing protocol may be obtained from a data storage device configured to persist the processing protocol information. For example, the image processor 706 may query a data store using the experiment identifier for the processing protocol. In some implementations, an experiment may be associated with multiple processing protocols. The respective protocols may be defined for image types, subject types, or other variables within the experiment. In such implementations, the query may include the additional information to identify the applicable processing protocol for the received image data and experiment. In some implementations, it may be desirable to identify multiple processing protocols for processing image data. For example, a general purpose data collection processing protocol may be associated with the experiment along with an image data type specific processing protocol. In such implementations, the processing protocols may be associated with a priority such that when multiple processing protocols are identified for image data for an experiment, the order in which the processing protocols are executed can be determined based on the priority (e.g., higher priority protocols are executed before lower priority protocols).

Figure 47:
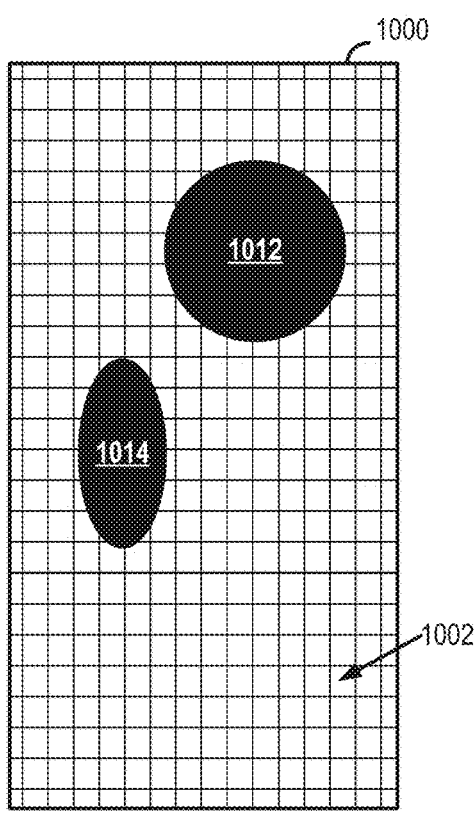
FIG. 47 shows an example of an analysis grid that may be included a processing protocol.

FIG. 47 shows an example of an analysis grid that may be associated with a processing protocol. The analysis grid 1000 may define a division for an image into discrete units. One unit 1002 is labeled in FIG. 47. For two dimensional image data, the unit 1002 may represent a pixel. For three dimensional image data, the unit 1002 may represent a voxel. The analysis grid 1000 may further define areas of interest. The areas of interest define specific units from an image that will be used to analyze the image. As shown in FIG. 47, a first area of interest 1012 and a second area of interest 1104 are defined. It will be appreciated that an analysis grid may define only one area of interest or more than two areas of interest depending on the image analysis to be performed.

In some implementations, the processing protocol may indicate an anatomical feature of interest (e.g., liver). In such implementations, the anatomical feature of interest may be used to generate an analysis grid. For example, a subject atlas may include modeling information for the anatomy of a subject having certain attributes (e.g., strain, gender, age, etc.). The modeling information may include identifiers associated with location information for specific anatomical features such as named organs, vascular structures, skeletal structures, and the like. Using the anatomical feature indicated in the processing protocol and a subject atlas, specific location information may be determined for the feature within the subject.

Returning to FIG. 46, at block 922, a position of a subject shown in the image data is determined. The position may be determined by providing all or a portion of the image data to a position detector, such as the position detector 704. The identification may be based on information indicating the positioning assembly used for capturing the image data. For example, an identifiable mark may be placed on a mold in which an animal subject was placed to capture the image data.

Identifying the position may include identifying a position definition for the positioning assembly. Once the position definition is identified, the position of the subject shown in the image data may be assessed by correlating the image data with the position definition. The correlation may include aligning the position definition with the image data. For example, the position definition may include identification of a head of the subject. The portion of the position definition corresponding to the head may be aligned with the portion of the image data showing the head. The alignment may include rotating the image data (e.g., 90 degrees, 180 degrees, 270 degrees), scaling the image data, transposing the image data, or the like.

Figure 48:
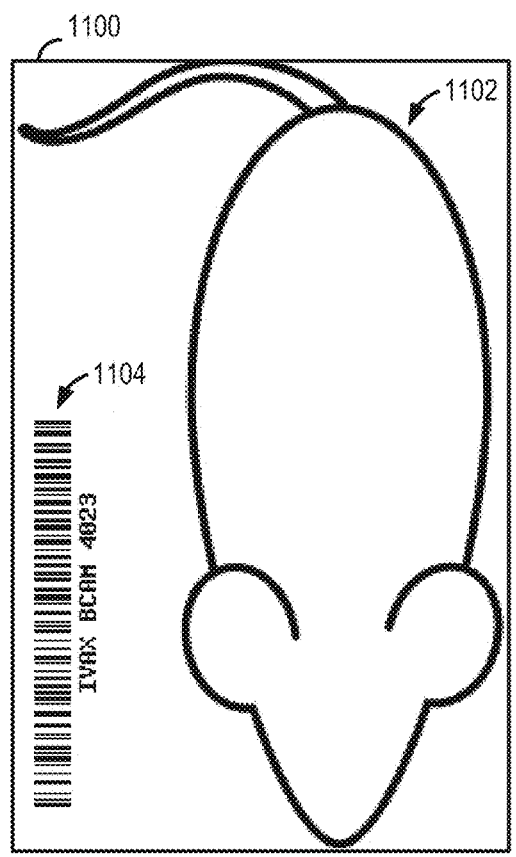
FIG. 48 shows an example of an image of a subject that may be included in the image data.

FIG. 48 shows an example of an image of a subject that may be included in the image data. The image 1100 includes an ordered group of pixels. The pixels include color information that cause representations of shapes to be shown. The image 1100 shows a representation of a subject 1102. The subject 1102 shown in the example of FIG. 48 is a mouse. The image 1100 also shows a representation of a positioning assembly identifier 1104. As shown in FIG. 48, the positioning assembly identifier 1104 includes a barcode and textual information. The positioning assembly identifier 1104 may be used to determine which positioning assembly was used for retaining the subject 1102 shown in the image 1100.

Returning to FIG. 46, at block 922, a positioning assembly identifier, such as the positioning assembly identifier 1104, may be used to determine the position of the subject.

At block 924, an imaging result is generated using the processing protocol, the image data, and the position information. Generating the imaging result may include generating a graphical result, textual result, data plot, or other output representing features identified using the image data. The generating may include identifying a portion of the image data based on the processing protocol and the position information. For example, the processing protocol may be defined to process color intensity at a specific location (e.g., brain) of the subject shown in an image included in the image data. Generating the image result may include parsing the image to include only the portions including the feature of interest for further processing. This can reduce the amount of resources needed to process the image data as only the portions of the image data relevant to the processing protocol may be processed.

Generating the imaging result may include determining the location identified in the processing protocol refers to a pixel location. The imaging result may be generated using the pixel information at an identified location in the first image. Generating the imaging result may include determining the location identified in the processing protocol refers to a voxel location. The imaging result may be generated using the voxel information at an identified location in the first image. The processing protocol may indicate how the information at the specified location is to be analyzed. For example the processing protocol may indicate one or more of: thresholds for comparison, ranges for comparison, or an equation with variables for representing a relationship for the information. In some implementations the processing protocol may identify a remote service for obtaining the imaging result. For example, a researcher may provide a server with custom analytical service interface. The image data or identified information for a specific location may be provided via this interface to obtain, in response, the imaging result.

Figure 49:
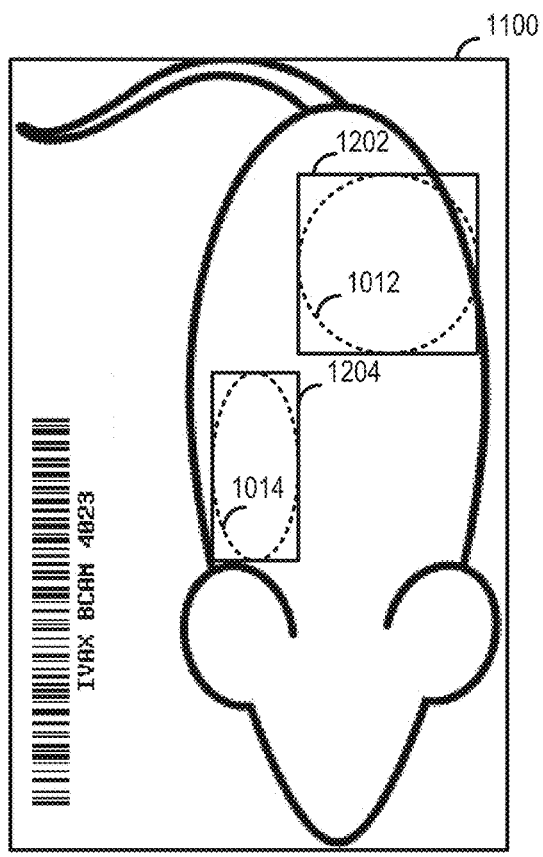
FIG. 49 shows an overlay diagram for the example image of FIG. 48 overlaid with the analysis grid of FIG. 47.

FIG. 49 shows an overlay diagram for the example image of FIG. 48 overlaid with the analysis grid of FIG. 47. As shown in FIG. 49, the first area of interest 1012 and the second area of interest 1014 are located within the image 1100. Using these areas of interest, a first image portion 1202 including image data for the first area of interest 1012 may be identified and a second image portion 1204 including image data for the second area of interest 1014 may be identified. In some implementations, the first image portion 1202 and the second image portion 1204 may be used to generate smaller files for further image processing.

The processing protocol may include configuration information to indicate how the data represented in the portions are to be analyzed. For example, using the first image portion 1202, if the metric of interest is color intensity, the processing protocol may direct the image processor 706 to process each pixel included in the first image portion 1202 to generate an average color intensity shown in the first image portion 1202.

As another example, using the first image portion 1202, where the image 1100 is a three dimensional image, the metric of interest may be to identify a total area having a minimum color intensity. In such implementations, the processing protocol may direct the image processor to count the number of voxels included in the first image portion 1202 forming a contiguous area having the minimum color intensity. Furthermore, the mean, median, or maximum value of color intensity can be determined for a region of interest.

A region-of-interest (ROI) can be automatically determined by the system, without any operator bias. For example, the ROI may be determined by calculating an average image of color intensities using a pool of individual images with different color intensities. The spatial distribution of color intensities may be transformed into a map of intensity probabilities for each individual image. An intensity probability map may describe the distribution of likelihood of the occurrence of color intensity. For example, a large color intensity value may be directly correlated with a large intensity probability, whereas a small color intensity may be correlated with a small intensity probability. It may be desirable to have the total sum of all intensity probabilities of each individual image be "1." The average intensity probability map may be calculated by averaging the probability for each pixel/voxel. In an average intensity probability map, it may be desirable for the total sum of probability be "1."

An ROI can be determined automatically by selecting pixels/voxels with the largest intensity probabilities. For example, when processing bioluminescence image data, intensity probabilities can equate to the highest probability of light emission of the image, and hence can be considered as an indicator for a ROI.

The method 900 generally describes how an imaging result may be generated for image data based on the information included image data. In some implementations, it may be desirable to compare information from image data captured at different times and/or by different sensors. For example, an imaging device may include two sensors each configured to detect different properties for a subject. In such implementations, image data may be received from each sensor. As another example, an experiment may wish to track efficacy of a drug over time or between a control subject and a subject exposed to a drug. An imaging result generated from multiple, differing image data may generally be referred to as a cross-correlated imaging result.

Figure 50:
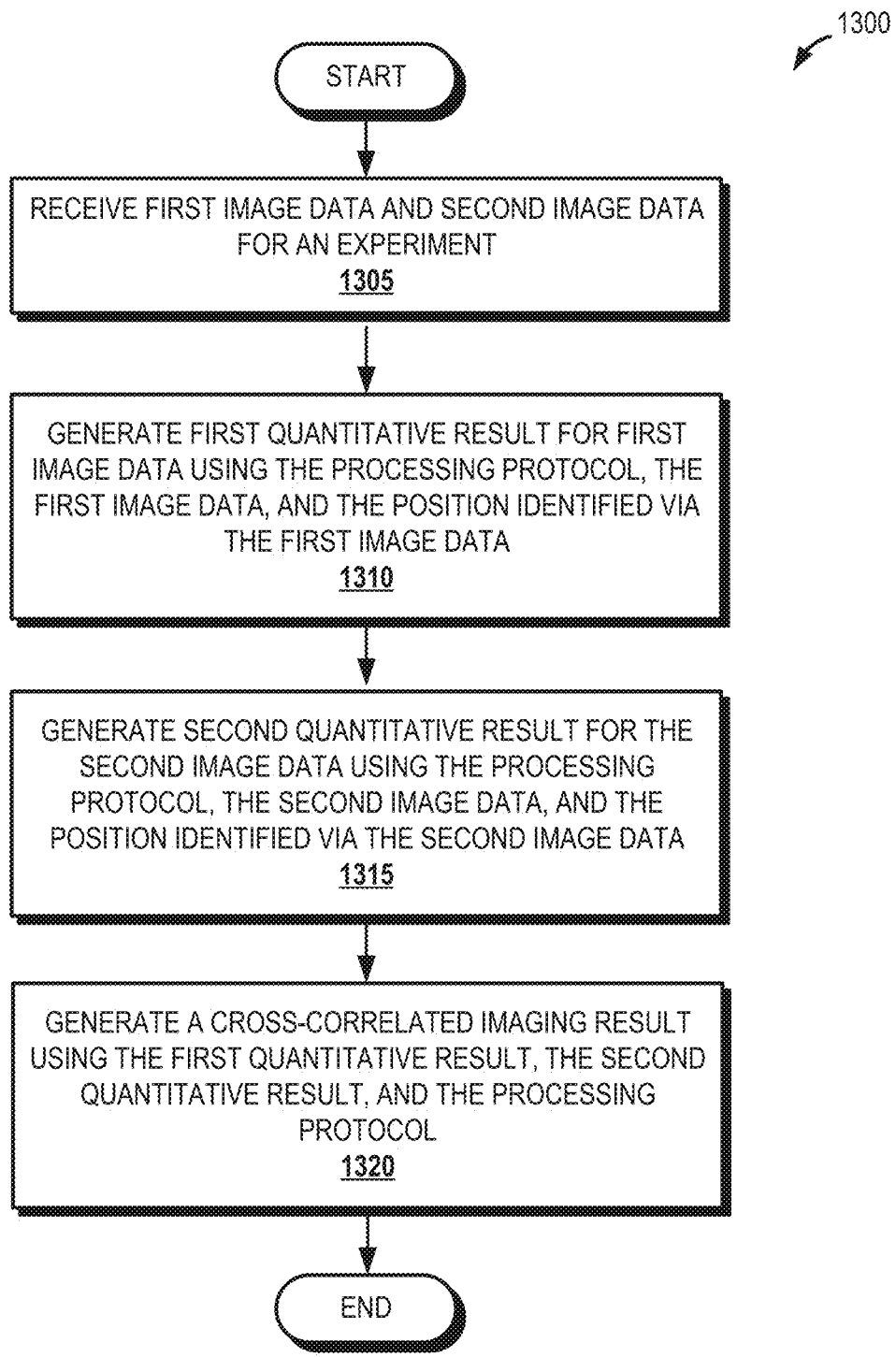
FIG. 50 shows a process flow diagram for an example method of generating a cross-correlated imaging result.

FIG. 50 shows a process flow diagram for an example method of generating a cross-correlated imaging result. The method 1300 may be implemented in whole or in part by one or more of the devices described in this application such as the image processing server 700 shown in FIG. 43 or FIG. 44. In some implementations, the method 1300 may be implemented on device that includes an integrated global memory shared by a plurality of programmable compute units that includes a buffer, wherein the buffer may include a first-in-first-out (FIFO) buffer. The device may further include an integrated circuit (IC) that may include at least one processor or processor circuit (e.g., a central processing unit (CPU)) and/or an image processing unit (IPU), wherein the IPU may include one or more programmable compute units.

At block 1305, first image data and second image data for an experiment is received. The first image data and second image data may be received in a single message or via separate messages. As discussed above, the first image data may differ from the second image data in one or more ways such as capture modality, capture time, subject imaged, position of the subject, or the like. The first image data and the second image data may be received from the same imaging device or from two different imaging devices. The image data may be received by an image data receiver, such as the image receiver 702. Receiving the image may include receiving a machine-readable message including the image data. The first image data and the second image data may each include an identifier for the experiment. This identifier may be used to determine how the respective image data should be processed.

At block 1310, a first quantitative result is generated for the first image data. Generating the first quantitative result may include correcting the light intensity for a portion of the first image data. For example, light intensity at a portion of the image data showing the tissue surface may be corrected. The correction may be based on light exit angle relative to the imaging plane. In this way, light intensities with a large exit angle that appear to be smaller in the uncorrected first image data, can be adjusted to provide a more accurate intensity value. At block 1315, a second quantitative result is generated for the second image data. The generating at block 1315 may be similar to the generating at block 1310. The first quantitative result may be generated by processing the first image data using the method 900 shown in FIG. 48.

At block 1320, a cross-correlated imaging result is generated. The cross-correlated imaging result may be generated using the first quantitative result, the second quantitative result, the processing protocol for the experiment and, in some implementations, one or more of the first image data, the second image data, or information based thereon (e.g., an attribute of the subject identified by the image data).

Generating the cross-correlated imaging result may include comparing the first quantitative result with the second quantitative result as directed by the processing protocol. For example, the cross-correlation may include presenting the respective image in a format that permits parallel comparison of the different image data.

Figure 51A:
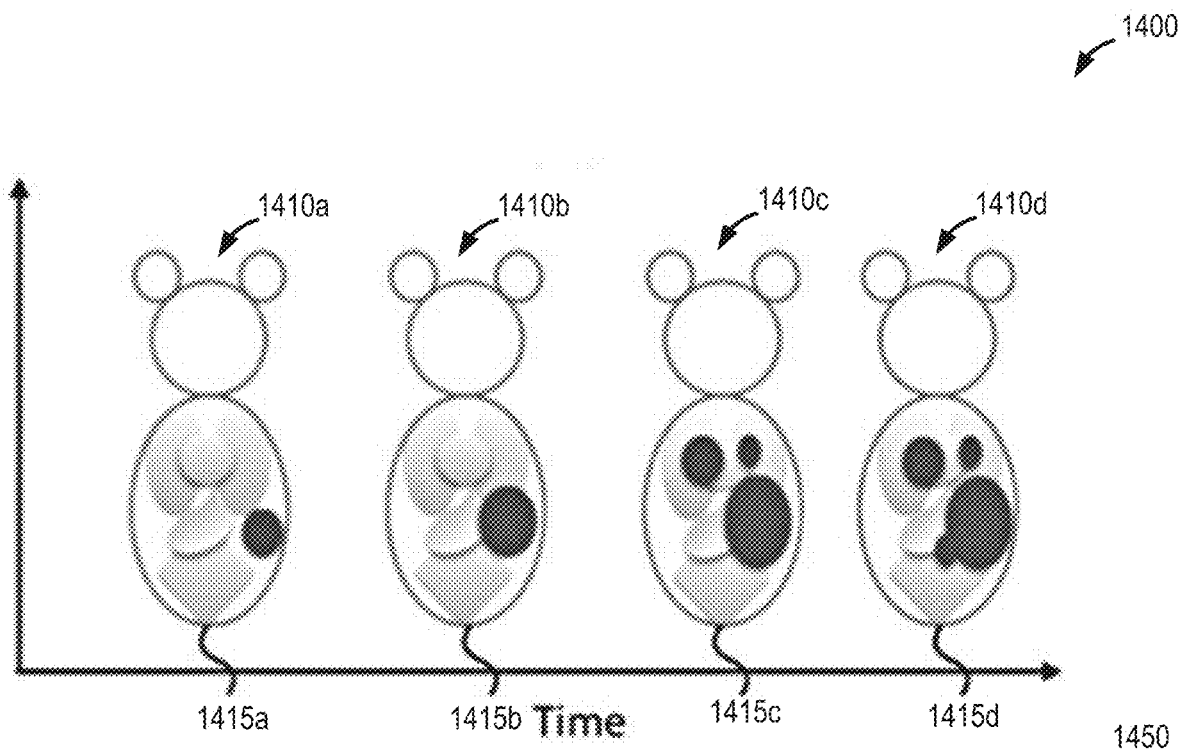
FIG. 51A shows a graphic diagram of an example presentation of cross-correlated imaging result.

FIG. 51A shows a graphic diagram of an example presentation of cross-correlated imaging result. In the cross-correlated imaging result 1400 shown in FIG. 51A, four imaging results (1410a, 1410b, 1410c, and 1410d) captured at respective times (1415a, 1415b, 1415c, and 1415d) are presented visually side-by-side.

Figure 51B:
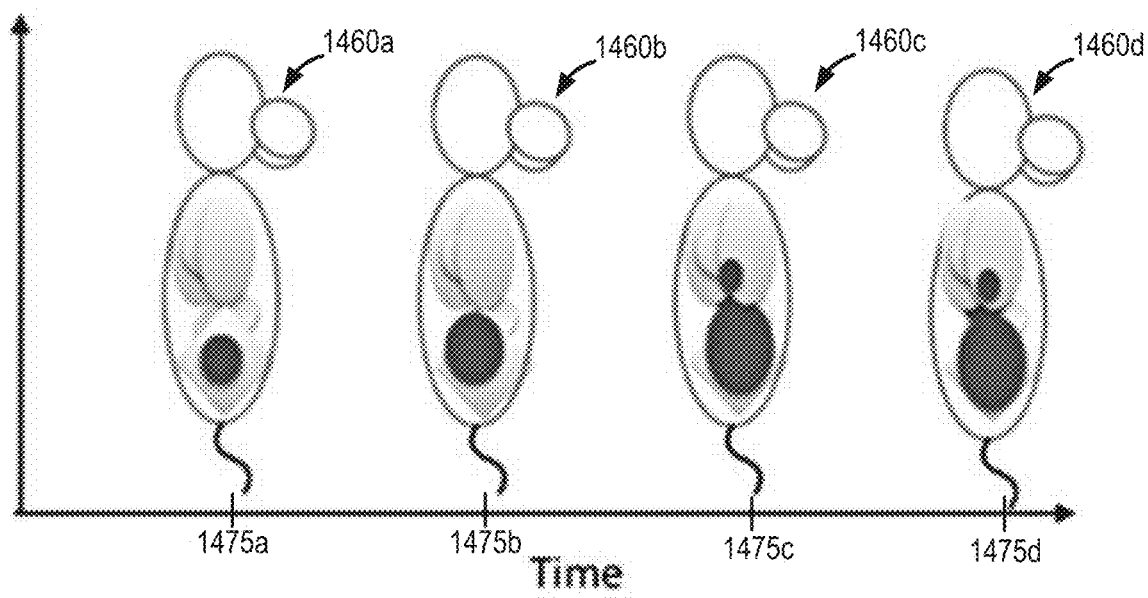
FIG. 51B shows a graphic diagram of another example presentation of a cross-correlated imaging result.

FIG. 51B shows a graphic diagram of another example presentation of a cross-correlated imaging result. In the cross-correlated imaging result 1450 shown in FIG. 51B, four imaging results (1460a, 1460b, 1460c, and 1460d) captured at respective times (1475a, 1475b, 1475c, and 1475d) are presented visually side-by-side. The imaging results 1460a through 1460d may be for the same subject shown in the imaging results 1410a through 1410d of FIG. 51A. However, in FIG. 51B, the results are shown from a sagittal view while the results in FIG. 51A are shown from a coronal view. In some implementations, the original image data used to generate the imaging results may not have included a depiction of one or more of these views. Through image processing using the position information for the image data and the subject atlas, such views can be constructed. For example, views may be combined. One combination may be to merge a ventral and a dorsal view to generate in a single view around the entire animal (e.g., 360 degree view). In such merged views, the light intensities may be corrected such as to account for different Cosines of the exiting angle of the light.

Figure 52:
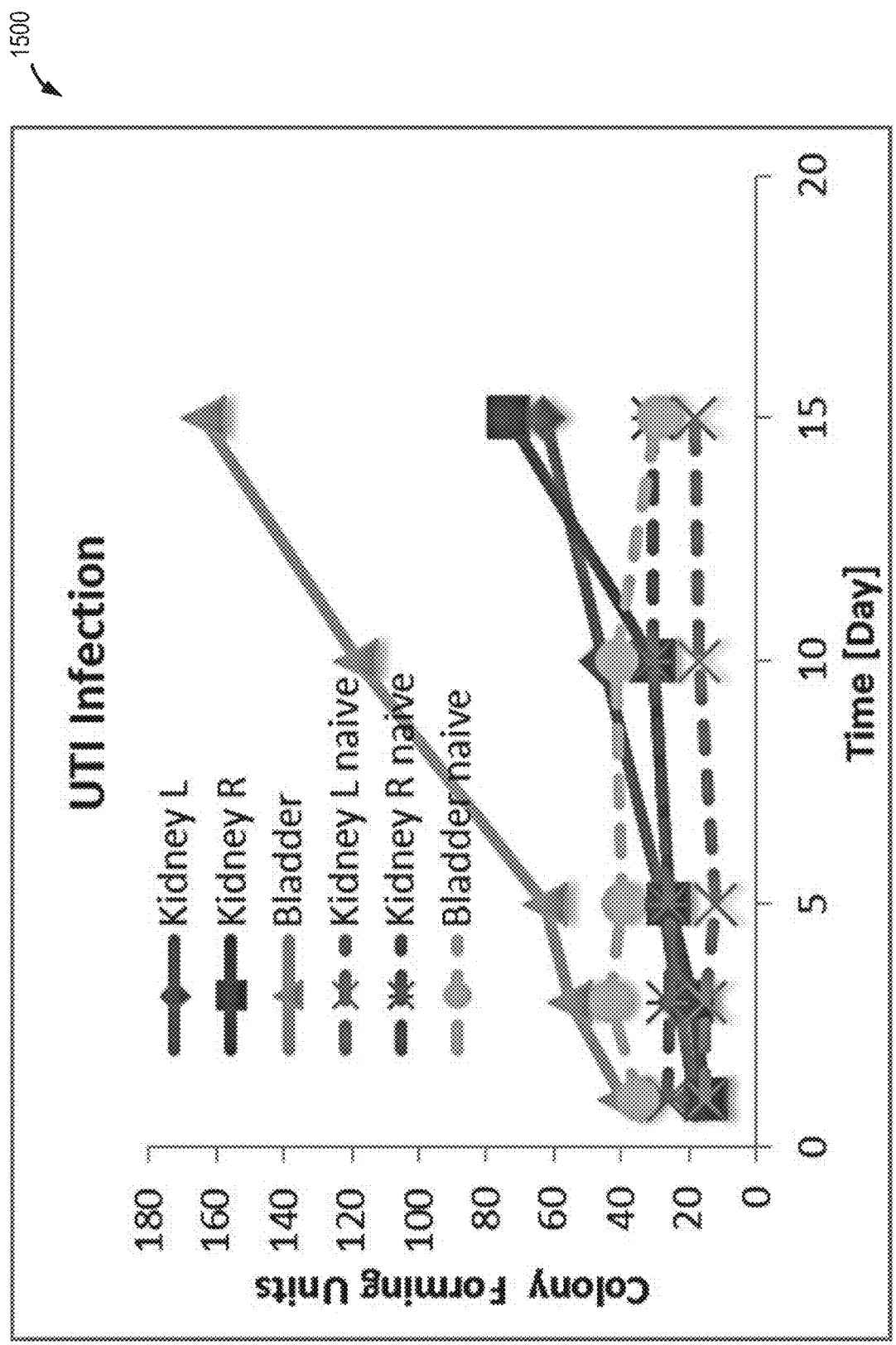
FIG. 52 shows a plot diagram of a further example presentation of a cross-correlated imaging result.

FIG. 52 shows a plot diagram of a further example presentation of a cross-correlated imaging result. As shown in FIG. 52, imaging results from two different subjects are presented on a single cross-correlated imaging result 1500. The imaging results for a first subject include colony forming units over time for three anatomical structures of the first subject, namely left kidney ("Kidney L"), right kidney ("Kidney R") and bladder ("Bladder"). The imaging results for a second subject includes colony forming units over time for three anatomical structures for the second subject, namely left kidney ("Kidney L naive"), right kidney ("Kidney R naive") and bladder ("Bladder naive"). As can be seen in the cross-correlated imaging result 1500, the second subject exhibits a substantially lower number of colony forming units as compared to the first subject over time.

The image processing server 700 may generate other image processing results. Examples of other image processing results that may be generated for the image data using the positioning assembly and position definitions described include 3D reconstructions, maximum intensity representations, sagittal views, coronal views, transaxial slice views, interactive (e.g., rotatable) views, movies, and/or 3D views along an x-axis in time. The image processing server 700 may cause presentation of an interface for visualizing an imaging result. The interface may include control elements that, upon activation, adjust the representation of the imaging results shown. For example one or more control elements may be provided to: enable or disable data transparency and select from a list of anatomical features of interest (e.g., organs) and 3D biolum of those organs will only show up. Because regions of interest may be predefined for all organs, the adjustment to shown or hide regions of interest involves displaying voxels in the region of interest and hiding voxels outside of the region of interest. The interface may provide an imaging result generated from the initial imaging result. For example, as data included in the result is filtered (e.g., by region(s) of interest), a filtered imaging result may be generated that provides a representation that integrates values in the region of interest. In some implementations these values for the region of interest may be plotted as a function of x-axis in time or a user-defined database label.

In addition to providing interface features for a specific imaging result, the interface may also include features for comparing multiple imaging results. For example, a control element may be provided to receive information identifying another dataset to compare with the imaging result. In some implementations, the information may also include a desired analysis to use for comparing the selected dataset with the imaging result. The control element may selectively present analytics that are available based on the imaging result and the selected dataset. For example, the analytics available may be limited by the type of data or quantity of data in the selected dataset.

The interface may provide an analysis aggregate of all the selected datasets. For example, an aggregate may include a cross-correlation of image data collected for subjects undergoing different therapies.

An image processing server may also be configured to direct the acquisition of image data. For example, it may be desirable to provide information to an imaging device to configure the imaging device to capture specific image data, such as for a specific experiment, subject, and/or position. Such features can increase the reliability of the image data received by ensuring the appropriate portions are captured at a specified resolution, rate, format, etc. for processing via protocols defined for the experiment.

Figure 53:
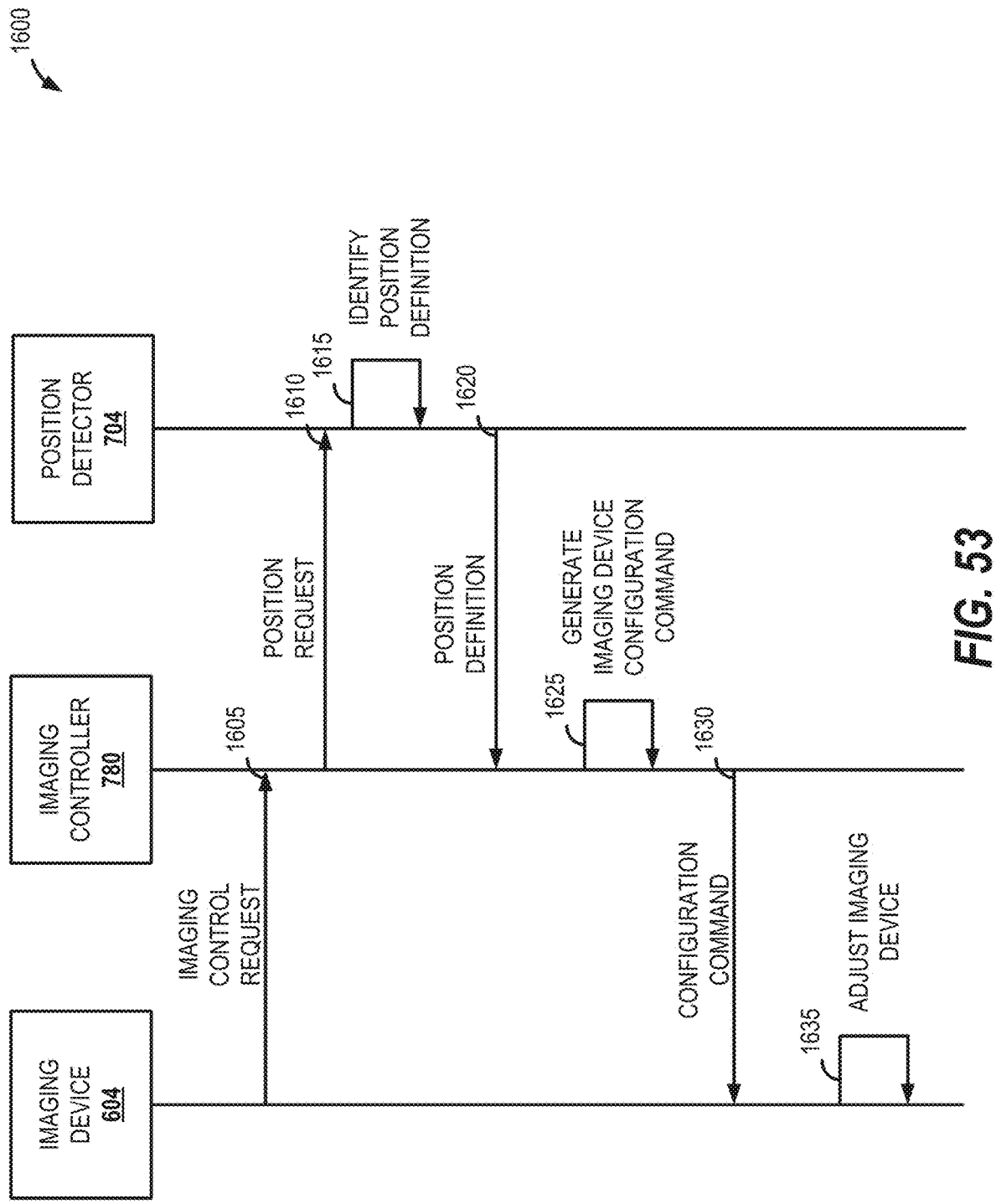
FIG. 53 shows a message flow diagram for an example process of dynamically configuring an imaging device.

FIG. 53 shows a message flow diagram for an example process of dynamically configuring an imaging device. For example, the message flow 1600 shown in FIG. 53 illustrates how an imaging device can be adjusted for image data capturing using an image processing server. The message flow 1600 shown in FIG. 53 provides a simplified view of messages that may be exchanged between the entities shown for dynamically configuring an imaging device. It will be understood that additional entities may mediate one or more of the messages shown in FIG. 53.

The imaging device 604 may determine that a subject is ready for imaging. The readiness may be determined by detecting the insertion of a positioning assembly in an area near the sensor. The readiness may be determined by an input to the imaging device 604 such as via a button or interface. The readiness may cause an imaging control request message 1605 to be transmitted to the image processing server 700. The imaging control request message 1605 may be routed to the imaging controller 780.

The image control request message 1605 may include information identifying one or more of the subject to be imaged, the experiment, the positioning assembly to be used during collection of the image data, the imaging device, and the sensor of the imaging device to be used for collecting the image data. The imaging control request message 1605 may include information identifying the message 1605 as an imaging control request message thereby allowing the image processing server to distinguish between requests for image processing and requests for imaging control. In some implementations, the imaging control request message 1605 may include an image (e.g., taken with a camera) of the subject such as that shown in FIG. 48. Based on the The imaging controller 780 may generate and transmit a position request message 1610 to the position detector 704. The position request message 1610 may include all or a portion of the data included in the image control request message 1605. In some implementations, the imaging controller 780 may cause preliminary processing of the image data to extract a portion of the image data that identifies the positioning assembly used to capture the image data. This may include identifying image data for a machine readable identifier for the positioning assembly.

Via messaging 1615, using at least some of the information included in the position request message 1615, the position detector 704 identifies the position definition corresponding to the request 1615. The identification may include querying the subject atlas data store 614 or other data storage device that includes a data record associating the machine readable identifier with a positioning assembly. In some implementations, an image processing configuration may be provided to the image processing server 700. The image processing configuration may include the associations between the identifier included in the image data and the positioning assembly.

The identified position definition is then transmitted via a position definition message 1620 to the imaging controller 780. In some implementations, the image processing server 700 may be processing multiple control requests. In such implementations, it is desirable to include information to distinguish message flows for respective control requests. The position definition message 1620 may include an identifier to facilitate coordinate of a response with a particular request. The identifier may be specific to the overall control flow or to a portion of the control flow such as the position request.

Via messaging 1625, the imaging controller 780 generates an imaging device configuration command message. The imaging controller 780 may generate the imaging device configuration command message based on the position definition received via the position definition message 1620. The imaging controller 780 may be configured to identify a processing protocol for the anticipated image data for the experiment using one or more of the image data, the detected position, and the position definition. As discussed above, the processing protocol may identify which values to collect. The processing protocol may identify a desired format for the image data (e.g., JPG, GIF, TIFF, XML, comma separated values, etc.). This can ensure that the image data collected by the imaging device 604 can be processed via the image processing server.

Generating the imaging device configuration command may also include identifying a location of interest to be imaged. For example, for the subject in the identified pose and the imaging device that will be collecting the image data, it may be desirable to provide direction to the imaging device as to where image data should be collected. Consider a mouse subject undergoing an antibacterial drug experiment. The experiment may be testing efficacy of a drug to reduce bacterial counts in the mouse's liver. In such experiments, it may be desirable to collect image data from the liver area of the mouse.

Using a subject atlas entry corresponding to the attributes of the mouse within the identified position, a location of the liver area can be identified. This location information can then be used to generate a configuration command for the imaging device such that the area of interest is detected.

This can provide several non-limiting advantages. One non-limiting advantage is assured capturing of image data for the area of interest. Rather than obtaining image data and then confirming whether the image data is suitable for the experiment, the imaging device can be configured dynamically, before capturing the image data, to ensure the desired data is obtained. As another example of a non-limiting advantage, by identifying the specific anatomical region for imaging, the imaging device can hone in on an area of interest rather than wasting resources capturing areas that are not of interest. Furthermore, for some imaging devices, the sensor may cause adverse effects such those caused by exposure to excessive radiation. As another example, by targeting a specific anatomical region, the resolution obtained for the image data may be increased because the sensor data can be concentrated at a specific area of interest rather than spread out over the entire subject. As another example, the capturing of image data for a specific area can provide a consistent frame of reference for cross-correlation studies. In an experimental study where the image data is not captured in a targeted manner, an initial selection is typically performed to identify the area of interest included in the image data. This can be subjective and prone to error. Furthermore, the surrounding area may bias or otherwise affect the analysis of the actual area of interest. By targeting at the time of data collection these sources of experimental error can be reduced.

Another non-limiting advantage of using an organ probability map (OPM) is the automatic registration of the subject's anatomy to the optical signal. Hence, specific regions of the subject can be analyzed according to its known anatomical structures, instead of 'guessing' where the signal is coming from. Furthermore, a so-called 'biodistribution' of the optical signal may be obtained. The biodistribution increases the accuracy for determining the optical light intensity distribution because the intensity is identified and can be corrected according to its anatomical source of origin rather than a static coordinate location of an image. This accounts for minor anatomical variations that can have significant impact on the detected image data.

The imaging controller 780 may also consider previously generated imaging results when generating the configuration command. For example, if a subject identified in the image control request message 1605 is associated with a prior imaging result, additional information about the subject, its anatomy, trajectory through the experiment, etc. may be know. Using one or more of these elements of prior information, the configuration command can be further tailored to the specific subject. For example, while subjects are selected from a known strain of mice, there is some chance that small variations exist between mice. The liver for a given mouse could be located in a different location than another mouse. The configuration command can be adjusted to account for such variations. Specifically, if the location specified is for a standard location of a liver in a mouse, the location information can be adjusted based on the prior identification of the liver in a specific mouse.

The imaging device configuration command may be generated using a library of commands. The library of commands may specify specific message formats and directives that can be specified for a specific imaging device. The imaging controller 780 may use the information included in the imaging control request message 1605 to identify the imaging device 604 and select, such as from the library of commands, one or more commands to configure the imaging device 604.

The imaging controller 780 may then transmit a configuration command message 1630 including the identified information for capturing image data for the specified subject. Via messaging 1635, the imaging device 604 may be adjusted using the configuration command message 1630. Adjusting the imaging device 604 may include adjusting a sensor location, adjusting a sensor emission, adjusting a sensor detector, adjusting a duration of image data capture, adjusting a format for image data captured, or other operational attribute of the imaging device 604 or sensor associated therewith.

Figure 54:
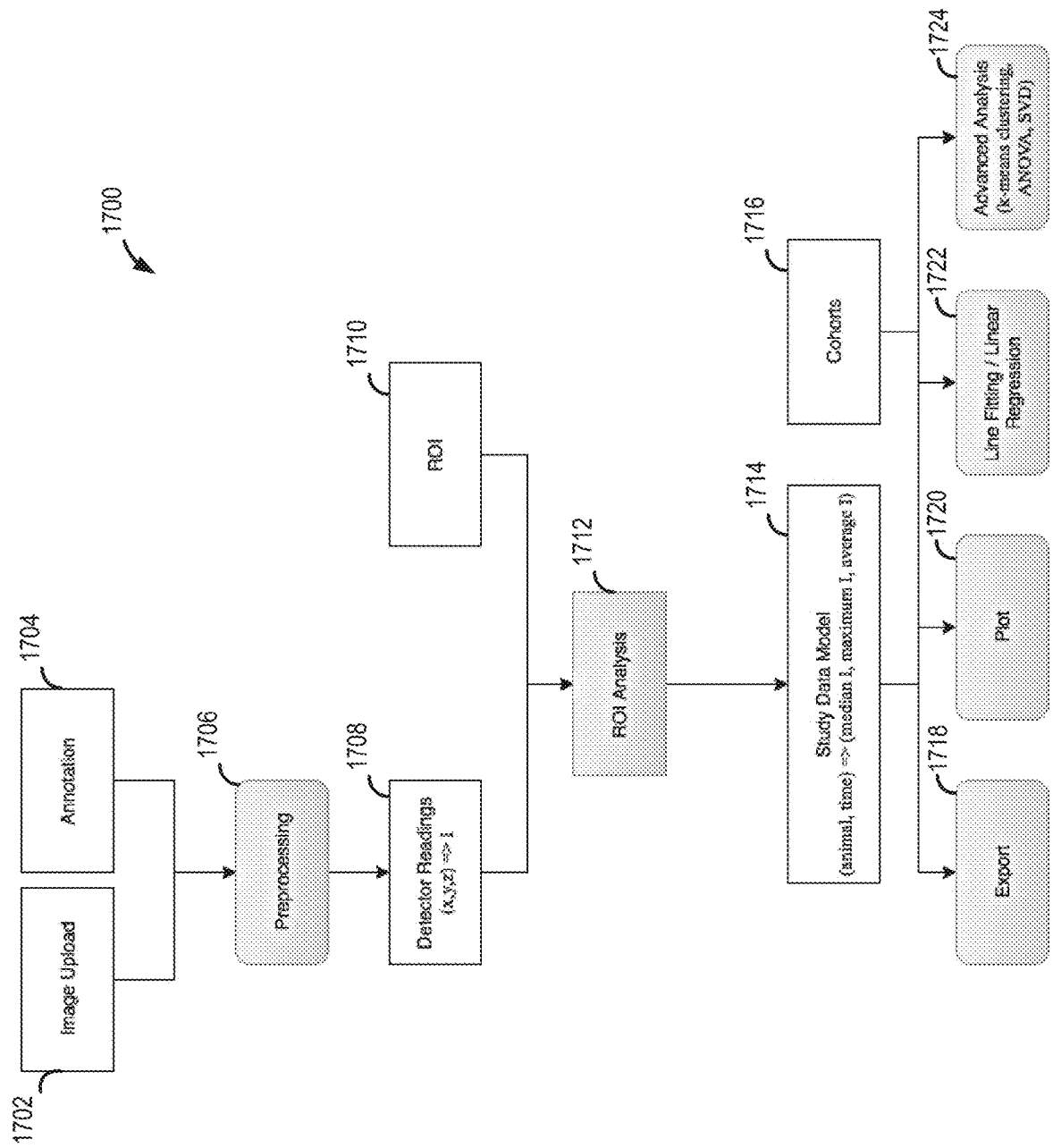
FIG. 54 shows a process flow diagram for another example method of generating a cross-correlated imaging result.

FIG. 54 shows a process flow diagram for another example method of generating a cross-correlated imaging result. The method 1700 may be implemented in whole or in part by one or more of the devices described in this application such as the image processing server 700 shown in FIG. 43 or FIG. 44. In some implementations, the method 1700 may be implemented on device that includes an integrated global memory shared by a plurality of programmable compute units that includes a buffer, wherein the buffer may include a first-in-first-out (FIFO) buffer. The device may further include an integrated circuit (IC) that may include at least one processor or processor circuit (e.g., a central processing unit (CPU)) and/or an image processing unit (IPU), wherein the IPU may include one or more programmable compute units.

The method 1700 shown in FIG. 54 describes a data flow for generating a cross-correlated imaging result, given a set of preclinical images of small animals as input and statistical and quantitative information about the biological target as output. The method 1700 may be implemented as web application accessible by/in a web browser. The method 1700 may utilize a connection between the client and a cloud server for data storage and data analysis.

The method 1700 begins by receiving an image upload 1702 and annotation information 1704 for the image upload 1702. The image upload 1702 may include an image of a subject captured in a specific position. The image upload 1702 may include a set of preclinical images obtained with optical, CT, MRI, PET, SPECT, and/or nuclear imaging systems. The images may be uploaded to a central cloud server. These images included in the image upload 1702 may can have a propriety format or other standard formats like TIFF, JPEG, GIF, DICOM, etc.

Uploaded images can be displayed via a user interface such as web application accessible via a web browser at a client site. The user interface may include control elements to receive the annotation information 1704 for one or more of the images included in the image upload 1702. For example, a client may select or enter text information indicating the subject ID, the sex, the weight, and the study cohort of the subject shown in an image.

After receiving the annotation information 1704, at block 1706, the images may be preprocessed to generate a data set for further data analysis. The generated data set may include a unique standard or format and can be used interchangeably across different images, cohorts, subjects, or studies. For example, a set of images pixels may be cropped from the raw images and scaled to a uniform size with uniform data set size. The cropping may be performed based on one or more characteristics of the subject such as the weight or size of the subject. The preprocessing at block 1706 may include storing the generated data set in the cloud storage in association with the image upload 1702.

At block 1708, a virtual detector point, with predefined spatial coordinates (x,y,z), may be assigned to each data point (I) of the preprocessed images. When assigning the virtual detector points, it may be desirable to ensure that all processed images in a data set have the same or similar number of detector points and with same or similar relative spatial locations for each virtual detector point. A virtual detector point may include specific information identifying the imaging modality used to capture the image, such as the light intensity, x-ray absorption parameter (Hounsfield unit), or percent injected dose or radionuclide activity. Where the virtual detector points share a mutual coordinate system across different animals/subjects, cohorts, imaging modalities, and study points, the preprocessed images are ready for cross-comparison. Subsequently, the detector data points may be displayed as images in the user interface (e.g., the web browser) for each subject and time point.

At block 1710, the user interface may receive selection of a region-of-interest (ROI). The selection may include selecting a set of the virtual detector points. The ROI may be determined automatically by receiving a selection (e.g., from a menu of options include on the user interface) specifying an organ or issue region, or by manually selection a ROI from the spatial distribution of detector data points. The spatial coordinates of an organ may be provided by an organ probability map (OPM), which shares the same spatial coordinates system as the virtual detector data points. The selected ROIs may be transmitted to a cloud server for data analysis across different subjects and/or time point(s).

At block 1712, the ROI analysis may be performed automatically on the cloud server. The analysis may be performed for each subject. The analysis may include generating one or more of the mean, median, maximum, or total value inside the ROI. These data may provide a basic layer for further data analysis performed at different levels, including at the single animal level, the cohort level, the study level, or between different studies. The result of the ROI analysis may include a study data model 1714.

The data analysis, using the ROI information as input, can include different statistical methods or other methods for comparing or quantifying data sets. The data analysis can be applied to a data set of a single animal by comparing different virtual detector points at different spatial locations or time points. It can also be applied to a set of animals within a single cohort, or to different cohorts 1716 within a single study. Furthermore, different studies can be compared to each other.

The statistical methods can include linear fitting or regression analysis of data points 1722 included in the study data model 1714 and/or cohorts 1716, or more advanced techniques 1724 such as Student's t-test, k-means clustering, analysis of variance (ANOVA), or singular value decomposition (SVD).

At block 1718, the final results may be exported to a local storage medium. At block 1720, the final results may additionally or alternatively be plotted on a user interface for presentation such as via the web browser.

The described aspects of the cross-correlation imaging system can be flexibly implemented in a variety of embodiments. In one implementation, the system may implement at least some of the described features as a platform-based technology. The system may include integrated hardware and software add-on and/or retrofit for imaging devices (e.g., BLI systems) that is connected to a cloud-based image processing system. The imaging device hardware plugin can enable quantitative 3D imaging of bioluminescence cells and bacteria inside a living animal. Included in such implementations may be (i) a body-shape conforming animal mold, (ii) a digital mouse atlas providing a dependable anatomical reference and the non-uniform optical tissue parameter distributions, and (iii) an in vitro optical calibrator. Such implementations may be configured to map the spatial bacterial density ($CFU/mm^3$) distribution in a living small animal and co-locate it to an anatomical reference provided by the digital mouse atlas.

The cloud-based image data processing system may be connected to the plugin-unit and configured to collect image data, determine the 3D spatial bioluminescent bacteria distribution, perform the data calibration using the in vitro optical calibrator, and automatically generate imaging results across animals and/or modalities without requiring any operator interference. Some implementations may also generate a final study report that provides imaging results such as a cross-correlated longitudinal study report. The image data processing system may be configured to provide automated data processing across different animals and time points based on the animals' positions. The positioning assembly (e.g., the animal mold) may be included to provide a constant spatial frame for all animals. Therefore, the need for manually drawing region-of-interests for each animal and the labor-extensive book-keeping of data, while being prone to human error of visual inspection, becomes obsolete. The features may be included in an unattended workflow such that automated image data processing and reporting of animal studies becomes feasible.

The imaging processing server may be located on a centralized server ("cloud") and connected with a client computer for data acquisition ("imaging computer" that hosts the add-on/retrofit plugin unit). In some implementations, the imaging processing server may be connected directly with the imaging device. In some implementations, the image data processing server may be in data communication with a client computer of the investigator. The image data processing server may be a specially architected computing system including specific hardware to facilitate efficient application of different mathematical tools for large-scale data processing and storage across different animal and time points ("big data").

In one implementation including some of the features described, a bacterial density distribution inside a subject can be generated as the imaging result. To generate the bacterial density, the system may include a single body-shape conforming animal mold for a 23 g mouse, an in vitro optical calibrator, an OPM for a male C3H mouse (23 g), and a two-mirror gantry for multi-view imaging. These features may be used for experiments where quantitative and biologically relevant information (e.g., $CFU/mm^3$) about bacterial organ burden in place of physical quantities of a bioluminescent source (photons $s^{-1}$ $cm^{-3}$) can be obtained in part using an imaging device and an OPM.

The animals may be immobilized inside the mold and placed on the mirror gantry. A series of spectral images (e.g., four, three, six, or more) were taken from the dorsal/ventral side of each animal. The spectral images may be taken at different wavelengths (e.g., 550-720 nm, 50 nm bandwidth, 3 min). The availability of wavelengths may be determined based on the number of optical filters included in the detector and/or the spectral bandwidth of the filters included in the detector. Implementations may include 2 to 100 optical filters. A filter may have a spectral bandwidth of 1 nm-100 nm spectral. The spatial photon emission density distribution (photons $s^{-1}$ $cm^{-3}$) may then be reconstructed with a simplified spherical harmonics ($SP_N$) based on, for example, BLT reconstruction. A calibration factor may then be generated using the optical calibrator. Here, the photon emission density distribution may be reconstructed by the BLT algorithm while the actual CFU count inside the calibrator was known. Therefore, the unknown bacterial density distribution ($CFU/mm^3$) of one or more subjects could be determined by multiplying its reconstructed photon emission density by the calibration factor determined from the optical calibrator. The spatial $CFU/mm^3$ distribution may then be co-registered to the OPM.

In an experimental system configured as described, a Pearson correlation coefficient of $R^2=0.98$ of the reconstructed with respect to the given total CFU inside the capsule was obtained. In comparison, planar BLI was observed as achieving an $R^2=0.48$ when using the maximum light intensity of the region-of-interest. These preliminary data provide a proof of concept of calculating the bacterial density distribution inside a living animal using a positioning assembly such as an animal mold, a BLT algorithm, and an optical calibrator.

As part of the experimental system, a digital OPM mouse atlas was developed, which provides (1) an anatomical reference for the spatial in vivo bacterial density distribution and (2) the non-uniform optical tissue parameter distribution of $\mu_a$ and $\mu_s'$ for the BLT algorithm.

In the experimental system, the OPM was built from contrast-enhanced CT scans using a vascular imaging agent such as AuroVis™ 1.9 nm commercially offered by Nanoprobes, Inc. N=20 CH3/HeN mice with average weight of 23±1 gram (~10 wk) were imaged inside the mold with a micro-CT (such as a preclinical imaging system offered commercially by Mediso USA), and several organs (e.g., skeleton, lung, kidneys, liver, heart, bladder, brain) were manually segmented using a medical imaging workstation configured for segmentation such as with Mimics©, commercially offered by Materialise NV. The segmented images were defined on a Cartesian grid with 0.5 mm resolution and each organ is labeled with a numerical identifier. The OPM was generated by determining the probability $p_i^j$ ($0 \le p \le 1$) at each image voxel i for finding a given organ j. The highest (lowest) probability $p_i^j$ of (not) finding a given organ j at voxel i is $p_i^j=(p_i^j=0)$. The maximum probability, max $(p_i^j)$, of all j at given mutual voxel determines a non-overlapping boundary between different organs.

To address the different optical properties of organs, the OPM may be translated into a non-uniform map of the tissue absorption ($\mu_a$) and reduced scattering ($\mu_s'$) coefficients. The spectrally-dependent maps of $\mu_a$ and $\mu_s'$ can be built from the OPM for four partially overlapping wavelength intervals of 50 nm between 550-720 nm (spectral range with largest variation of tissue light absorption). In embodiments were a different number of spectral images are used, the number of overlapping intervals would correspond to the number of spectral images.

Each voxel element i of these maps constituted the expectation value, $\bar{\mu}_s$, given the $p^j$ and the $\mu_a^j$ and $\mu_s^{ij}$ of each organ: $\bar{\mu}_s = \Sigma_{i=1}^{j} p_i^j \mu_i^j$. The $\mu_a^j$ and $\mu_s^{ij}$ coefficients were defined by the blood oxygenation level and by Mie-Scattering theory. The 'intermittent' or 'background' tissue that is not defined by a given organ were a mixture of muscle and fat.

The OPM atlas ($R_A$) generated by the experimental system was validated with additional segmented CT scans ($R_E$) of N=10 C3H/HeN mice (23 g). The accuracy of the atlas $R_A$ was validated by voxel-wise comparing the organ probabilities with largest $p^j$ to the expert data set $R_E$. DICE and volume recovery coefficients (VRC) were calculated between 0.9 and 1.0. The DICE coefficient is the registration accuracy for each organ and is given by:

$$DICE = 2 \frac{R_A \cap R_E}{R_A + R_E}. \quad (24)$$

The VRC is the ratio of the recovered organ volume of data sets $R_A$ and $R_E$. VRC and DICE coefficients≈1 indicate an exact match (0% error). Results were also compared to the outcome of similar mouse atlas studies (21, 24, 25, 33). The root-mean-square-error (RMSE in [%]) is used for validating the milestone. The experimental system including the features described yielded a DICE>0.6 (RMSE<40%) and 0.7<VRC<1.3 (|RMSE|<30%) for at least five out of seven organs.

One benefit of the describe image analysis features is the ability to generate imaging results in real time. Real time may generally refer to generating an imaging result in proximate time to when the image data is received for analysis. In some implementations, real time result may refer to a result generated from 1 second up to 1 minute after receipt of the image data.

One experimental system including the features described was configured to generate an imaging result identifying the ii, vivo CFU/mm³ distribution inside a urinary tract infection model using bioluminescent pathogenic E. coli. The spatial CFU distribution was registered to an anatomical reference.

An optical in vitro calibrator (2×3×10 cm³) was developed that consists of four compartments of optical tissue phantom material (e.g., polyurethane commercially available from INO, Quebec) with different $\mu_a$ and $\mu_s'$ at 600 nm ($\mu_a$=0.14-1.24 cm⁻¹; $\mu_s'$-10.5-12.5 cm⁻¹, Δμ=±10%). Hence, each compartment mimics the average optical properties of animal tissue at a single spectral band (50 nm) between 550 nm-720 nm of the bioluminescence spectrum. Each compartment has a cavity (80 μL), which can hold luminescent bacteria with known CFU/mm³. The light intensity was measured at the calibrator surface by taking a single image at 600 nm. Given the different optical properties of each compartment at 600 nm, a data set of attenuated light images could automatically be assembled that is equivalent to the intensities of four different spectral bands btw. 550 and 720 nm. The BLT algorithm reconstructed the photon emission density and, given the known CFU/mm³ inside the calibrator, the calibration factor for the photon emission density could be calculated. This calibration factor was used later for the in vivo experiments.

The feasibility of generating an in vivo CFU imaging result using the experimental system was demonstrated by using an established model of a UTI by inoculating both wild-type C3H/HeN mice (N=10) which get cystitis (bladder infection), and C3H/HeJ mice (N=10) which get both cystitis and pyelonephritis (kidney infection) with small volumes of the lux-bacteria (20 μl of 5×10⁸ CFU ml⁻¹) by transurethral catheterization. The in vivo bacterial burden in the bladders and the kidneys was determined 24 hours after inoculation using the calibrator. The animals underwent BLI and four spectral images were measured. The BLT algorithm reconstructed the photon emission density, which was transformed into the CFU count by using the calibration factor. The spatial CFU distribution was co-registered to the OPM mouse atlas and the organ site of bacterial infection was instantaneously determined. Post imaging, the animals were sacrificed and the kidney and bladder volumes were determined and plated for ex vivo CFU count. The total calculated CFU count was compared to the total CFU count of harvested organs.

The image data processing was performed for all BLT reconstructions calculated by the $SP_7$ model using g=0.7, g=0.9, and g=0.98, and the diffusion model for the same $\mu_s'$. The outcome of study series was compared and the best method was determined. The measure of performance used was the root-mean-square error (RMSE) and the Pearson correlation coefficient ($R^2$). First, the RMSE and $R^2$ of the calculated versus the actual total CFU of each organ was determined and compared. Next, the RMSE and $R^2$ was compared by either using (i) the 'correct' non-uniform optical parameter distribution based on the OPM or (ii) the uniform optical tissue properties (same parameters as from optical calibrator). Last, the $R^2$ of the reconstructed in vivo CFU count were compared with the $R^2$ obtained from region-of-interest of 2D bioluminescence images ('standard of practice').

In one embodiment, the experimental system provided results with a RMSE<30% and a $R^2$>0.94 in at least 7 out of 10 animals thus indicating that real time generation of the imaging results is achieved.

The cross-correlation image data processing is dependent, in part, on the positioning of the subject. The positioning provides a way to process the image data using the position definition from a subject atlas. A positioning assembly, such as an animal mold, can provide a consistent surface for detector locations and allows for stable source-detector geometries on which the kernel matrix is pre-determined and hard-coded rather than built for each data set, affording an enormous computational cost savings. Given the consistent volumetric parameter space that the positioning assembly provides, similarity measurements between reconstructions of different mice and different time points can be directly computed due to the shared 3D Cartesian grid of the positioning assembly data sets and organ probability map. The spatial domain being standardized by the positioning assembly, affine and morphological transformation calculations are not required, as would be necessary in positioning assembly-free mouse imaging where volumetric grids differ.

Similarity metrics of 3D reconstruction in the described imaging systems can then be used to automatically classify animal cohort sets and other sets such as disease/therapy progression state using objective and unbiased cluster analysis. Localizing the site of bacterial infection in mice of different weight/size/age requires a body-weight-dependent animal mold. Furthermore, a size-specific OPM for male and female mice is necessary for body-weight-dependent anatomical co-registration. A body-weight-dependent animal mold also enables the automatic cross-correlation of image data across mice of different weight, sex, and strain and at different time points. The construction of an optical tissue property map for the BLT analysis may use information about the animal's anatomy for different animal ages and sex. X-ray CT and MRI have been partially successful in providing anatomical information, but can be expensive, and require additional imaging time, animal handling, and trained personnel. Low-cost non-tomographic methods, e.g., photographic imaging, 3D surface scanning, and planar X-ray imaging have been considered for body profiling, but they alone do not provide accurate anatomical information.

In experiments using mice, positioning assemblies may be provided for different body weights of the C3H and BL6 mouse strain. The BL6 mouse strain has a slightly different body shape. It may be desirable to have the positioning assembly be optically transparent to allow imaging devices to detect the subject contained therein. The positioning assembly may hold the subject (e.g., animal) in a fixed position and define the subject's surface geometry. The positioning assembly may consist of two shell-like parts made of polycarbonate that can be tightly secured with a latch, while slightly compressing the subject and without changing the animal's shape. The inner surface of the positioning assembly may form the shape of a CH3/HeN mouse. The positioning assembly may fit into a mirror gantry inside an imaging device such as those commercially available from the IVIS™ (e.g., IVIS SPECTRUM, IVIS 100, IVIS 200, IVIS LUMINA) commercially available from PerkinElmer and/or the PhotonImager™ commercially available from Biospace Lab.

A set of positioning assemblies may be provided to cover the range of subjects for an experiment. For example, in the case of an experiment using mice, twelve positioning assemblies may be provided for covering a weight range of animals between 16.5-34.5 g with each positioning assembly accepting a weight tolerance of ±0.75 g. Assuming a maximum spatial tolerance of $\sigma=0.375$ mm between the animal's surface and the positioning assembly is accepted (which is significantly less than the maximum achievable image resolution of 1-2 mm in BLT), a maximum tolerance of in mouse volume may be defined such as 1.5 cm$^3$. In some implementations, increasing the spatial dimensions along all three major symmetry axis of an animal by $2\sigma=0.75$ mm, may yield an increase of volume of ≈1.5 cm$^3$. The volume tolerance defines the weight change of 1.5 g between two positioning assemblies, assuming a tissue density of approximately 1 g/cm$^3$ In some implementations, an acceptable animal weight for a single BCAM may ranges between +/−0.75 g.

Each positioning assembly may be scaled according to an x,y,z-dependent scaling factor using one positioning assembly, such as the positioning assembly for a 23 g subject, as master copy. The scaling factors may be determined using optical imaging of the surface geometry of different animal sizes and validated with CT scans.

Positioning assemblies for different strains and body weights can be rapidly be manufactured. For example, optically transparent polycarbonate shells can be produced with an injection molding system such as QuickParts which is commerically available from 3D Systems, Inc. The injection molds for generating the positioning assemblies may be formed of aluminum and can be machined using a CAD file of the scaled mold. In some implementations, a CAD file for a master copy may be scaled using the parameters described above to automatically generate additional CAD files for different positioning assemblies within the set of positioning assemblies for a species.

OPMs for each sex (male/female) of different mouse breeds (C3H and C57BL6) may be similarly developed. For example, n=24 contrast-enhanced CT scans may be obtained for a female C3H mouse with body weight of 23 g. In addition, n=24 CT scans of a male BL6 mouse (23 g) and n=24 scans of a female BL6 mouse (23 g) may be obtained. The OPM may also be expanded to include identification of additional anatomical features such as gallbladder, spleen, testicles, GI tract.

Referring now to the image processing server, commercial 3D bioluminescence reconstructions are prone to over 50% variability in reconstruction intensity and distribution width, due to user-subjectivity in image data processing. Some current commercially available bioluminescence tomography implementations require tedious and subjective user-input for multiple steps of the tomographic process, and gives rise to inconsistent reconstructions with the same data set. Longitudinal study evaluation with error-prone reconstructions inflates inaccuracies. Regions- or volumes-of-interest analysis is vital for quantifying bacterial burden, proliferation, and therapeutic efficacy. Furthermore, regions- or volumes-of-interest may not be rigorous if reconstruction noise properties are not known. Automating the reconstruction process using explicit noise analysis from the data-end to reconstruction-end provides further non-limiting advantages of eliminating operator interpretation, enhancing data accuracy, increasing reproducibility, and reducing image data processing variability.

The image data processing process is possible, in part, through the use of standardizing positioning assemblies, which also serves to enclose a common parameterized space in which mathematical operations can be performed to automatically quantitatively characterize and systematically compare reconstruction data. The image processing server provides an operator-independent analytical system for processing optical image data. This cloud-based discovery process can lower costs and shorten study analysis time.

Operator-involved image data processing introduces subjective variability in 3D reconstructions and image interpretation. Quantitative assessment of image quality is generally missing in commercial imaging modalities. The statistical estimation underpinning of bioluminescent reconstruction may not effectively be conveyed to investigators and reconstruction interpretation thus can have a strong subjective element. Non-uniform spatial resolution and reconstruction artifacts may be inherent in 3D optical tomography and can be rooted in the mathematical expressions of the physical process. However, tomographic resolution analysis can expose resolution artifacts. Resolution analysis to uncover artifacts must be considered. As such, quantitative 3D reconstruction resolution metrics can be used to make informed and respectable evaluations of disease temporal and spatial distribution, yet have not been sufficiently addressed for bioluminescence tomography.

Some image processing systems include features to identify artifact regions and determine resolution by determining uncertainty in the reconstruction parameters. Automation of 3D reconstruction resolution metrics enhances interpretability of the reconstructions, which can be desirable for robustness and a transparent discovery process.

Moreover, it is often a subjective exercise for an investigator to determine the extent of the region- or volume-of-interest boundaries by visually inspecting a 3D bioluminescence reconstruction. Classification schemes separating feature detection (e.g., quantified bacterial distribution) from artifacts can be automated with use of reconstruction performance metrics. Computer vision techniques may be included in the image processing system to remove operator bias in feature extraction in the presence of image noise and artifacts. Feature extraction algorithms using reconstruction performance metrics can segment regions-/volumes-of-interest containing high quality data. Quantitative data quality metrics provide more actionable and standardized data. Bacterial distribution reconstructions that have crossed the performance metrics pipeline can be digitally projected onto an organ probability map for automatic region of interest segmentation. This can replace time-consuming organ harvesting and plating procedures and provide consistent data on the temporal evolution of disease or therapy in the same mouse.

Regions-of-interest manually drawn to compare 3D bioluminescent reconstructions between mice and time points can be prone to inconsistent and subjective selection by the operator. Using the described features, similarity measurements between reconstructions of different subjects and different time points can be directly computed due to the shared 3D Cartesian grid of the positioning assembly and the organ probability map. Similarity metrics of 3D reconstruction image results can then be used to automatically classify blinded animal cohort sets and other sets such as disease/therapy progression state using objective and unbiased cluster analysis.

Characterization of the disease into anatomical categories can be followed temporally in a quantified and automatic methodology. Automation for temporal quantification is achievable, in part, by exploiting the normalization which the positioning assembly and the organ probability map that produces a consistent surface and reference anatomy, as well as computer aided detection. This method offers independence from user subjectivity, enhanced data accuracy, and increases analysis speed by automating the full data analysis process.

Parallelized processing of the analysis, from reconstruction to analytics, can further provide time and cost savings for both computationally expensive algorithms and analysis of big data ensembles. Transparent, automated study reports generated by the cloud-based software can unburden researchers from screen-time and accelerate scientific discovery.

The image processing server may provide an imaging result using reconstruction data which passes through the following analysis pipeline: reconstruction uncertainty mapping, distinguish features from artifacts, determine regions/volumes of interest, digitally plate and measure organs, and classify animals into cohort categories in a blind fashion.

For uncertainty mapping, the performance of the reconstruction algorithm can be evaluated with quantitative performance metrics that will be computed for each reconstruction data set. Tomographic sensitivity 3D maps may be dependent on imaging geometry, instrument sensitivity, and physical models. Reconstruction resolution can be examined and optimized by identifying source-detector geometries for each positioning assembly size. Computer aided detection can automate feature selection (e.g., anatomical feature of interest) in the reconstructions and remove user subjective bias. The organ probability map can be used to associate the reconstruction features to anatomical sources in a statistically accurate fashion. The association may be possible even when structural imaging modality data is absent. For example, mapping of bioluminescent features to anatomical organs can be used to categorize disease extent.

The quantitative performance metrics can be generated with the simplified spherical harmonic model on a 3D Cartesian grid within a digitized animal mold surface. Fisher information $$\left(I(x) = -E\left[\frac{\partial^2}{\partial x^2}\ln p(y|x)\right]\right)$$

can be calculated to elucidate spatial resolution strengths, where E[•] is the estimator, x is the estimated parameter, y is the data, and p(y|x) is the probability distribution of y given x. Propagating data noise through Cramer-Rao Lower Bound (CRLB>I(x)$^{-1}$ for biased estimators) may be used to identify voxel lower bounds on intensity covariance estimates, based on both model and data uncertainties. Tests of 3D resolution can be conducted with simulated checkerboard source tests to determine resolution matrices and local impulse response functions and contrast-detail maps.

To distinguish features from artifacts, spatially distributed reconstruction image noise determined from parameter uncertainty estimates as described above can be used to explicitly identify feature voxels and enhance signal from noise in the reconstructed images using an objective mathematical observer such as a channelized Hotelling observer (CHO), which is based on reconstruction covariance. The CHO metric may represent an image of signal-to-noise, identifying high bioluminescent signal areas for automatic ROI generation. A channel impulse response filter, such as FWHM=[0.5,1.0,2.0] mm, may be provided for optimum closed form area under the receiver operating curve (AUC).

As discussed above, the features described may provide a virtual representation of the anatomical feature of interest, thereby avoiding the need to perform physical organ harvesting. This may be referred to as digital harvesting and plating. To provide digital harvesting and plating, an organ probability map identified for each positioning assembly associated with image data can provide quantitative anatomical reference to the localized bioluminescent sources. The organ probability map may identify in 3D space the probabilistic location of organs, $\pi_i(\vec{r})=[0,1]$, where i is the organ index at location $\vec{r}$ in 3D voxel space. Bioluminescent intensity estimates $x(\vec{r})\pm\sigma_x(\vec{r})$ can be combined with the OPM for each positioning assembly, so that at location $\vec{r}$, the intensity estimate may be generated using $x_i(\vec{r}) \pm \sqrt{(\sigma(\vec{r}))^2 + (x(\vec{r})\pi_i(\vec{r}))^2}$, associated with organ i if and only if $\pi_i(\vec{r}) > 0$.

Having generated an imaging result, the system may further provide blinded cohort clustering. For systematic and unbiased data inquiry, automatic data set clustering to separate and identify cohorts within large numbers of blinded data sets may be provided. The clustering may include using similarity analysis with Figures of Merit (FOM) such as cross-correlation and mutual information between positioning assembly voxel populations. For example, two voxel box filter sizes=[3,5] may be tested for separation skill of cross-correlation and voxel bin sizes=[1,2] will be tested for mutual Information. The positioning assembly surface invariance can offer robust quantitative comparisons between time points and animal weights on the same animal, and across different animals in the cohorts. Spectral decomposition methods in the spatial and temporal domain, as well as classification algorithms, such as self-organizing maps or k-means clustering using the above FOMs as distance metrics, can be used for characterizing anatomical infection patterns with pathological condition.

The image processing service may be further configured to provide kinematic monitoring image results. For example, time series analysis of cluster evolution can be explicitly plotted, or derived from dimensional decomposition (factor analysis, principle component analysis) of the spatio-temporal data to indicate kinematics of infection migration and therapeutic intervention disease reduction/prevention. 2D and 4D plots can be generated for temporal monitoring. The time evolution of the 3D estimated distribution of disease will be displayed in 4D (the four dimensions being x, y, z spatial locations and time), and as well the time evolution of disease identified to specific organs.

The features described may be implemented in or as part of an operator-independent optical imaging platform system to monitor and quantify both planar (2D) and multispectral bioluminescence tomography (BLT/3D) co-registered to a novel digital mouse atlas. The features provide a non-limiting advantage of permitting the automatic quantification and co-registration of a luminescent signal to an organ. This embodiment may include three parts: a body-conforming animal mold (BCAM); an organ probability map (OPM); and an in vitro optical calibrator (IVOC) device. Together the system permits the automated mapping and quantification of light signal to the OPM.

The BCAM allows the subject (e.g., a mouse) to be placed in a reproducible geometrically constrained position. This stereotactic frame allows repeatable animal positioning. This subject alignment system permits high-resolution 2D data analysis and quantitative BLT which may be co-registered to a novel anatomical atlas. Overall, the BCAM places the subject in a consistent position, regardless of its size, to monitor the same spatial location (e.g., 1 mm×1 mm voxel) overtime. Digitally embedded in the BCAM, is the organ probability map (OPM), representing a digital anatomical atlas. The OPM may represent the spatial probability of an organ in a particular voxel within the BCAM. The OPM permits "digital dissection" and OPM data can be used for longitudinal assessment of diseases. Furthermore, the OPM permits alignment of the greater than ten thousand voxels in the BCAM to be monitored in the studies time course. The IVOC adds another layer to this system by allowing the user an opportunity for to quantify the optical signal to gene expression, cell number, volume or infectious disease burden.

The 2D and 3D systems plugin to existing optical imaging systems. The BCAM may be specially engineered to work with a multi-animal high-throughput holder with integrated anesthesia (2D-holder) and also a mirror gantry for multi-orientation images (3D-holder). The 3D-holder permits simultaneous imaging of the dorsal, ventral, and side views of the subject in the BCAM which may be used for the BLT reconstruction algorithm. The spectral images can be provided to a BLT reconstruction algorithm that includes an expectation maximization (EM) method and the simplified spherical harmonics (SP3) equations for modeling in vivo light propagation. Post reconstruction, the system may calculate a total photon emission density of a volume of interest (VOI). Using this result, the system may identify a cell specific luciferase expression co-registering it to a novel digital mouse atlas.

This plug-in device for small animal optical imaging systems allows both high-throughput planar image analysis and quantitative 3D data output with assignment to specific organs automatically. This platform is a paradigm shifting technology in that it changes the way bioluminescent optical imaging experiments are analyzed at least because: (i) image acquisition is operator independent, (ii) reconstruction is automated, (iii) quantification is automated, (iv) data is normalized and (v) reproducible because of a standardized platform. The platform can automatically analyze optical images to provide unbiased and objective interpretation of the data.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as an image processing device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. An image processing device can be or include a microprocessor, but in the alternative, the image processing device can be or include a controller, microcontroller, or state machine, combinations of the same, or the like configured to receive, process, and display image data. An image processing device can include electrical circuitry configured to process computer-executable instructions. Although described herein primarily with respect to digital technology, an image processing device may also include primarily analog components. For example, some or all of the image cross-correlation algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a composite image processing device, or in a combination of the two. A software module can reside in random access memory (RAM) memory, flash memory, read only memory (ROM), erasable programmable read-only memory (EPROM), electrically erasable programmable read-only memory (EEPROM), registers, hard disk, a removable disk, a compact disc read-only memory (CD-ROM), or any other form of a non-transitory computer-readable storage medium. An exemplary storage medium can be coupled to the image processing device such that the image processing device can read information from, and write information to, the storage medium. In the alternative, the storage medium can be integral to the image processing device. The image processing device and the storage medium can reside in an application specific integrated circuit (ASIC). The ASIC can reside in an access device or other image processing device. In the alternative, the image processing device vice and the storage medium can reside as discrete components in an access device or other image processing device. In some implementations, the method may be a computer-implemented method performed under the control of a computing device, such as an access device or other image processing device, executing specific computer-executable instructions.

Conditional language used herein, such as, among others. "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each is present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a structural element configured to carry out recitations A, B, and C" can include a first structural element configured to carry out recitation A working in conjunction with a second structural element configured to carry out recitations B and C.

As used herein, the terms "determine" or "determining" encompass a wide variety of actions. For example, "determining" may include calculating, computing, processing, deriving, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface or a UI) may refer to a network based interface including data fields and/or other controls for receiving input signals or providing electronic information and/or for providing information to the user in response to any received input signals. A UI may be implemented in whole or in part using technologies such as hyper-text mark-up language (HTML), Flash, Java, .net, web services, and rich site summary (RSS). In some implementations, a UI may be included in a stand-alone client (for example, thick client, fat client) configured to communicate (e.g., send or receive data) in accordance with one or more of the aspects described.

As used herein, the term "subject" encompasses a wide variety of organisms. A subject may be a human subject or a non-human subject. The subject may be a vertebrate or invertebrate. The subject may refer to the entire form of the organism or an identifiable portion thereof (e.g., limb, hand, organ, vascular pathway, etc.).

As used herein, the term "data point" generally refers to a single image taken from a single subject at a specified time point. The image may be a two dimensional image or a three dimensional image. The image may include pixel and/or voxel data. The image may also include metadata.

As used herein, the term "data set" generally refers to a collection of data points. Within a data set, the type of subject, the time point, the procedure, and/or the therapy can be varied. However, the features described allow for cross-correlation of the data points within the data set.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes that come within the meaning and range of equivalency of the claims are to be embraced within their scope.

Various other modifications, adaptations, and alternative designs are of course possible in light of the above teachings. Therefore, it should be understood at this time that within the scope of the appended claims the disclosure may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An apparatus for housing an animal for optical imaging, comprising:
    a top section configured to encapsulate at least part of an animal of a weight, the top section comprising a first end and a second end;
    a bottom section configured to encapsulate at least part of the animal of the weight, the bottom section comprising a first end and a second end; and
    a machine readable identifier affixed to at least one of: (a) the first end of the top section or (b) the second end of the top section, wherein the machine readable identifier indicates a position and the weight of the animal;
    wherein the first end of the top section is movably secured to the first end of the bottom section, such that the top section and bottom section are movable between an open position and a closed position;
    wherein the second end of the top section and the second end of the bottom section are configured to detachably engage one another, wherein when the second end of the top section and the second end of the bottom section are detachably engaged, the top section and bottom section defining an inner cavity configured to non-deformably encapsulate the animal and maintain an anatomy of the animal in a geometrically defined position;
    wherein the apparatus is configured to maintain the animal in the geometrically defined position to: (a) facilitate optical imaging of the animal at a plurality of views which can be merged to provide a single 360° view about an axis extending through the animal between a proximal end of the apparatus and a distal end of the apparatus when the second end of the top section and the second end of the bottom section are detachably engaged; and (b) provide a surface having a uniform thickness for camera detection points at a proximal region of the apparatus along the axis and at a distal region of the apparatus along the axis, wherein the camera detection points include an in vivo detection point.

2. The apparatus of claim 1, further comprising a hinge, the hinge comprising a pivot axis, wherein the first end of the top section is movably secured to the first end of the bottom section, wherein the top section and bottom section are rotatable about the pivot axis.

3. The apparatus of claim 1, further comprising a passage configured to receive a gas from a gas supply and to direct the gas to a cranial section of the apparatus, wherein the passage is formed from a portion of the first end of the top section and a portion of the first end of the bottom section when the top section and the bottom section are in the closed position.

4. The apparatus of claim 1, further comprising one or more passages configured to scavenge excess gas exterior to the apparatus, wherein the one or more passages are formed from a portion of the first end of the top section and a portion of the first end of the bottom section when the top section and the bottom section are in the closed position.

5. The apparatus of claim 1, wherein the first end of the bottom section comprises one or more wings configured to engage a support structure of an imaging apparatus to maintain the apparatus in a consistent position for optical imaging.

6. The apparatus of claim 5, wherein a wing included in the one or more wings is configured to engage with a slot of the imaging apparatus to align the apparatus with a nozzle configured to direct gas from an external source to the apparatus, wherein the support structure inhibits distal movement the wing with respect to the slot when engaged with the slot.

7. The apparatus of claim 1, wherein the machine readable identifier comprises a computer readable label storing data thereon.

8. The apparatus of claim 7, wherein the computer readable label is configured to store one or more of imaging data, customer data, and animal specimen data.

9. The apparatus of claim 1, wherein the top section and the bottom section are made from an optically transparent material comprising polycarbonate.

10. The apparatus of claim 1, wherein a portion of the animal shown in a first image captured using a first imaging modality is identifiable in a second image captured using a second imaging modality, wherein the second imaging modality is different from the first imaging modality, wherein the first imaging modality and the second imaging modality are each one of bioluminescence imaging (BLI), bioluminescence tomography (BLT), fluorescence, positron emission tomography (PET), single photon emission counting tomography (SPECT), magnetic resonance imaging (MRI), and computed tomography (CT).

11. An assembly for optical imaging of an animal housed in the apparatus of claim 1, comprising:
 a holder configured to secure the apparatus; and
 a docking interface configured to engage the holder, wherein the docking interface is further configured to allow for 180° rotation.

12. The assembly of claim 11, wherein the apparatus comprises:
 a hinge comprising a pivot axis, wherein the top section is moveably secured to the bottom section by the hinge, wherein the top section and the bottom section are configured to rotate about the pivot axis between a closed position and an open position.

13. The assembly of claim 11 further comprising:
 an apparatus receiving channel configured to receive a first end of the apparatus; and
 a nozzle extending through the apparatus receiving channel, wherein the nozzle is configured to direct gas from an external source to the apparatus.

14. The assembly of claim 13, wherein the apparatus receiving channel further comprises one or more slots, each slot configured to receive a wing of the apparatus, wherein each of the one or more slots is positioned to align the nozzle with the apparatus when the slot receives the wing of the apparatus.

15. The assembly of claim 14, further comprising a wire latch, wherein the wire latch is configured to extend around a portion of at least one of the one or more wings to secure the apparatus in position when the one or more wings are positioned within the one or more slots of the apparatus receiving channel.

16. The assembly of claim 13, further comprises one or more scavenging channels positioned within the apparatus receiving channel, the one or more scavenging channels configured to receive gas scavenged from the assembly exterior to the apparatus.

17. The assembly of claim 11, wherein the apparatus comprises a computer readable label, the computer readable label configured to be detectable in an optical image captured when the apparatus is secured in the holder.

18. An apparatus for housing an animal for optical imaging, comprising:
 a top section configured to encapsulate at least part of an animal of a weight, the top section comprising a first end and a second end;
 a bottom section configured to encapsulate at least part of the animal of the weight, the bottom section comprising a first end and a second end; and
 a machine readable identifier affixed to at least one of: (a) the first end of the top section or (b) the second end of the top section, wherein the machine readable identifier indicates a position and the weight of the animal;
 wherein the first end of the top section is movably secured to the first end of the bottom section, such that the top section and bottom section are movable between an open position and a closed position;
 wherein the second end of the top section and the second end of the bottom section are configured to detachably engage one another, wherein when the second end of the top section and the second end of the bottom section are detachably engaged, the top section and bottom section defining an inner cavity configured to non-deformably encapsulate the animal and maintain an anatomy of the animal in a geometrically defined position;
 wherein the apparatus is configured to maintain the animal in the geometrically defined position to facilitate optical imaging of the animal at a plurality of views which can be merged to provide a single 360° view about an axis extending through the animal and provide a uniform surface for camera detection points, wherein the camera detection points include an in vivo detection point, wherein the inner cavity is configured to non-deformably encapsulate the animal and maintain the anatomy of the animal in the geometrically defined position to facilitate coregistration of two dimensional data analysis and bioluminescence tomography to an anatomical atlas.

* * * * *